(12) United States Patent
Frustaci et al.

(10) Patent No.: US 10,449,375 B2
(45) Date of Patent: Oct. 22, 2019

(54) HERMETIC TERMINAL FOR AN AIMD HAVING A PIN JOINT IN A FEEDTHROUGH CAPACITOR OR CIRCUIT BOARD

(71) Applicant: Greatbatch Ltd., Clarence, NY (US)

(72) Inventors: Dominick J. Frustaci, Williamsville, NY (US); Keith W. Seitz, Clarence Center, NY (US); Thomas Marzano, East Amherst, NY (US); Robert A. Stevenson, Canyon Country, CA (US); Christine A. Frysz, Orchard Park, NY (US); Richard L. Brendel, Carson City, NV (US); Jason Woods, Carson City, NV (US)

(73) Assignee: Greatbatch Ltd., Clarence, NY (US)

( * ) Notice: Subject to any disclaimer, the term of this patent is extended or adjusted under 35 U.S.C. 154(b) by 93 days.

(21) Appl. No.: 15/844,683

(22) Filed: Dec. 18, 2017

(65) Prior Publication Data

US 2018/0178016 A1 Jun. 28, 2018

Related U.S. Application Data

(60) Provisional application No. 62/437,781, filed on Dec. 22, 2016.

(51) Int. Cl.
*A61N 1/375* (2006.01)
*H01G 4/35* (2006.01)
(Continued)

(52) U.S. Cl.
CPC ............. *A61N 1/3754* (2013.01); *A61N 1/05* (2013.01); *A61N 1/08* (2013.01); *H01G 2/103* (2013.01);
(Continued)

(58) Field of Classification Search
CPC .......... A61N 1/3754; A61N 1/05; A61N 1/08; H01G 4/40; H01G 2/103; H01G 4/35;
(Continued)

(56) References Cited

U.S. PATENT DOCUMENTS

| 4,424,551 A | 1/1984 | Stevenson et al. |
| 5,333,095 A | 7/1994 | Stevenson et al. |

(Continued)

*Primary Examiner* — Amanda K Hulbert
*Assistant Examiner* — Philip C Edwards
(74) *Attorney, Agent, or Firm* — Michael F. Scalise

(57) ABSTRACT

A hermetically sealed feedthrough subassembly attachable to an active implantable medical device includes a first conductive leadwire extending from a first end to a second end, the first conductive leadwire first end disposed past a device side of an insulator body. A feedthrough filter capacitor is disposed on the device side. A second conductive leadwire is disposed on the device side having a second conductive leadwire first end at least partially disposed within a first passageway of the feedthrough filter capacitor and having a second conductive leadwire second end disposed past the feedthrough filter capacitor configured to be connectable to AIMD internal electronics. The second conductive leadwire first end is at, near or adjacent to the first conductive leadwire first end. A first electrically conductive material forms a three-way electrical connection electrically connecting the second conductive leadwire first end, the first conductive leadwire first end and a capacitor internal metallization.

23 Claims, 37 Drawing Sheets

(51) Int. Cl.
*H01R 13/7195* (2011.01)
*H01G 2/22* (2006.01)
*H01G 2/10* (2006.01)
*A61N 1/08* (2006.01)
*H01G 4/40* (2006.01)
*A61N 1/05* (2006.01)
*H05K 1/02* (2006.01)

(52) U.S. Cl.
CPC ............... *H01G 2/22* (2013.01); *H01G 4/35* (2013.01); *H01G 4/40* (2013.01); *H01R 13/7195* (2013.01); *H05K 1/0231* (2013.01); *H05K 2201/10015* (2013.01); *H05K 2201/10189* (2013.01); *H05K 2201/10303* (2013.01)

(58) Field of Classification Search
CPC ............... H01G 2/22; H01R 13/7195; H05K 2201/10303; H05K 2201/10015; H05K 1/0231; H05K 2201/10189
USPC ............................................. 607/37
See application file for complete search history.

(56) References Cited

U.S. PATENT DOCUMENTS

| | | |
|---|---|---|
| 5,650,759 A | 7/1997 | Hittman et al. |
| 5,751,539 A | 5/1998 | Stevenson et al. |
| 5,896,267 A | 4/1999 | Hittman et al. |
| 5,905,627 A | 5/1999 | Brendel et al. |
| 5,959,829 A | 9/1999 | Stevenson et al. |
| 5,973,906 A | 10/1999 | Stevenson et al. |
| 5,978,204 A | 11/1999 | Stevenson |
| 6,008,980 A | 12/1999 | Stevenson et al. |
| 6,159,560 A | 12/2000 | Stevenson et al. |
| 6,275,379 B1 | 8/2001 | Sleboda et al. |
| 6,456,481 B1 | 9/2002 | Stevenson |
| 6,529,103 B1 | 3/2003 | Brendel et al. |
| 6,566,978 B2 | 5/2003 | Stevenson et al. |
| 6,567,259 B2 | 5/2003 | Stevenson et al. |
| 6,643,903 B2 | 11/2003 | Stevenson et al. |
| 6,765,779 B2 | 7/2004 | Stevenson |
| 6,765,780 B2 | 7/2004 | Brendel et al. |
| 6,888,715 B2 | 5/2005 | Stevenson et al. |
| 6,985,347 B2 | 1/2006 | Stevenson et al. |
| 6,987,660 B2 | 1/2006 | Stevenson et al. |
| 6,999,818 B2 | 2/2006 | Stevenson et al. |
| 7,012,192 B2 | 3/2006 | Stevenson et al. |
| 7,035,076 B1 | 4/2006 | Stevenson |
| 7,038,900 B2 | 5/2006 | Stevenson et al. |
| 7,113,387 B2 | 9/2006 | Stevenson et al. |
| 7,136,273 B2 | 11/2006 | Stevenson et al. |
| 7,199,995 B2 | 4/2007 | Stevenson |
| 7,310,216 B2 | 12/2007 | Stevenson et al. |
| 7,327,553 B2 | 2/2008 | Brendel |
| 7,489,495 B2 | 2/2009 | Stevenson |
| 7,535,693 B2 | 5/2009 | Stevenson et al. |
| 7,551,963 B2 | 6/2009 | Rusin et al. |
| 7,623,335 B2 | 11/2009 | Stevenson et al. |
| 7,797,048 B2 | 9/2010 | Stevenson et al. |
| 7,957,806 B2 | 6/2011 | Stevenson et al. |
| 8,095,224 B2 | 1/2012 | Truex et al. |
| 8,179,658 B2 | 5/2012 | Stevenson et al. |
| 8,604,341 B2 | 12/2013 | Barry et al. |
| 8,927,862 B2 | 1/2015 | Barry et al. |
| 9,431,814 B2 | 8/2016 | Blilie et al. |
| 2014/0168917 A1 | 6/2014 | Marzano et al. |
| 2014/0243944 A1 | 8/2014 | Stevenson et al. |
| 2015/0245468 A1 | 8/2015 | Barry et al. |
| 2016/0287883 A1 | 10/2016 | Barry et al. |

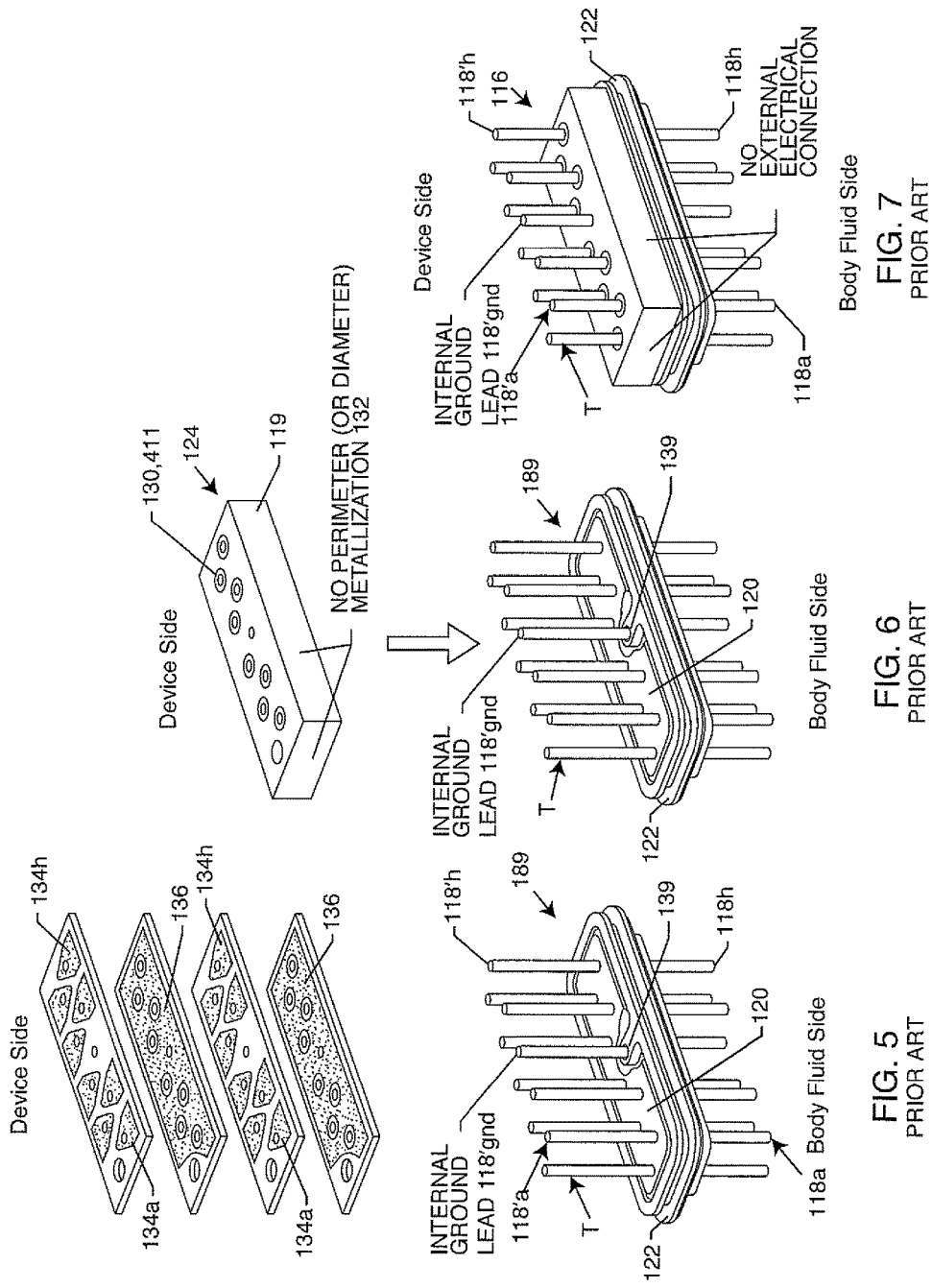

DEVICE SIDE

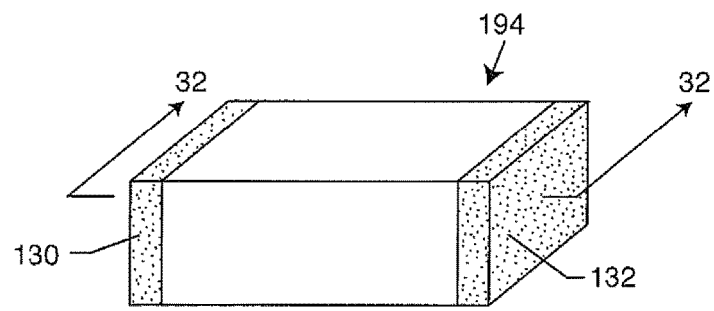
FIG. 31
PRIOR ART
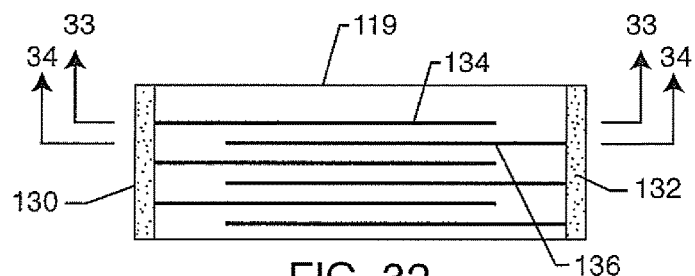
FIG. 32
PRIOR ART
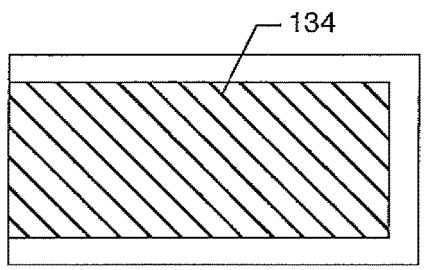 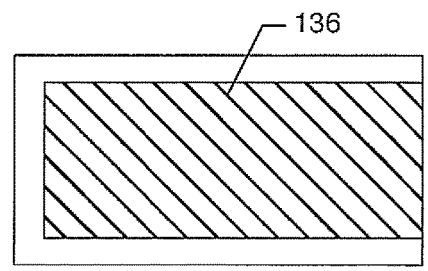
FIG. 33　　　　　　　　　　FIG. 34
PRIOR ART　　　　　　　　　PRIOR ART

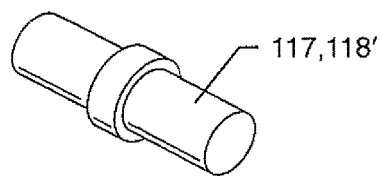
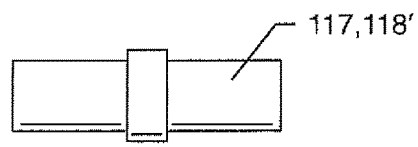
FIG. 41A  FIG. 41B
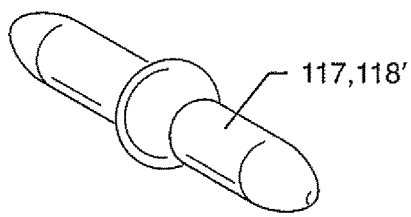
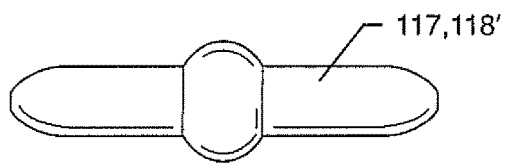
FIG. 42A  FIG. 42B
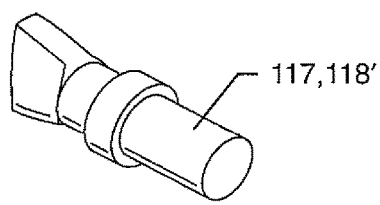
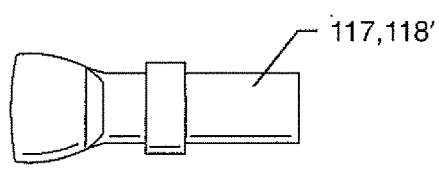
FIG. 43A  FIG. 43B
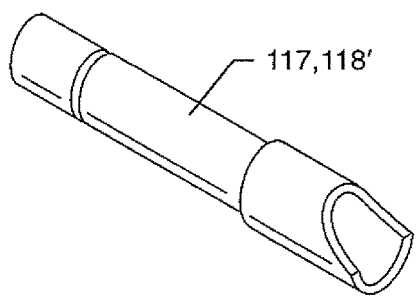
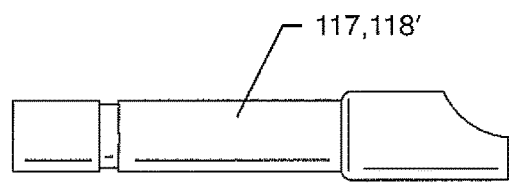
FIG. 44A  FIG. 44B

| Composition | M.P. °C S/L | Eutectic | Sn | Pb | Ag | Cu | Sb | Bi | In | Zn | Cd | Au | oth. |
|---|---|---|---|---|---|---|---|---|---|---|---|---|---|
| Au$_{82}$In$_{18}$ | 451/485 | no | | | | | | | 18 | | | 82 | |
| Au$_{96.8}$Si$_{3.2}$ | 370/363 | yes | | | | | | | | | | 96.8 | Si$_{3.2}$ |
| Au$_{96}$Si$_{4}$ | 370/800 | yes | | | | | | | | | | 96 | Si$_{4}$ |
| Au$_{87.5}$Ge$_{12.5}$ | 361/356 | yes | | | | | | | | | | 87.5 | Ge$_{12.5}$ |
| Cd$_{95}$Ag$_{5}$ | 338/393 | no | | | | | | | | | 95 | | |
| Pb$_{92}$Cd$_{8}$ | 310 | | | | | | | | | | 8 | | |
| Pb$_{97}$Ag$_{1.5}$Sn$_{1}$ | 309 | yes | 1 | 92 | 1.5 | | | | | | | | |
| Pb$_{95}$Ag$_{5}$ | 305/364 | no | | 95 | 5 | | | | | | | | |
| Pb$_{94.5}$Ag$_{5.5}$ | 304/343 | no | | 94.5 | 5.5 | | | | | | | | |
| Pb$_{95}$Ag$_{2.5}$ | 304/579 | yes | | 97.5 | 2.5 | | | | | | | | |
| Pb$_{92.5}$Sn$_{5}$Ag$_{2.5}$ | 300/310 | no | 5 | 92.5 | 2.5 | | | | | | | | |
| Pb$_{92.5}$In$_{5}$Ag$_{2.5}$ | 300/310 | no | | 92.5 | 2.5 | | | | 5 | | | | |
| Pb$_{95.5}$Sn$_{2}$Ag$_{2.5}$ | 299/304 | no | 2 | 95.5 | 2.5 | | | | | | | | |
| Pb$_{93.5}$Sn$_{5}$Ag$_{1.5}$ | 296/301 | no | 5 | 93.5 | 1.5 | | | | | | | | |
| Pb$_{90}$Sn$_{5}$Ag$_{5}$ | 292 | yes | 5 | 90 | 5 | | | | | | | | |
| Pb$_{90}$In$_{5}$Ag$_{5}$ | 290/310 | no | | 90 | 5 | | | | 5 | | | | |
| Pb$_{92.5}$Sn$_{5}$Ag$_{2.5}$ | 287/296 | no | 5 | 92.5 | 2.5 | | | | | | | | |
| Pb$_{92}$Sn$_{5.5}$Ag$_{2.5}$ | 286/301 | no | 5.5 | 92 | 2.5 | | | | | | | | |
| Pb$_{81}$In$_{19}$ | 260/275 | no | | 81 | | | | | 19 | | | | |
| Pb$_{99}$Sn$_{1}$ | 268/302 | no | 10 | 90 | | | | | | | | | |
| Pb$_{88}$Sn$_{10}$Ag$_{2}$ | 268/290 | no | 10 | 88 | 2 | | | | | | | | |
| Cd$_{82.5}$Zn$_{17.5}$ | 265 | yes | | | | | | | | 17.5 | 82.5 | | |
| Zn$_{90}$Cd$_{10}$ | 265/399 | no | | | | | | | | 90 | 10 | | |
| Zn$_{60}$Cd$_{40}$ | 265/335 | no | | | | | | | | 60 | 40 | | |
| Cd$_{60}$Zn$_{40}$ | 265/316 | no | | | | | | | | 40 | 60 | | |
| Cd$_{70}$Zn$_{30}$ | 265/300 | no | | | | | | | | 30 | 70 | | |
| Pb$_{88}$Sn$_{12}$ | 254/296 | no | 12 | 88 | | | | | | | | | |
| Pb$_{96}$Sn$_{2}$Ag$_{2}$ | 252/295 | no | 2 | 96 | 2 | | | | | | | | |
| Pb$_{80}$Sn$_{18}$Ag$_{2}$ | 252/260 | no | 18 | 80 | 2 | | | | | | | | |
| Pb$_{75}$In$_{25}$ | 240/260 | no | | 75 | | | | | 25 | | | | |
| Cd$_{5}$Zn$_{17}$Ag$_{78}$ | 249/316 | no | | | 5 | | | | | 17 | 78 | | |
| Pb$_{70}$In$_{30}$ | 245/260 | no | | 70 | | | | | 30 | | | | |
| Pb$_{85}$Sn$_{15}$ | 227/288 | no | 15 | 85 | | | | | | | | | |

FIG. 51

HERMETIC TERMINAL FOR AN AIMD HAVING A PIN JOINT IN A FEEDTHROUGH CAPACITOR OR CIRCUIT BOARD

CROSS-REFERENCE TO RELATED APPLICATIONS

This non-provisional patent application claims priority to provisional application 62/437,781 filed on Dec. 22, 2016, the entire contents of which are fully incorporated herein with this reference.

FIELD OF THE INVENTION

The present invention generally relates to implantable medical devices and hermetic terminal subassemblies. More particularly, the present invention relates a hermetic terminal having a composite conductive lead having pin joint in a feedthrough capacitor or circuit board.

BACKGROUND OF THE INVENTION

A wide assortment of active implantable medical devices (AIMD) are presently known and in commercial use. Such devices include cardiac pacemakers, cardiac defibrillators, cardioverters, neurostimulators, and other devices for delivering and/or receiving electrical signals to/from a portion of the body. Sensing and/or stimulating leads extend from the associated implantable medical device to a distal tip electrode or electrodes in contact with body tissue.

The hermetic terminal or feedthrough of these implantable devices is considered critical. Hermetic terminals or feedthroughs are generally well-known in the art for connecting electrical signals through the housing or case of an AIMD. For example, in implantable medical devices such as cardiac pacemakers, implantable cardioverter defibrillators, and the like, a hermetic terminal comprises one or more conductive pathways which may include conductive terminal pins, conductive filled vias, leadwires and the like supported by an insulative structure for feedthrough passage from the exterior to the interior of an AIMD electromagnetic shield housing. Hermetic terminals or feedthroughs for AIMDs must be biocompatible as well as resistant to degradation under applied bias current or voltage (biostable). Hermeticity of the feedthrough is imparted by judicious material selection and carefully prescribed manufacturing processing. Sustainable hermeticity of the feedthrough over the lifetime of these implantable devices is critical because the hermetic terminal intentionally isolates the internal circuitry and components of the device (AIMD) from the external environment to which the component is exposed. In particular, the hermetic terminal isolates the internal circuitry, connections, power sources and other components in the device from ingress of body fluids. Ingress of body fluids into an implantable medical device is known to be a contributing factor to device malfunction and may contribute to the compromise or failure of electrical circuitry, connections, power sources and other components within an implantable medical device that are necessary for consistent and reliable device therapy delivery to a patient. Furthermore, ingress of body fluids may compromise an implantable medical device's functionality which may constitute electrical shorting, element or joint corrosion, metal migration or other such harmful consequences affecting consistent and reliable device therapy delivery.

In addition to concerns relative to sustained terminal or feedthrough hermeticity, other potentially compromising conditions must be addressed, particularly when a hermetic terminal or feedthrough is incorporated within an implantable medical device. For example, the hermetic terminal or feedthrough pins are typically connected to one or more leadwires of implantable therapy delivery leads. These implantable therapy delivery leads can effectively act as antennas of electromagnetic interference (EMI) signals. Therefore, when these electromagnetic signals enter within the interior space of a hermetic implantable medical device, facilitated by the therapy delivery leads, they can negatively impact the intended function of the medical device and as a result, negatively impact therapy delivery intended for a patient by that device. EMI engineers commonly refer to this as the "genie in the bottle" effect. In other words, once the genie (i.e., EMI) is inside the hermetic housing of the device, it can wreak havoc with electronic circuit functions by cross-coupling and re-radiating within the device.

Another particularly problematic condition associated with implanted therapy delivery leads occurs when a patient is in an MRI environment. In this case, the electrical currents imposed on the implanted therapy delivery leads can cause the leads to heat to the point where tissue damage is likely. Moreover, RF currents (electromagnetic interference—EMI) may be coupled to implanted therapy delivery leads resulting in undesirable electrical currents which can enter the AIMD and can disrupt or damage the sensitive electronics within the implantable medical device.

Therefore, materials selection and fabrication processing parameters are of utmost importance in creating a hermetic terminal (or feedthrough) or a structure embodying a hermetic terminal (or feedthrough), that can survive anticipated and possibly catastrophically damaging environmental conditions and that can be practically and cost effectively manufactured.

Hermetic terminals or feedthrough assemblies utilizing ceramic dielectric materials may fail in a brittle manner. A brittle failure typically occurs when the ceramic structure is deformed elastically up to an intolerable stress, at which point the ceramic fails catastrophically. Most brittle failures occur by crack propagation in a tensile stress field. Even microcracking caused by sufficiently high tensile stress concentrations may result in a catastrophic failure including loss of hermeticity identified as critical in hermetic terminals for implantable medical devices. Loss of hermeticity may be a result of design aspects such as a sharp corner which creates a stress riser, mating materials with a difference of coefficient of thermal expansions (CTE) that generate tensile stresses that ultimately result in loss of hermeticity of the feedthrough or interconnect structure.

In the specific case of hermetic terminal or feedthrough designs, a tensile stress limit for a given ceramic based hermetic design structure cannot be specified because failure stress in these structures is not a constant. As indicated above, variables affecting stress levels include the design itself, the materials selection, symmetry of the feedthrough, and the bonding characteristics of mating surfaces within the feedthrough. Hence, length, width and height of the overall ceramic structure matters as do the number, spacing, length and diameter of the conductive pathways (vias, terminal pins, leadwires, etc.) in that structure. The selection of the mating materials, that is, the material that fills the vias (or leadwire) and the material that forms the base ceramic, are important. Finally, the fabrication processing parameters, particularly at binder burnout, sintering and cool down, make a difference. When high reliability is required in an application such as indicated with hermetic terminals or feedthroughs for AIMDs, to provide insurance for a very low probability of failure it is necessary to design a hermetic terminal assembly or feedthrough structure so that stresses imparted by design, materials and/or processing are limited to a smaller level of an average possible failure stress. Further, to provide insurance for a very low probability of failure in a critical ceramic based assembly or subassembly having sustainable hermetic requirements, it is also necessary to design structures embodying a hermetic terminal or feedthrough such that stresses in the final assembly or subassembly are limited to a smaller level of an average possible failure stress for the entire assembly or subassembly. In hermetic terminals and structures comprising hermetic terminals for AIMDs wherein the demand for biocompatibility exists, this task becomes even more difficult.

The most critical feature of a feedthrough design or any terminal subassembly is the metal/ceramic interface within the feedthrough that establishes the hermetic seal. One embodiment of the present invention therefore provides where a hermetic feedthrough comprising a monolithic alumina insulator substrate within which a platinum conductive pathway or via resides or wherein a metallic leadwire (terminal pin) resides. More specifically in the case of a filled via, the present invention provides a hermetic feedthrough in which the hermetic seal is created through the intimate bonding of a platinum metal residing within the alumina substrate.

A traditional ceramic-to-metal hermetic terminal is an assembly of three components: electrical conductors (leadwires, pins, terminal pins, filled vias) that conduct electrical current, a ceramic insulator, and a metal housing, which is referred to as the flange or the ferrule. Brazed joints typically hermetically seal the metal leadwires and the flange or ferrule to the ceramic insulator. For a braze-bonded joint, the braze material is generally intended to deform in a ductile manner in order to compensate for perturbations that stress the bond between the mating materials as the braze material may provide ductile strain relief when the thermal expansion mismatch between the ceramic and metal is large. Thus, mating materials with large mismatches in CTE can be coupled through braze materials whose high creep rate and low yield strength reduce the stresses generated by the differential contraction existing between these mating materials.

Thermal expansion of metal is generally considerably greater than those of ceramics. Hence, successfully creating a hermetic structure, and one that can sustain its hermeticity in service, is challenging due to the level of residual stresses in the final structure. Specifically, thermal expansion mismatch results in stresses acting along the ceramic/metal interface that tend to separate the ceramic from the metal and so the bond developed between the ceramic and the metal must be of sufficient strength to withstand these stresses, otherwise adherence failure, that is, loss of hermeticity, will occur. One method for limiting these stresses is to select combinations of materials whose thermal contractions after bonding are matched.

In making the selection for a CTE match, it is important to note that very few pairs of materials have essentially identical thermal expansion curves. Generally, the metal component is selected first based on electrical and thermal conductivity, thermal expansion, ability to be welded or soldered, mechanical strength, and chemical resistance or biocompatibility requirements. The ceramic is then selected based primarily on electrical resistivity, dielectric strength, low gas permeability, environmental stability, and thermal expansion characteristics. In the specific case of selecting platinum wire, often the ceramic formulation is modified in order to match its CTE to that of the platinum wire. In yet a more specific case of selecting platinum paste, the platinum paste formulation may be modified as well. If the mating materials are alumina of at least 96% purity and essentially pure platinum paste, then matching CTE is not possible. Thus, for AIMD's, consistently achieving hermetic terminal structures that are capable of sustaining hermeticity throughout the application's service life has proven challenging. Another solution would be to use a cermet which is part ceramic and part metal. For example, the cermet could be an alumina/platinum paste that then had a closer CTE to that of the alumina insulator.

Producing a stress-free structure often not only involves bonding a pair of materials but also achieving that bond at a very specific temperature so that their contractions on cooling to room temperature are essentially the same even though the contraction curves may not coincide. Since this often is a significant challenge, hermetic terminals are produced by metalizing the alumina and using a brazing material to form the bond at some other temperature than an intersection of the CTE curves. (NOTE: Forming a bond between two materials that become rigid at the intersection of the two CTE curves makes it possible to produce a structure that is stress free at room temperature, unless the two CTE curves separate substantially from each other from the intersection point and room temperature.) The deformation of the braze material by time-independent plastic flow or creep relaxation limits the stresses generated in the ceramic. Given this, the impact of the rate of cooling on the final stress level of a structure must also be considered. In some cases, residual stresses are generated deliberately to provide protective compressive stresses in the ceramic part and in the bond interface. Usually this is accomplished by selecting components with different CTEs. Another way is to control the shrinkage of one material over its mating material. In either case, it is important to minimize stress levels such that the interface on which hermeticity depends is well within the stress level at which failure might occur.

In an embodiment, the present invention is directed to mating bound particulate high purity alumina of at least 96% and particles of essentially pure platinum metal that are suspended within a mixture of solvents and binders, i.e., a platinum paste. This combination of materials does not use a braze material to buffer the CTE mismatch between these two materials. Further, since the intent of this embodiment is to provide hermetic terminals and subassemblies comprising hermetic terminals for AIMDs, this particularly embodiment does not consider modifications to the alumina formulation or the platinum paste in an attempt to match their CTEs. Rather, this embodiment discloses sustainable hermetic terminals and structures embodying these hermetic terminals. This is achieved by adjusting platinum paste solids loading, prescribing via packing, prescribing binder burnout, sintering and cool down parameters, such that shrinkage of the alumina is greater than the shrinkage of the platinum fill in the via and an intimate and tortuous (a mutually conformal) interface is created that may be either a direct bond between the alumina and platinum materials that is hermetic, or alternatively, that may develop an amorphous interfacial layer that is not susceptible to erosion by body fluids and can tolerate stress levels without losing hermeticity. (It will be understood by those skilled in the art, that this teaching contains other embodiments that are not dependent upon using an essentially pure platinum paste as a conductive fill. Furthermore, many of the embodiments presented herein don't use a conductive filled via but rather a leadwire.)

Regarding EMI, a terminal or feedthrough capacitor EMI filter may be disposed at, near or within a hermetic terminal or feedthrough resulting in a feedthrough filter capacitor which diverts high frequency electrical signals from lead conductors to the housing or case of an AIMD. Many different insulator structures and related mounting methods are known in the art for use of feedthrough capacitor EMI filters in AIMDs, wherein the insulative structure also provides a hermetic terminal or feedthrough to prevent entry of body fluids into the housing of an AIMD. In the prior art devices, the hermetic terminal subassembly has been combined in various ways with a ceramic feedthrough filter EMI capacitor to decouple interference signals to the housing of the medical device.

In a typical prior art unipolar construction (as described in U.S. Pat. No. 5,333,095 and herein incorporated by reference), a round/discoidal (or rectangular) ceramic feedthrough EMI filter capacitor is combined with a hermetic terminal pin assembly to suppress and decouple undesired interference or noise transmission along a terminal pin. The feedthrough capacitor is coaxial having two sets of electrode plates embedded in spaced relation within an insulative dielectric substrate or base, formed typically as a ceramic monolithic structure. One set of the electrode plates are electrically connected at an inner diameter cylindrical surface of the coaxial capacitor structure to the conductive terminal pin utilized to pass the desired electrical signal or signals. The other or second set of electrode plates are coupled at an outer diameter surface of the round/discoidal capacitor to a cylindrical ferrule of conductive material, wherein the ferrule is electrically connected in turn to the conductive housing of the electronic device. The number and dielectric thickness spacing of the electrode plate sets varies in accordance with the capacitance value and the voltage rating of the coaxial capacitor. The outer feedthrough capacitor electrode plate sets (or "ground" plates) are coupled in parallel together by a metalized layer which is fired, sputtered or plated onto the ceramic capacitor. This metalized band, in turn, is coupled to the ferrule by conductive adhesive, soldering, brazing, welding, or the like. The inner feedthrough capacitor electrode plate sets (or "active" plates) are coupled in parallel together by a metalized layer which is either glass frit fired or plated onto the ceramic capacitor. This metalized band, in turn, is mechanically and electrically coupled to the lead wire(s) by conductive adhesive, soldering, or the like. In operation, the coaxial capacitor permits passage of relatively low frequency biologic signals along the terminal pin, while shielding and decoupling/attenuating undesired interference signals of typically high frequency to the AIMD conductive housing. Feedthrough capacitors of this general type are available in unipolar (one), bipolar (two), tripolar (three), quad polar (four), pentapolar (five), hexpolar (6) and additional lead configurations. The feedthrough capacitors (in both discoidal and rectangular configurations) of this general type are commonly employed in implantable cardiac pacemakers and defibrillators and the like, wherein the pacemaker housing is constructed from a biocompatible metal such as titanium alloy, which is electrically and mechanically coupled to the ferrule of the hermetic terminal pin assembly which is in turn electrically coupled to the coaxial feedthrough filter capacitor. As a result, the filter capacitor and terminal pin assembly prevents entrance of interference signals to the interior of the pacemaker housing, wherein such interference signals could otherwise adversely affect the desired cardiac pacing or defibrillation function.

Referring once again to feedthrough capacitor EMI filter assemblies, although these assemblies as described earlier have performed in a generally satisfactory manner, and notwithstanding that the associated manufacturing and assembly costs are unacceptably high in that the choice of the dielectric material for the capacitor has significant impacts on cost and final performance of the feedthrough filter capacitor, alumina ceramic has not been used in the past as the dielectric material for AIMD feedthrough capacitors. Alumina ceramic is structurally strong and biocompatible with body fluids but has a dielectric constant around 6 (less than 10). There are other more effective dielectric materials available for use in feedthrough filter capacitor designs. Relatively high dielectric constant materials (for example, barium titivate with a dielectric constant of over 2,000) are traditionally used to manufacture AIMD feedthrough capacitors for integrated ceramic capacitors and hermetic seals resulting in more effective capacitor designs. Yet ceramic dielectric materials such as barium titinate are not as strong as the alumina ceramic typically used to manufacture the hermetic seal subassembly in the prior art. Barium titinate is also not biocompatible with body fluids. Direct assembly of the ceramic capacitor can result in intolerable stress levels to the capacitor due to the mismatch in coefficients of thermal expansion between the titanium pacemaker housing (or other metallic structures) and the capacitor dielectric. Hence, particular care must be used to avoid cracking of the capacitor element. Accordingly, the use of dielectric materials with a low dielectric constant and a relatively high modulus of toughness are desirable yet still difficult to achieve for capacitance-efficient designs.

Therefore, it is very common in the prior art to construct a hermetic terminal subassembly with a feedthrough capacitor attached near the inside of the AIMD housing on the device side. The feedthrough capacitor does not have to be made from biocompatible materials because it is located on the device side inside the AIMD housing. The hermetic terminal subassembly includes conductive pathways (leadwires, pins, terminal pins, filled vias, etc.) to hermetically pass through the insulator in non-conductive relation with the ferrule or the AIMD housing. The conductive pathways also pass through the feedthrough hole of the capacitor to electronic circuits disposed inside of the AIMD housing. These leadwires are typically electrically continuous and, on the body fluid side, must be biocompatible and non-toxic. Generally, these conductive pathways are constructed of platinum or platinum-iridium, palladium or palladium-iridium, niobium pins or filled vias with conductive powders, ceramics, gradient materials or the like. Platinum-iridium is an ideal choice because it is biocompatible, non-toxic and is also mechanically very strong. The iridium is added to enhance material stiffness and to enable the hermetic terminal subassembly leadwire to sustain bending stresses. An issue with the use of platinum for leadwires is that platinum has become extremely expensive and may be subject to premature fracture under rigorous processing such as ultrasonic cleaning or application use/misuse, possibly unintentional damaging forces resulting from Twiddler's Syndrome. Twiddler's Syndrome is a situation documented in the literature where a patient will unconsciously or knowingly twist the implantable device to the point where attached leads may even fracture.

Accordingly, what is needed is a filtered structure like a hermetic terminal or feedthrough, any subassembly made using same and any feedthrough filter EMI capacitor assembly which minimizes intolerable stress levels, allows use of preferred materials for AIMDs or eliminates high-priced, platinum, platinum-iridium or equivalent noble metal hermetic terminal subassembly leadwires. Also, what may be needed is an efficient, simple and robust way to connect the leadwires in a header block to the novel hermetic terminal subassembly. Correspondingly, it is also needed to make a similar efficient, simple and robust electrical connection between the electronics on the device side of the AIMD to the feedthrough capacitor and hermetic terminal subassembly. The present invention fulfills these needs and provides other related advantages.

SUMMARY OF THE INVENTION

An exemplary embodiment of a hermetically sealed feedthrough subassembly 116 which is attachable to an active implantable medical device 100 (AIMD), includes: (a) an insulator substrate assembly 189, comprising: i) an insulator body 188 defined as having a body fluid side 320 opposite a device side 322, the body fluid side and device side separated and connected by at least one outer perimeter surface 321; ii) at least one via hole 333 disposed through the insulator body extending from the body fluid side to the device side; iii) an internal metallization 150,152 formed at least partially on an inside of the at least one via hole; iv) a first conductive leadwire 118 extending from a first end 337 to a second end 335, wherein the first conductive leadwire is at least partially disposed within the at least one via hole and wherein the first conductive leadwire first end 337 is disposed past the device side of the insulator body; v) a first braze 138 at least partially between the first conductive leadwire and the internal metallization, the first braze forming a first hermetic seal separating the body fluid side from the device side; and vi) an external metallization 150,152 disposed at least partially on the at least one outer perimeter surface of the insulator body; and (b) a ferrule 122, comprising: i) a conductive ferrule body 122 defined as having a first ferrule side 338 opposite a second ferrule side 339 and defining a ferrule opening 340 between and through the first and second ferrule sides, wherein the insulator body is at least partially disposed within the ferrule opening; ii) a second braze 140 at least partially between the external metallization of the insulator body and the conductive ferrule body, the second braze forming a second hermetic seal hermetically sealing the ferrule opening; (c) a feedthrough filter capacitor 124 disposed on the device side, the feedthrough filter capacitor comprising: i) at least one active electrode plate 134 disposed parallel and spaced from at least one ground electrode plate 136, wherein the plates are disposed within a capacitor dielectric substrate 119; ii) a first passageway 143 disposed through the capacitor dielectric substrate and disposed perpendicular to the plates; iii) a capacitor internal metallization 130 disposed within the first passageway electrically connected to the at least one active electrode plate and in non-conductive relation with the at feast one ground electrode plate; iv) wherein the first conductive leadwire first end 337 is disposed within the first passageway 143; (d) a second conductive leadwire 118' disposed on the device side having a second conductive leadwire first end 341 at least partially disposed within the first passageway of the feedthrough filter capacitor and having a second conductive leadwire second end 342 disposed past the feedthrough filter capacitor configured to be connectable to electronics internal 126 to the AIMD, wherein the second conductive leadwire first end 341 is at, near or adjacent to the first conductive leadwire first end 337; and (e) a first electrically conductive material 410 forming at least a three-way electrical connection electrically connecting the second conductive leadwire first end 341, the first conductive leadwire first end 337 and the capacitor internal metallization 130.

In other exemplary embodiments, the first electrically conductive material may be selected from the group consisting of a solder, a solder BGA, a solder paste, an epoxy, and a polyimide. The first conductive leadwire may not be the same material as the second conductive leadwire. The first conductive leadwire may comprise platinum, palladium, niobium or tantalum.

The first braze and second braze may each comprise a gold braze. The first braze may be disposed at or near the device side and may not extend to at or near the body fluid side. The first braze may be disposed at or near the device side and may extend to at or near the body fluid side.

The first and second hermetic seals may have a leak rate no greater than 1×10−7 std cc He/sec.

The external metallization may be disposed at least partially on the at least one outer perimeter surface of the insulator body and comprise an adhesion metallization and a wetting metallization, wherein the adhesion metallization is disposed at least partially on the at least one outer perimeter surface of the insulator body and wherein the wetting metallization is disposed on the adhesion metallization.

An insulative washer 206 may be disposed between the insulator substrate assembly and the feedthrough filter capacitor.

The ferrule may be configured to be joined to an AIMD housing by a laser weld or braze 128.

The ferrule is formed from and as a continuous part of an AIMD housing.

A capacitor external metallization 132 may be disposed on an outside perimeter surface of the capacitor dielectric substrate and electrically connected to the at least one ground electrode plate and in non-conductive relation with the at least one active electrode plate. A second electrically conductive material 148 may electrically connect the capacitor external metallization to the ferrule and/or to the second braze.

At least one internal ground plate 137 may be disposed within the insulator body and electrically connected to the at least one ground electrode plate of the feedthrough filter capacitor and to the ferrule.

A third conductive leadwire may be at least partially disposed within the insulator body and having a third conductive leadwire first end disposed past the device side of the insulator body.

A braze channel 408 may be electrically connected to the third conductive leadwire and the ferrule.

A conductive clip 141 may be electrically connected between and to the third conductive leadwire and the ferrule.

The conductive ferrule body may include a conductive peninsula 139 extending at least partially into the ferrule opening, wherein the third conductive leadwire is electrically connected to the conductive peninsula with a third braze.

Another exemplary embodiment of a hermetically sealed feedthrough subassembly 116 attachable to an active implantable medical device 100 (AIMD), includes: (a) an insulator substrate assembly 189, comprising: i) an insulator body 188 defined as having a body fluid side 320 opposite a device side 322, the body fluid side and device side separated and connected by at least one outer perimeter surface 321; ii) at least one via hole 333 disposed through the insulator body extending from the body fluid side to the device side; iii) an internal metallization 150,152 formed at least partially on an inside of the at least one via hole; iv) a first conductive leadwire 118 extending from a first end 337 to a second end 335, wherein the first conductive leadwire is at least partially disposed within the at least one via hole and wherein the first conductive leadwire first end 337 is disposed past the device side of the insulator body; v) a first braze 138 at least partially between the first conductive leadwire and the internal metallization, the first braze forming a first hermetic seal separating the body fluid side from the device side; and vi) an external metallization 150,152 disposed at least partially on the at least one outer perimeter surface of the insulator body; and (b) a ferrule 122, comprising: i) a conductive ferrule body 122 defined as having a first ferrule side 338 opposite a second ferrule side 339 and defining a ferrule opening 340 between and through the first and second ferrule sides, wherein the insulator body is at least partially disposed within the ferrule opening; ii) a second braze 140 at least partially between the external metallization of the insulator body and the conductive ferrule body, the second braze forming a second hermetic seal hermetically sealing the ferrule opening; (c) a circuit board 147 disposed on the device side, the circuit board comprising a first passageway 163 disposed through the circuit board, wherein the first conductive leadwire first end is disposed within the first passageway; (d) a second conductive leadwire 118' disposed on the device side having a second conductive leadwire first end 341 at least partially disposed within the first passageway of the circuit board and having a second conductive leadwire second end 342 disposed past the circuit board configured to be connectable to electronics internal 126 to the AIMD, wherein the second conductive leadwire first end 341 is at, near or adjacent to the first conductive leadwire first end 337, wherein the first and second conductive leadwires are electrically connected, and wherein the first conductive leadwire is not the same material as the second conductive leadwire.

In other exemplary embodiments, a chip capacitor 194 may be disposed on the circuit board, the chip capacitor comprising: i) at least one active electrode plate 134 disposed parallel and spaced from at least one ground electrode plate 136, wherein the plates are disposed within a capacitor dielectric substrate 119; ii) a first capacitor metallization 130 disposed on one end of the chip capacitor and electrically connected to the at least one active electrode plate and in non-conductive relation with the at least one ground electrode plate; iii) a second capacitor metallization 132 disposed on another end of the chip capacitor and electrically connected to the at least one ground electrode plate and in non-conductive relation with the at least one active electrode plate.

The first capacitor metallization may be electrically connected to the second conductive leadwire and/or first conductive leadwire.

The second capacitor metallization may be electrically connected to the ferrule and/or the second gold braze.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 5 illustrates an exploded perspective view of an internally grounded prior art feedthrough capacitor;

FIG. 6 illustrates the structure of FIG. 6 where now the capacitor is formed as a monolithic structure;

FIG. 7 illustrates the structure of FIGS. 6 and 7 fully assembled into a feedthrough filtered hermetic terminal;

FIG. 31 illustrates a prior art monolithic ceramic capacitor;

FIG. 32 illustrates a cross-section of an MLCC capacitor of FIG. 31 taken along lines 32-32;

FIG. 33 illustrates a cross-section of the MLCC capacitor of FIG. 32 taken along lines 33-33;

FIG. 34 illustrates a cross-section of the MLCC capacitor of FIG. 32 taken along lines 34-34;

FIG. 41A is a perspective view of a new embodiment of pin used in the present invention;

FIG. 41B is the side view of the structure of FIG. 41A;

FIG. 42A is a perspective view of new embodiment of pin used in the present invention;

FIG. 42B is the side view of the structure of FIG. 42A;

FIG. 43A is a perspective view of new embodiment of pin used in the present invention;

FIG. 43B is the side view of the structure of FIG. 43A;

FIG. 44A is a perspective view of new embodiment of pin used in the present invention;

FIG. 44B is the side view of the structure of FIG. 44A;

FIG. 51 is a chart detailing various solder compositions that may be used when manufacturing the present invention.

DETAILED DESCRIPTION OF THE PREFERRED EMBODIMENTS

Figure 1:
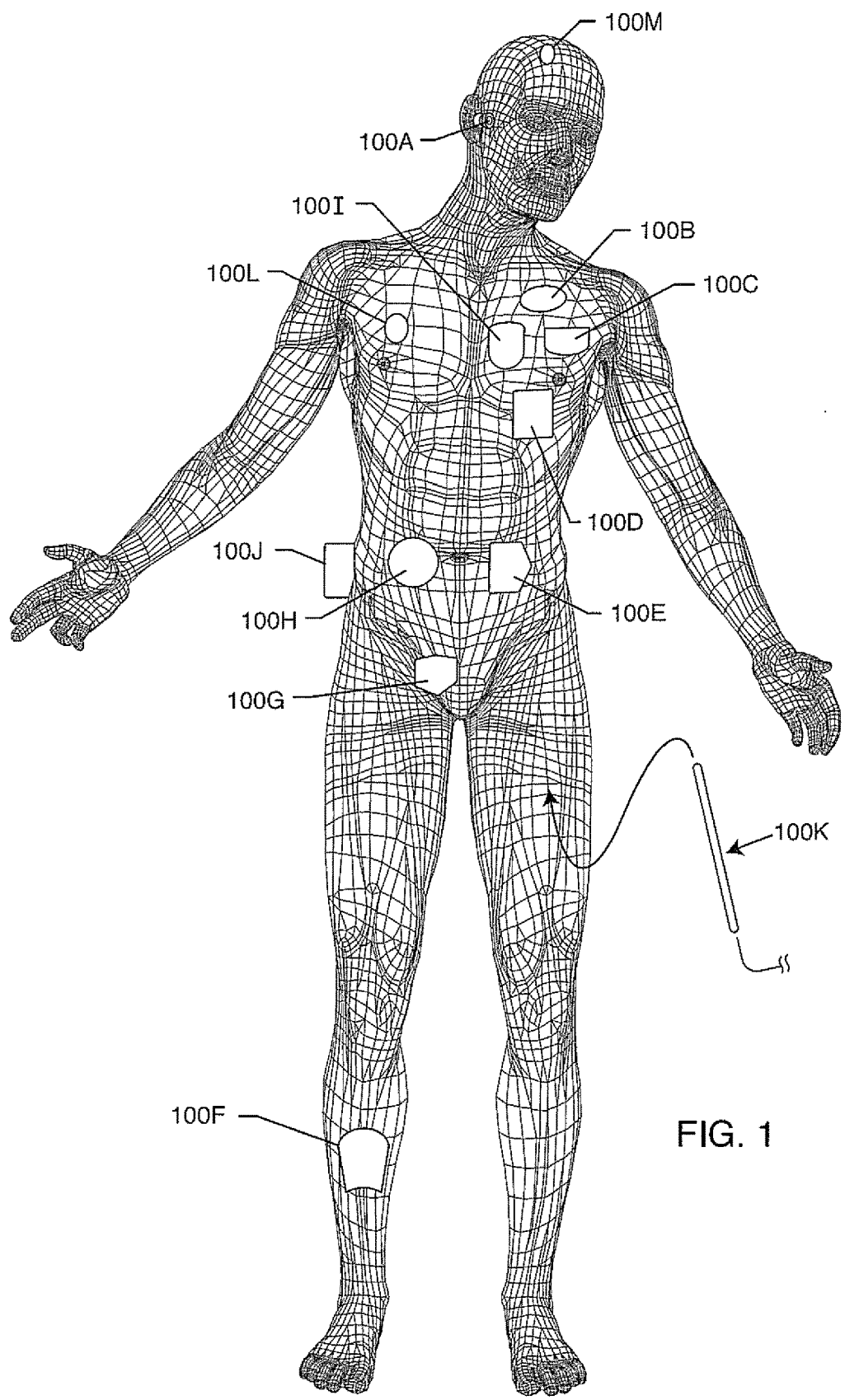
FIG. 1 is a wire-formed diagram of a generic human body showing a number of exemplary implantable medical devices.

FIG. 1 illustrates various types of active implantable and external medical devices 100 that are currently in use. FIG. 1 is a wire formed diagram of a generic human body showing a number of implanted medical devices. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of a seizure and also providing electrical stimulation to brain tissue to prevent the seizure from actually happening. The lead wires that come from a deep brain stimulator are often placed using real time imaging. Most commonly such lead wires are placed during real time MRI. 100C shows a cardiac pacemaker, which is well-known in the art, may have endocardial or epicardial leads. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of external or implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator, a Holter monitor with skin electrodes or even a ventricular assist device power pack. 100K illustrates the insertion of an external probe or catheter. These probes can be inserted into the femoral artery, for example, or in any other number of locations in the human body. Referring once again to element 100C, the cardiac pacemaker could also be any type of biologic data recording device. This would include loop recorders or the like. Referring once again to FIG. 1, 100I is described as an implantable defibrillator. It should be noted that these could be defibrillators with either endocardial or epicardial leads. This also includes a new family of subcutaneous defibrillators. In summary, as used herein, the term AIMD includes any device implanted in the human body that has at least one electronic component.

Figure 2:
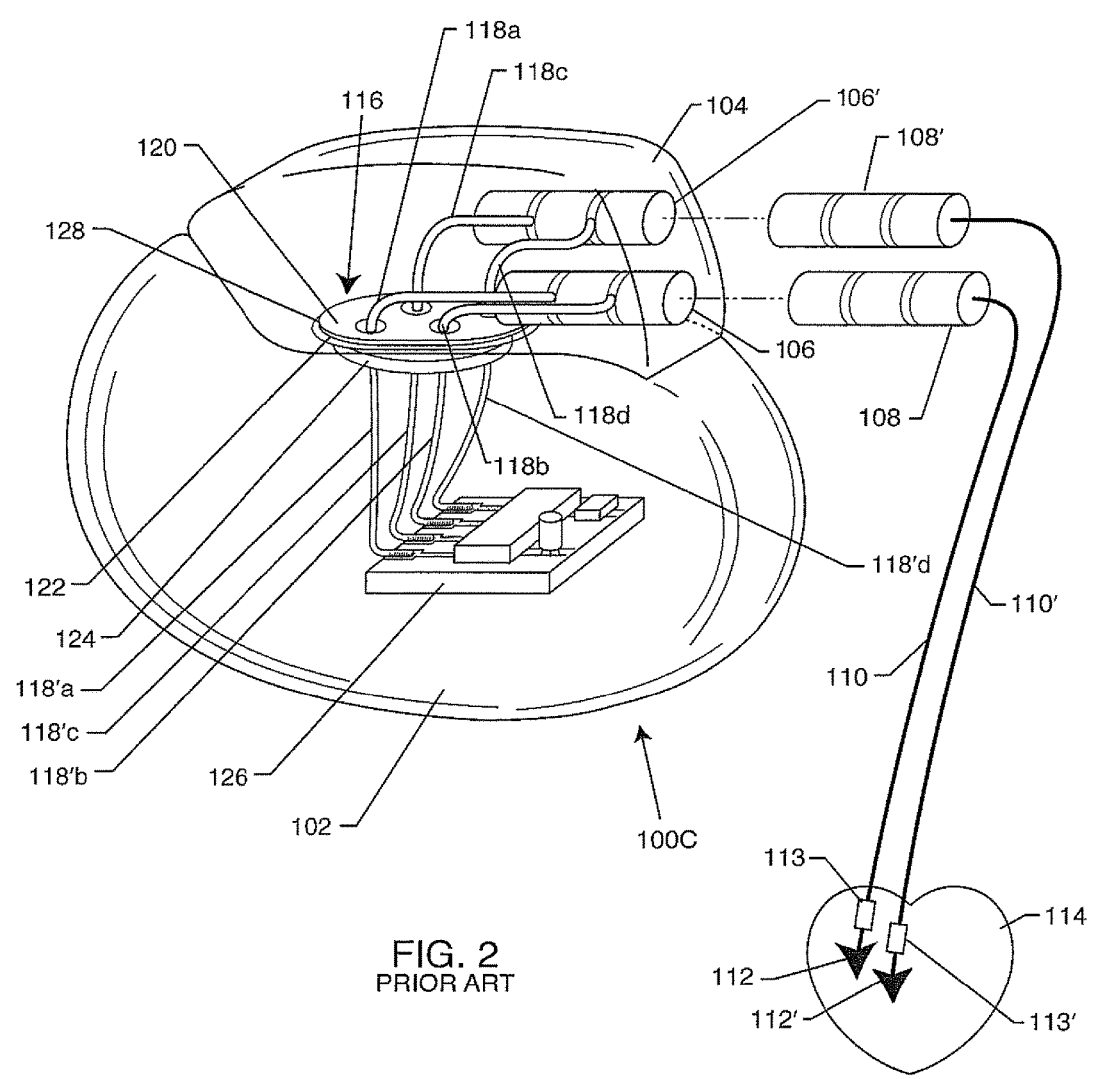
FIG. 2 is a side view of a prior art cardiac pacemaker.

FIG. 2 illustrates a prior art cardiac pacemaker 100C showing a side view. The pacemaker electronics are housed in a hermetically sealed and conductive electromagnetic shield 102 (typically titanium). There is a header block assembly 104 generally made of thermal-setting non-conductive plastic, such as Tecothane®. This header block assembly 104 houses one or more connector assemblies generally in accordance with ISO Standards IS-1, IS-2, or more modern standards, such as IS4 or DF4. These header block connector port assemblies are shown as 106 and 106'. Implantable leadwires 110, 110' have proximal plugs 108, 108' and are designed to insert into and mate with these header block connector cavities 106 and 106', or, in devices that do not have header block assemblies built directly into the pulse generator itself.

As used herein, the term "lead" refers to an implantable lead containing a lead body and one or more internal lead conductors. A "lead conductor" refers to the conductor that is inside of an implanted lead body. The term "leadwire" refers to wiring that is either inside of the active implantable medical device (AIMD) housing or inside of the AIMD header block assembly or both. Furthermore, as used herein, in general, the terms lead, leadwire and pin are all used interchangeably. Importantly, they are all electrical conductors. This is why, in the broad sense of the term, lead, leadwire or pin can all be used interchangeably since they are all conductors. Additionally, AIMD, as defined herein, includes electronic circuits disposed within the human body that have a primary or secondary battery, or have an alternative energy source, such as energy induced by motion, thermal or chemical effects or through external induction. As used herein, the term "header block" is the biocompatible material that attaches between the AIMD housing and the lead. The term "header block connector assembly" refers to the header block including the connector ports for the leads and the wiring connecting the lead connector ports to the hermetic terminal subassemblies which allow electrical connections to hermetically pass inside the device housing. It is also understood by those skilled in the art that the present invention can be applicable to active implantable medical devices that do not have a header block or header block connector assemblies such as pulse generators.

As used herein, the definition of electrically connected or electrical connection or conductively connected is defined to mean electrically connected by physical contact via a conductive medium that passes a broad spectrum of frequencies, including direct current. In this context, it will be understood that electrical connections can be made via numerous types of physical (direct or indirect) connections, such as through conductive adhesive, solder, conductive brazes, circuit board traces or circuit board plates, through leadwires and the like.

Figure 3:
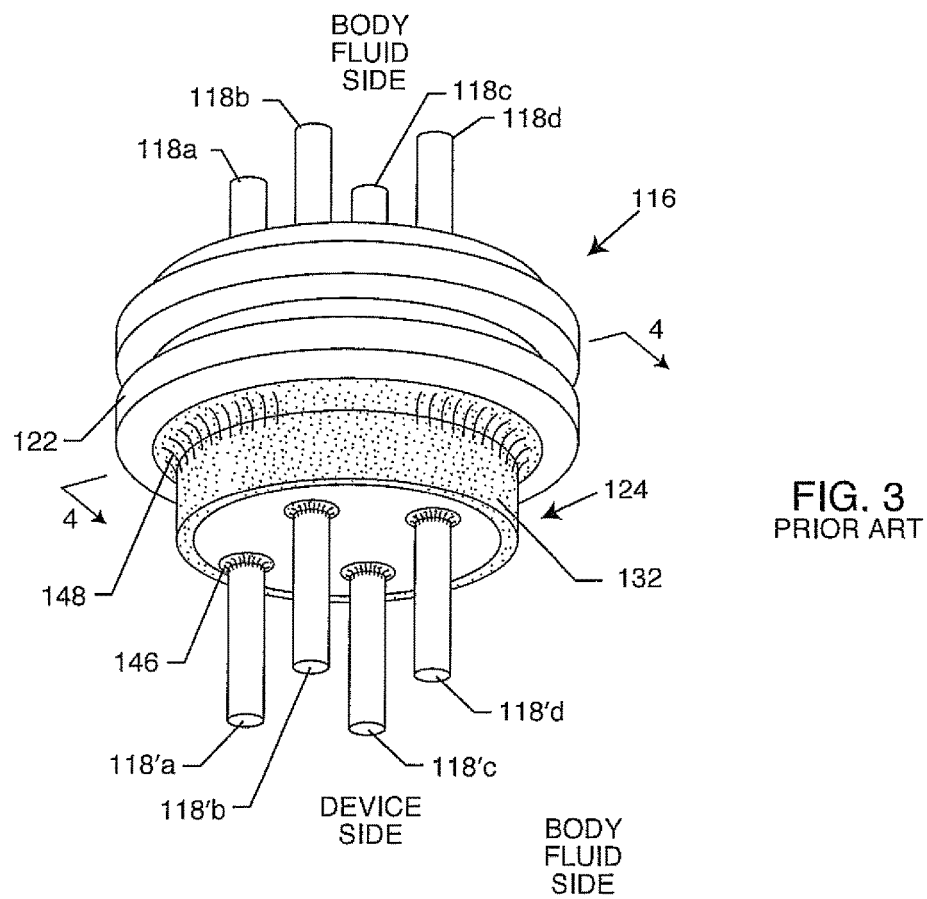
FIG. 3 is a perspective view of a quadpolar feedthrough capacitor and hermetic terminal assembly.

FIG. 3 illustrates a quadpolar feedthrough capacitor and hermetic terminal subassembly 116 where it has four leadwires 118a-118d and four feedthrough holes (quadpolar). It has a metallic ferrule 122 generally of titanium which is ready for laser welding into the AIMD housing 102 (not shown).

Figure 4:
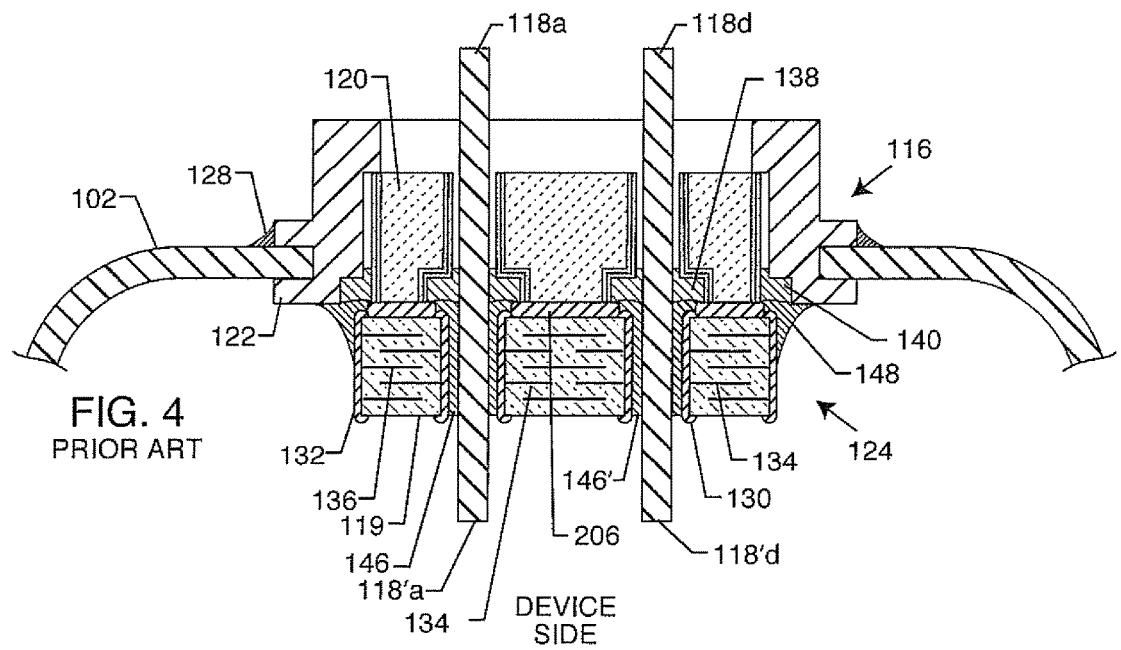
FIG. 4 is a sectional view of the feedthrough and hermetic terminal assembly of FIG. 3.

FIG. 4 is a prior art sectional view taken generally from section 4-4 from FIG. 3. This illustrates the hermetic terminal subassembly leadwires 118a-d passing through the hermetic terminal subassembly insulator 120 in non-conductive relationship and also through the feedthrough capacitor 124 wherein the active electrode plates 134 disposed within the capacitor dielectric 119 are electrically connected 146 to the hermetic terminal subassembly leadwire 118 and wherein the feedthrough capacitor ground electrode plates 136 disposed within the capacitor dielectric 119 are electrically connected 148 to the hermetic terminal subassembly ferrule 122 and gold braze 140. Referring once again to FIGS. 3 and 4, in each case it is seen that the hermetic terminal subassembly leadwires 118a-d pass all the way through the entire structure, namely, the hermetic terminal subassembly 116 and the feedthrough capacitor 124. In general, these hermetic terminal subassembly leadwires 118a-d are electrically and mechanically continuous (single material) and pass through from the body fluid side to the inside of the device 100 housing 102. Because the hermetic terminal subassembly leadwires 118a-d pass through from the body fluid side to the inside of the device housing by way of header block connector assembly or the like, it is very important that these hermetic terminal subassembly leadwire 118 materials be both biocompatible and non-toxic. Generally in the prior art, these hermetic terminal subassembly leadwires are constructed of platinum or platinum-iridium, palladium or palladium-iridium, niobium or the like. Platinum-iridium is an ideal choice because it is biocompatible, non-toxic and is also mechanically very strong. The iridium is added to enhance material stiffness and to enable the hermetic terminal subassembly leadwire to sustain bending stresses.

Figure 4A:
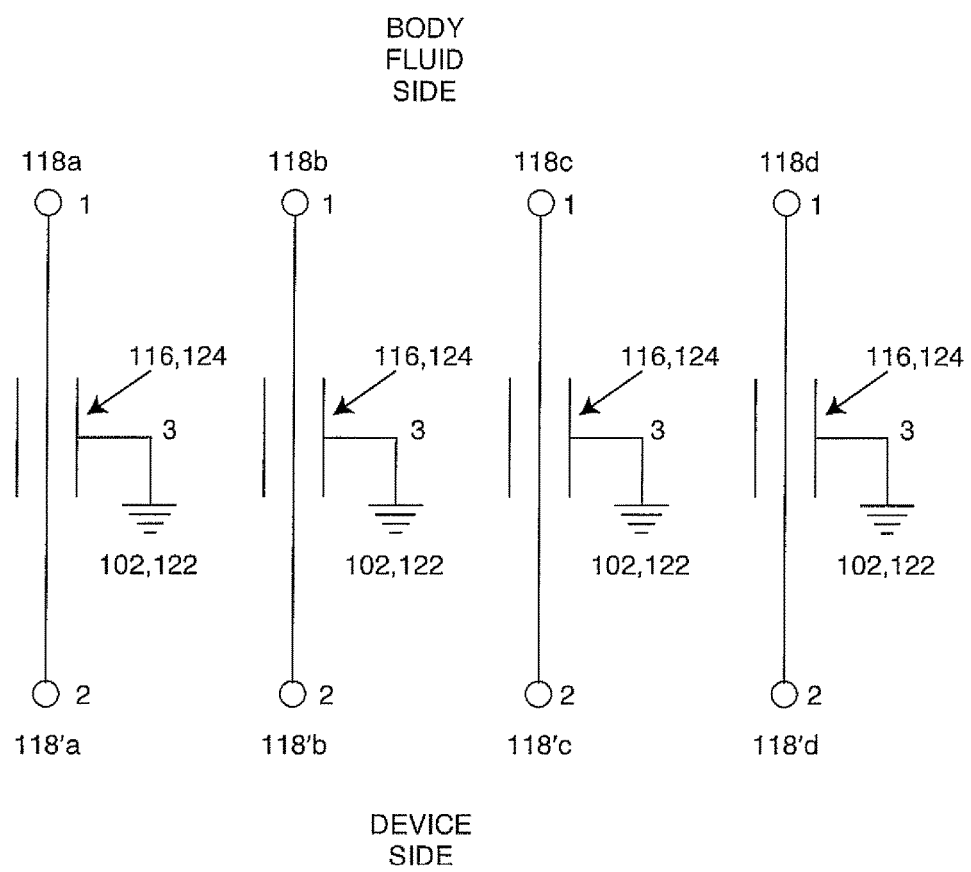
FIG. 4A is an electrical schematic representation of the quadpolar filtered feedthrough assembly as previously illustrated in FIGS. 3 and 4.

FIG. 4A is an electrical schematic representation of the quad polar filtered feedthrough assembly 116, 124, as previously illustrated in FIGS. 3 and 4. Referring once again to FIG. 4A, one can see that these are feedthrough capacitors and are three-terminal devices. For example, feedthrough capacitor 116, 124 has a first terminal 118a, a second active terminal 118'a and a ground terminal 102, 122. In the art, feedthrough capacitors are known as broadband low pass filters. They have practically zero series inductance and are desirable in that, they work over a very wide range of frequencies. In general, feedthrough capacitors and their internal electrode geometries are well known in the prior art. One is referred to U.S. Pat. Nos. 4,424,551; 5,333,095; 5,978,204; 6,643,903; 6,765,779 all of which are incorporated herein by reference.

FIGS. 5, 6 and 7 illustrate an internally grounded prior art feedthrough capacitor. In general, internally grounded feedthrough capacitors are known in the prior art with reference to U.S. Pat. Nos. 5,905,627; 6,529,103; 6,765,780 and the like, all of which are incorporated herein by reference. Referring once again to FIG. 5, one can see an internally grounded feedthrough capacitor, which is octapolar (eight active leads). The eight active leads are labeled 118a through 118h on the body fluid side and on the inside of the AIMD housing they are labeled 118'a through 118'h. The ferrule 122 has a peninsula structure 139, which is connected to an internal ground pin 118gnd. Referring now to the octapolar feedthrough capacitor active electrode plates 134, they are designed to overlay in a sandwich fashion the ground electrode plates 136. One skilled in the art will realize that one can stack up as many of these interleaved layers as is required in order to achieve the required capacitance value and other design factors. The internal ground lead 118gnd is electrically connected to the ground electrode plate layers 136. The active electrodes 134a through 134h are each electrically connected through their respective leadwires 118'a through 118'h. The overlap between the active electrodes 134 and the ground electrodes 136 create what is known as effective capacitance area (or ECA). The active and ground electrode layers may be interleaved with additional ceramic layers to build up the dielectric thickness (not shown). In general, the monolithic ceramic feedthrough capacitor 124, as shown in FIG. 6 as element 124, is a result of laminating the various electrode layers together and then sintering them at a high temperature to form a rigid monolithic ceramic block. This is known as a single feedthrough capacitor that is multipolar (in this case these are octapolar or eight active filtered circuits). One can see that there is a perimeter metallization 132 on the outside of the round capacitor i.e. FIG. 3 whereas, in this case in FIG. 6, there is no diameter metallization 132 at all.

There are several major advantages to internal grounding and removal of the perimeter or diameter metallization 132. This is best understood by referring back to FIGS. 3 and 4. Contrary to FIG. 4, with internal grounding there is no longer a need to apply a diameter metallization 132 as shown in FIGS. 5, 6 and 7. In addition, the electrical connection 148 has been entirely eliminated between the capacitor diameter metallization 132 and the gold braze 140 and ferrule 122. The elimination of this electrical connection 148 also makes the capacitor structure 124 much more resistant to mechanical damage caused by subsequent laser welding 128 of the hermetic seal assembly 116 into the AIMD housing 102. A significant amount of heat is produced by laser welding 128 and there is also a mismatch in thermal coefficient of expansion materials. By elimination of the electrical connection material 148, the capacitor 124 is free to float and is therefore, much more resistant to such stresses. Referring once again to FIG. 6, one can see that the internal ground lead 118gnd makes a low impedance connection from the capacitor's internal electrode plates 136 to the ferrule 122. This is what eliminates the need for the electrical connection material 148, as previously illustrated in FIG. 4. It will be appreciated that only one ground pin is shown in FIG. 6, but some designs may require a multiplicity of ground pins spaced apart such that, there is a very low impedance connection that will operate at low frequencies, effectively grounding the capacitor internal electrodes 136 at multiple points.

Referring once again to FIG. 6, one can see the ceramic capacitor subassembly 124 ready to be installed onto the hermetic terminal subassembly 189. These are shown joined together in FIG. 7 resulting in a hermetically sealed feedthrough capacitor filter assembly 116.

Referring back to FIG. 6, it is important to clarify some confusion as terms of art. The feedthrough capacitor 124 can also be described as a three-terminal feedthrough capacitor with multiple via holes or feedthrough holes. In a confusing manner, the hermetic terminal subassembly 189 is often referred to in the art as a hermetic feedthrough. Therefore, we have the term feedthrough applying both to the feedthrough capacitor and to the hermetic terminal assembly. As used herein, these are two separate and distinct subassemblies, which are joined together in FIG. 7 to become a feedthrough filter hermetic terminal assembly 116 ready for installation into an AIMD housing. Referring once again to FIG. 6, one can see that the internal ground lead 118gnd does not extend through to the body fluid side of the hermetic terminal feedthrough subassembly 189. It will be appreciated that it could be easily and readily extended to the body fluid side, but in most embodiments, it is not necessary.

An issue with the use of platinum for hermetic terminal subassembly leadwires 118a-d is that platinum has become extremely expensive and may be subject to premature fracture under rigorous processing such as ultrasonic cleaning or application use/misuse, possibly unintentional damaging forces resulting from Twiddler's Syndrome. Accordingly, what is needed is a filtered structure like a feedthrough capacitor assembly 116 which eliminates these high-priced, platinum, platinum-iridium or equivalent noble metal hermetic terminal subassembly leadwires 118. For additional examples of hermetic terminal subassemblies with feedthrough capacitors that employ leadwires 118, one is referred to U.S. Pat. Nos. 5,333,095, 5,896,267, 5,751,539, 5,905,627, 5,959,829, 5,973,906, 6,008,980, 6,159,560, 6,275,379, 6,456,481, 6,529,103, 6,566,978, 6,567,259, 6,643,903, 6,765,779, 6,765,780, 6,888,715, 6,985,347, 6,987,660, 6,999,818, 7,012,192, 7,035,076, 7,038,900, 7,113,387, 7,136,273, 7,199,995, 7,310,216, 7,327,553, 7,489,495, 7,535,693, 7,551,963, 7,623,335, 7,797,048, 7,957,806, 8,095,224, 8,179,658 the contents of all of which are incorporated herein by reference.

Figure 7A:
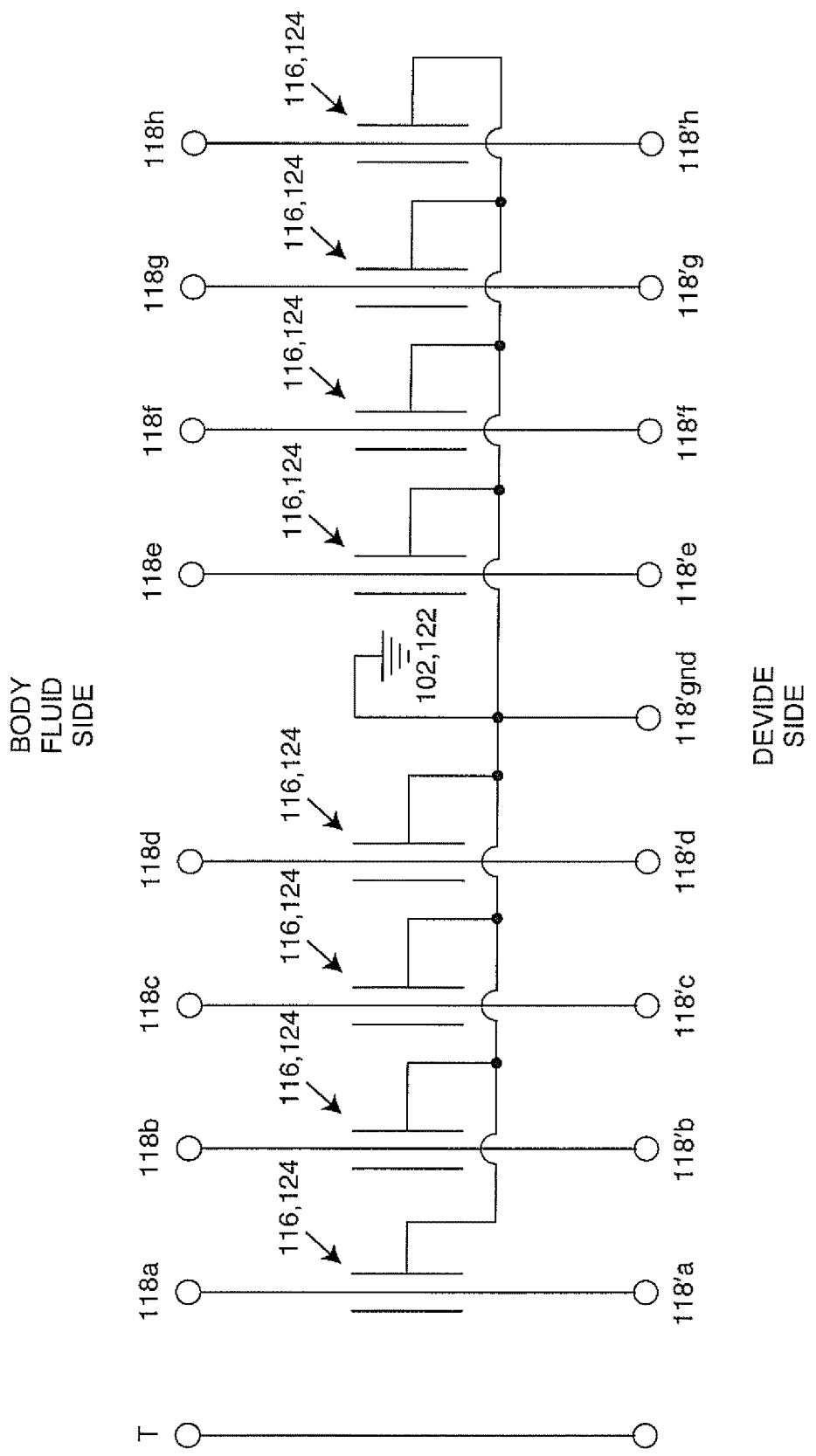
FIG. 7A is the electrical schematic for the feedthrough filtered hermetic terminal previously described in FIGS. 5, 6 and 7.

FIG. 7A is the prior art electrical schematic for the feedthrough filtered hermetic terminal 116 previously described in FIGS. 5, 6 and 7. Referring once again to FIG. 7A, one can see the telemetry pin T, which passes through the filtered hermetic terminal assembly 116 without any appreciable capacitance to ground. In other words, it would be undesirable to have any high frequency filtering of the telemetry terminal since this would preclude the ability to recover stored information or program the AIMD device remotely. Leadwires 118a through 118h all have feedthrough capacitor hermetic terminal assemblies 116, 124 as shown. The internal ground pin 118gnd is shown only on the device side of the hermetic terminal subassembly 189. Referring once again to FIGS. 5, 6, 7 and 7A, it will be noted that the feedthrough filter hermetic seal subassembly has been inverted with reference to FIGS. 2, 3 and 4. It should also be noted that the capacitor 124 is still on the device side; it's just drawn inverted.

Figure 8:
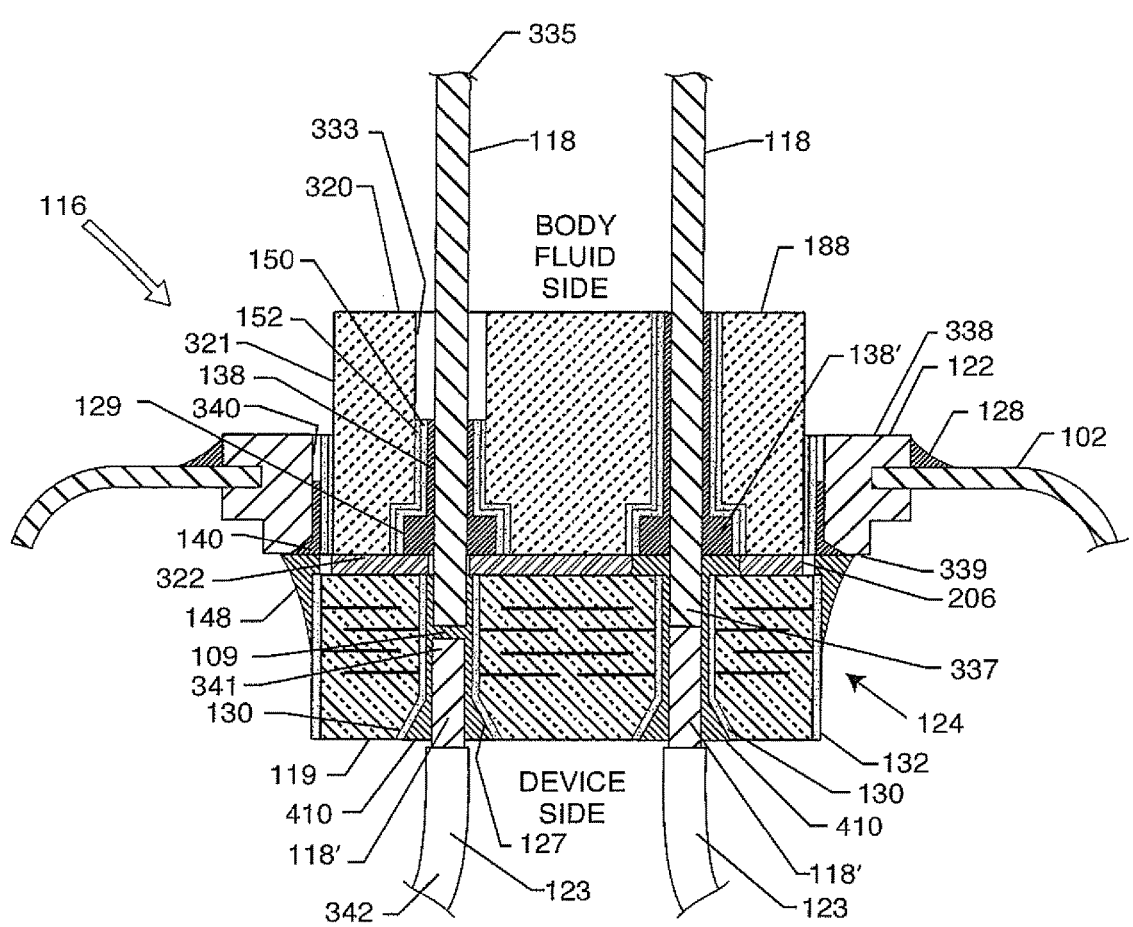
FIG. 8 is a sectional view of an exemplary filtered feedthrough of the present invention now showing a conductive leadwire extending through the hermetic seal into the device side with a pin joint captured by a feedthrough capacitor.

FIG. 8 illustrates a body fluid side leadwire 118, which is generally routed to an implantable leadwire, including one or more distal tip electrodes. Leadwire 118 could also be routed through a connector block on the body fluid side wherein, implantable leadwires may be plugged in. The body fluid side leadwire 118 passed through the insulator 188 of the hermetic terminal subassembly 189. As can be seen, the leadwire extends on the device side partial through feedthrough capacitor 124. A low cost leadwire 118' is inserted into the feedthrough capacitor via (or feedthrough holes) and are butted up to the device side leadwires 118 or placed adjacent the device side leadwires 118 as shown on the left hand side of FIG. 8. The device side leadwire 118 may comprise a number of different materials, but in general, they must all be biocompatible, non-toxic and biostable. Leadwire materials include platinum, palladium, tantalum, niobium, titanium, alloys containing iridium, or alloys of any of the materials listed above. Referring back to FIG. 8, one can see that the body fluid side leadwire 118 is physically and electrically attached to the tow cost device side leadwire 118' within an electrical connection 410 made within the feedthrough capacitor via holes. As defined herein, it will be appreciated that a feedthrough capacitor via hole is the same as a feedthrough capacitor feedthrough hole. In both cases, the feedthrough hole is a passageway wherein, one or more leadwires pass through the feedthrough capacitor. In fact, this is why it is called a feedthrough capacitor. Electrical attachment material 410 is preferably a high temperature solder. Two commonly available solders would be AG1.5, which consists of 97.5% lead, 1% tin and 1.5% silver. Another acceptable solder is SN10, comprising 10% tin, 88% lead and 2% silver. It will also be appreciated that material 410 could be a low temperature braze or it could be a thermal-setting conductive adhesive. As shown on the left hand side of FIG. 8, leadwire 118' is co-attached with electrical attachment 410 to device side leadwire 118. The feedthrough capacitor 124 is attached to the hermetic seal insulator 188 using an insulator 206. Insulator 206 can be of a variety of materials, including adhesive-backed polyimide washers. On the left hand side of FIG. 8, the insulator 206 has a very small diameter hole thereby preventing electrical material 410 from contacting gold braze material 138 in the counter bore area 129 of the hermetic seal that is formed between leadwire 118 and the insulator 188. This is fine if the leadwire 118 on the body fluid side is generally of non-oxidized and solderable materials, such as platinum, palladium or the like. However, if the device side leadwires are of lower cost materials, such as niobium or tantalum, those materials generally are not solderable and are heavily oxidized thereby, making it difficult without welding to achieve a good low impedance, low resistance electrical connection. This problem is readily solved by the embodiment of FIG. 8 shown on the right hand side wherein, the insulative washer 206 has a much larger hole thereby, allowing electrical contact material 410 to directly contact the gold braze material 138'. Therefore, the electrical connection between the capacitor active electrode plates to its inside diameter via hole metallization 130 is accomplished, not by an electrical attachment at all to the device side leadwire 188, but to the gold braze 138', which provides a non-oxidized and highly noble surface. During the gold braze operation, which forms the hermetic seal subassembly, the gold braze 138 would burn through any surface oxide and make a very low impedance metallurgical connection directly to the leadwire 118 itself. This is a very important embodiment in that, the leadwire of the body fluid side 118 can comprise very low cost materials as compared to platinum or palladium. One is also referred to U.S. Pat. No. 6,888,715, the contents of which are herein incorporated by reference.

Referring once again to FIG. 8, one can see that there is an adhesion layer 152 and a wetting layer 150 that have been applied to the inside diameter and outside diameter (or perimeter) of the alumina ceramic insulator 188. These are required because gold preforms generally will not wet or adhere to bare alumina insulators. The alumina insulator shown in FIG. 8 has been manufactured in a separate manufacturing operation and sintered and fired (as hard as a rock). Through sputtering processes, an adhesion layer is first laid down and then over that, a wetting layer 150 is laid down. This can also be done by some manufacturers in a single process, which combines wetting and adhesion properties into one (such as niobium). Other processes use a molybdenum adhesion layer and then a sputtered titanium layer to which gold will readily wet to. In summary, in order for the gold braze preforms 138 and 140 to properly flow and wet, there must first be layers sputtered onto the ceramic insulator, which will perform both adhesion and wetting characteristics. This will not be further described throughout this invention, but it will be appreciated that every time a gold braze is shown, that the adhesion/wetting layer is present. It will also be noted that on the outside diameter (when necessary) and inside diameter holes of the feedthrough capacitor 124, that there is a metallization 130. This can be a multilayer process, such as a copper and tin or copper and silver during an electroplating. The embodiment shown throughout this invention would be one of applying a silver or palladium-silver bearing glass frit, which is fired on as a single layer 130. It will be appreciated that the metallization 130 or capacitor 124 outside diameter or perimeter metallization 132 be shown throughout this invention as single layer (but as previously mentioned, it could consist of several different layers).

It will be appreciated that the machined ferrule 122, illustrated in FIG. 8, could also be replaced by a stamped ferrule or even a two-piece ferrule, as taught in U.S. Pat. Nos. 8,927,862; 9,431,814; and 8,604,341; and U.S. Patent Publications 2015/0245468 and 2016/0287883, the contents of all of which are incorporated herein by reference. Referring once again to FIG. 8, the machined ferrule 122 is relatively expensive, not just because of the machining process, but because the machining starts with a solid block of titanium and there is a great deal of scrap produced. A stamped metal ferrule or a two-piece stamped ferrule thereby, significantly reduces the machining costs and also results in a material savings. It will be understood that any of the machined ferrule in this teaching could be replaced with stamped ferrules in accordance with the referenced patents and publications.

Referring once again to FIG. 8, it will be appreciated that the device side leadwire 118' can be a solid wire, can be a stranded wire, can be a braided wire and the like. The advantage of stranded wires or braided wires is they are generally more resistant to shock and vibration load. Stranded or braided wires are also more flexible and more easily routed to internal circuit boards (not shown). At first glance, it would be appear from FIG. 8 that this is a bipolar (2) leaded device. However, it will be appreciated that this section could also represent a section taken from prior art FIG. 3 (quadpolar), a section taken from prior art FIG. 7 (octapolar) or the like. In other words, the bipolar device of FIG. 8 is for illustrative purposes only. It will be appreciated that any number of active leadwires 118 may be embodied. It will also be appreciated that telemetry pins T, as illustrated in FIGS. 5, 6 and 7, may also pass through the insulator structure 188. Such telemetry pins would not be associated with any feedthrough capacitor active electrode plates as it would be undesirable to attenuate high frequencies on a high frequency RF telemetry circuit. It will be appreciated in all of the drawings of this patent, that the principles are applicable to any number of active pins 118 or telemetry pins T.

Figure 9:
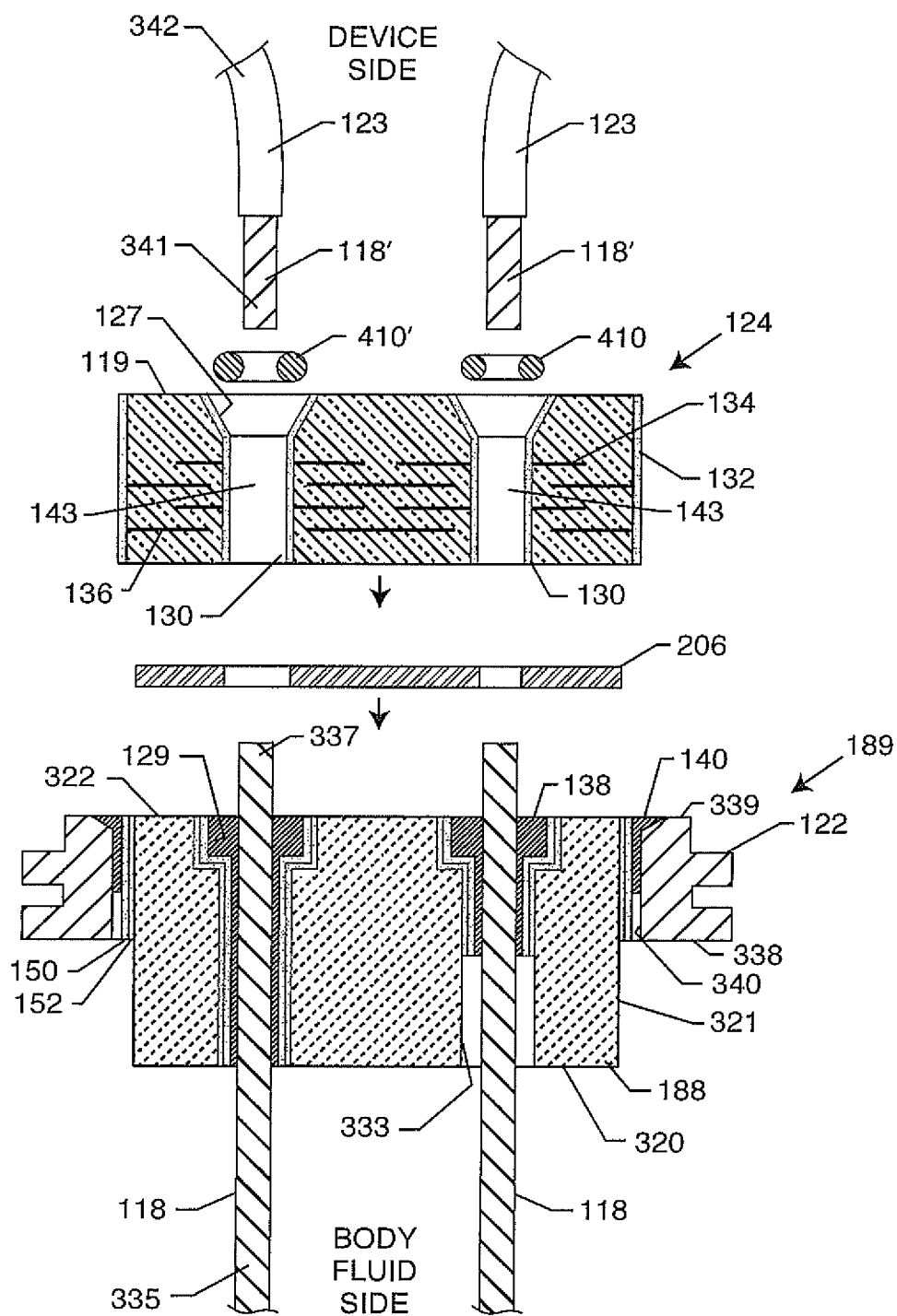
FIG. 9 is an exploded sectional view of the structure of FIG. 8 now shown upside-down for better understanding of the manufacturing steps.

As shown in FIG. 9, after the hermetic seal subassembly 189 is formed, the capacitor 124 is subsequently added. First, the insulator assembly 189 is inverted and an optional adhesive insulative washer 206 is placed. The capacitor 124 is disposed on top of the adhesive washer, which is then cured in an elevated temperature. This not only firmly and mechanically attaches the feedthrough capacitor 124 to the hermetic seal subassembly 189, but it also confines the area around the leadwire 118, such that a subsequent soldering operation cannot flow between the capacitor and the insulator, thereby, shorting out from lead to lead or lead to ferrule (ground). A low cost insulated (insulation 123 is optional) lead 118' is placed along with a solder preform 410. This is best illustrated in FIG. 9 where the hermetic seal subassembly 189 has been inverted and one can see the two leadwires 118 sticking up. The insulative washer 206 is then disposed over the leadwires 118 and the feedthrough capacitor 124 is placed adjacent the insulating adhesive washer 206. This is then pre-cured so they are firmly adhered and mechanically bonded together. During the curing of adhesive washer 206, it is usually required that a weighting or a spring fixture (not shown) be placed on the top (device side) of the feedthrough capacitor 124. This pushes the feedthrough capacitor firmly against the adhesive washer 206 and the surface of the insulator 188 so that they all bond together. Then, a solder preform 410 is placed into a counter-bore or counter-sink 127 in the device side surface of the feedthrough capacitor, as shown on the right. It will be noted that the left hand hole in insulator 206 is larger and also the solder preform 410' is also larger. This is so solder can flow, not only all the way through the feedthrough capacitor via hole (passageway) 143, but also all the way to contact gold braze material 138 of the hermetic seal subassembly 189. Next, a low cost leadwire, which is typically a tinned-copper leadwire 118', is placed through the solder preform 410 or 410'. The length of the conductive part of this leadwire 118' is chosen so that the low cost tin-copper leadwire will either touch or become very close to the leadwrire 118 of the hermetic insulator.

As best shown in FIGS. 8 and 9 and for clarity with the claims, the insulator substrate assembly 189 is comprised of the insulator body 188 which is defined as having a first insulator side (body fluid side) 320 opposite a second insulator side (device side) 322, the first insulator side and second insulator side separated and connected by at least one outside surface (outer perimeter surface) 321. At least one via hole 333 is disposed through the insulator body extending from the first insulator side to the second insulator side. A first conductive leadwire 118 has a first conductive leadwire first end 337 at least partially extending proud of the insulator surface 322 and having a first conductive leadwire second end 335 disposed past the first insulator side (body fluid side). The first conductive leadwire first end 337 is disposed near, at or adjacent to the second conductive leadwire first end 341. The first conductive leadwire 118 is also not the same material as the second conductive leadwire 118'.

The ferrule comprises a conductive ferrule body 122 defined as having a first ferrule side (boyd fluid ferrule side) 338 opposite a second ferrule side (device ferrule side) 339 and defining a ferrule opening 340 between and through the first and second ferrule sides.

The second (device side) conductive leadwire 118' has a second conductive leadwire first end 341 at least partially disposed within the first passageway of the feedthrough filter capacitor 124 and having a second conductive leadwire second end 342 disposed past the feedthrough filter capacitor. The second conductive leadwire second end 342 is configured to be connectable to electronics internal to the AIMD (not shown). Therefore, the first conductive leadwire second end 337 is at least partially disposed within the first passageway of the feedthrough filter capacitor, wherein the first conductive leadwire second end 337 is at, near or adjacent to the second conductive leadwire first end 341.

Figure 10:
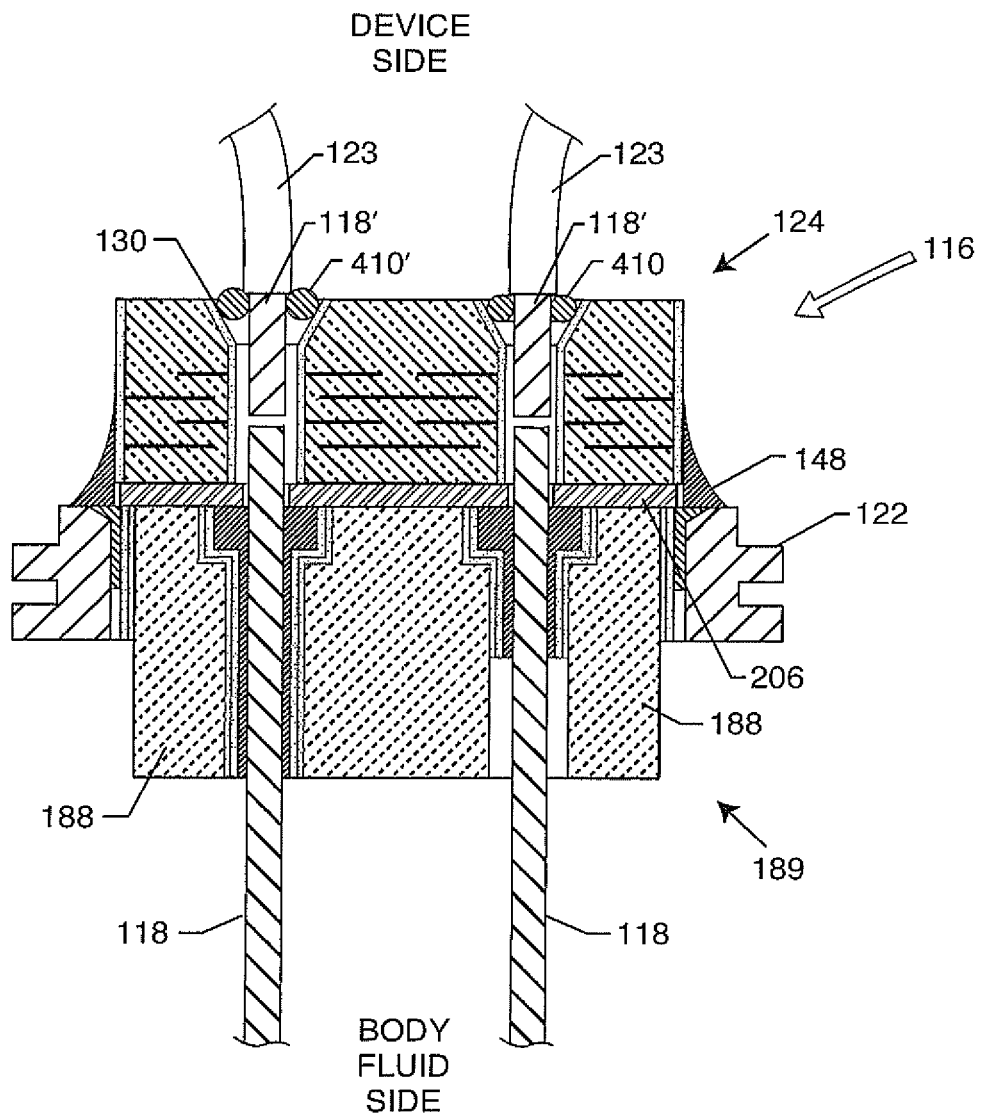
FIG. 10 illustrates the completed assembly of FIG. 9 prior to reflowing the solder preform.

FIG. 10 illustrates the completed assembly prior to reflowing the solder preform 410.

Referring now back to FIG. 8, one can see that the assembly 116 has been inverted in comparison to FIG. 10, but the solder preform 410, 410' has reflowed and is fully flowed around the tin-copper portion 118' of the low cost device side leadwire and also around the leadwire 118 from the hermetic seal subassembly 189. FIG. 8 increases the reliability of the wiring to the device side of the electronics through lead 118' with its optional insulation 123. As one can see, the reflow solder connection not only forms a butt joint between the low cost leadwire 118' and leadwire 118, but also the solder 410 flows all about both leads 118' and 118, thereby making the electrical connection not only a butt connection, but also a shear connection. It will be known to reliability engineers that solder joints that embody shear stresses will be more resistant to shock vibration, reflow and the like. Shear forces are also set up between the solder 410, 410' and the inside diameter of the capacitor feedthrough hole metallization 130. This double shear increases the mechanical strength of the attachment of the low cost leadwire 118' and also increases its pull strength force. It will also be appreciated that instead of a solder preform 410, 410', one could use a thermal-setting conductive adhesive, such as a conductive epoxy, low temperature braze or a conductive polyimide.

Referring back to FIG. 8, one can see that the solder (or equivalent material) 410, 410' has flowed all about the exposed end portion of the leadwire 118 and the low cost leadwire (tin/copper) 118'. As one can see, there is both a butt joint and a shear joint formed by solder flowing all around the outside diameters of both leadwire 118 and leadwire 118'. The choice of solders for making connection 410, 410' are somewhat limited in that, they need to have a relatively high melting temperature. This is because of the subsequent laser welding operation 128 wherein, the ferrule 122 is joined mechanically and hermetically to the AIMD housing 102. The laser welding operation 128 elevates the entire structure 116 to a fairly high temperature (approximately 260° C.). This results in a temperature rise, which causes electrical connection material 410, 410' to be elevated to temperatures as high as 220° C. The inventors have also seen applications where this electrical connection material may be elevated by certain laser weld operations 128 to as much as 260° C. or even 270° C. This rules out the use of low temperature solders 410, 410', which would have melting points below these temperatures. The reason for the variation in the maximum temperatures that the electrical connection 410 may be exposed to during laser welding 128 is that not all ferrule structures are the same and not all AIMD housing 102 are the same. In addition, some AIMD manufacturers use multiple pass laser welds and some use multiple pass laser welds 128. In other words, the maximum temperature of the material 410, 410' is application specific. There is another property of the overall assembly 116 that is imposed by the medical implant industry. This property is known as pull strength. During qualification, customers require pull strengths ranging anywhere from two to four, or even five pounds in range. This generally is done in a pull strength tester where the leads are put in tension. The inventors tested the assembly of FIG. 8 with two different high temperature solders 410, 410'. One, embodying SN10 and the other was using AG1.5. Both of these solders have reflow temperatures in the range of 290° C. The inventors performed various pull strengths and found that the pull strengths always exceeded two pounds and in many cases, depending on process control, exceeded seven pounds. Worse case experiments were run with the leadwires 118 and leadwires 118' not inside of a feedthrough capacitor. In other words, the two ends were joined just with solder and a certain amount of solder spread over the side walls. It was encouraging to note that in no case did the pull strength of these worse case assemblies, fall below two pounds. Subsequent testing in the inside diameter feedthrough capacitors generally showed pull strengths in the range of six to seven pounds. Accordingly, the inventors are satisfied that the novel arrangement as shown in FIG. 8, will meet both the pull strength, the high temperature, the shock and vibration, and the high temperature resistance requirements of the active implantable medical implant industry. Generally, the pull testing conducted by the experimenters placed a tinsel load on leadwires 118' until the point of failure.

Referring once again to FIG. 10, the solder preform 410, 410' desirably has a relatively high melting point. This is because the customer is subsequently going to perform a laser weld 128 as shown in FIG. 8. This laser weld 128 goes all around the circumference or perimeter of ferrule 122, which makes the electrical and mechanical and hermetic attachment between the ferrule and the AIMD housing 102. This creates a very significant heat pulse, as previously stated. It would be very undesirable if the electrical connection material 410, 410' reflowed during the customer laser welding application 128. Reflow of solder 410, 410' could cause the electrical conductive material, such as a solder to flow to undesired locations and even short out the interior of the active implantable medical device. Two preferred solders would be AG1.5 or SN10.

Referring once again to FIG. 8, one can see that the body fluid side, low cost leadwire 118 can have a gap 109 between it and the leadwire 118. This gap 109 is shown on the left-hand side of the figure. It will also be appreciated that between the device side leadwire 118', there may be a small gap 109 with the leadwire 118, as shown on the left, or the two may be butted directly against each other, as shown on the right. It should also be noted that the melted solder preform 410 picks up additional strength, not only because it is in shear around the circumference of leadwire 118 and leadwire 118', but it is also wetted to the inside feedthrough capacitor diameter metallization 130. It will be appreciated throughout the rest of this patent that the electrical connection material 410 will be referred to as a solder. The word "solder" shall be construed broadly to include thermal-setting conductive adhesives, low temperature brazes and various types of solder alloys. Accordingly, the solder preform 410 not only mates around leadwire 118 and 118', but it also wets completely to the ceramic capacitor 124 inside diameter of feedthrough hole metallization 130. This creates additional shear strength. This goes to facilitate the requirement in the industry that the device side leadwire have a very high pull strength. In general, pull strengths are specified generally between the range of 2 lbs. to 5 lbs. This is equally applicable to the body fluid side leads 118 and the device side leadwires 118'. Accordingly, it is very important that process controls ensure that the solder preform 410, 410' flows very evenly around both leadwire 118 and leadwire 118' and also properly wets the metallization 130 (without having it dissolve into the solder, a situation known in the industry as leaching). Ideally, it would preferable to be able to flow the solder preform 410, 410' without the use of fluxes. If one uses a flux, then one must perform cleaning steps to remove the flux. Accordingly, the assembly as illustrated in FIG. 8, is best accomplished either in a conveyor-type curtain soldering furnace or as a bulk process in a device called a DAP sealer. In both cases, the soldering can be accomplished by either reducing or inert gases, thereby eliminating the need for fluxes and also a temperature profile could be created where the relatively fragile ceramic capacitor 124 can be slowly heated up and the solder 410, 410' molten stage can be held to a relatively low amount of time and then the entire assembly is then slowly cooled down. It is desirable not to have the high temperature solder 410, 410' be molten for too long as the capacitor termination material 130 can actually dissolve or leach undesirably into solder 410, 410'.

Referring once again to FIG. 8, one can see that on the device side, the ceramic capacitor 124 has counter-sinks 127 to facilitate placement of the solder preform 410, 410'. This counter-sink is best viewed in FIG. 9, as element 127. Referring once again to FIG. 8, one can see that there are counter-bores 129 placed in the insulator 188 of the hermetic terminal subassembly 189. These allow for convenient placement of gold braze preforms (not shown).

Referring back to FIG. 8, it will be appreciated that the hermetic seal subassembly 189 comprises, in general, an alumina ceramic insulator 188 with sputtered surfaces that allow it to be gold brazed 138, 140 to both leadwires 118 and the ferrule 122. These gold brazes make both a physical and a hermetic seal between the insulator 188 and body fluid side leadwires 118. There is a second gold braze 140 between the ferrule 122 and the hermetic insulator 188. It will be appreciated that it is not necessary to have a gold brazed hermetic seal subassembly 189. It is known in the art that this could also be a glass seal. In other words, instead of being an alumina ceramic, insulator 188 can comprise a glass and a glass seal which is formed between the glass and leadwires 118 and at the same time, to the ferrule structure 122. It is also known in the art that these can be fusion or compression glasses comprising a number of materials, including borosilicates and the like. Referring once again to FIG. 8, one can appreciate that if the hermetic seal subassembly 189 is a glass sealed hermetic seal subassembly, then one no longer has a gold braze 138' to the leadwire 118. In the case where the leadwire 118 is a low cost niobium or tantalum leadwire (or equivalent materials), then it would be necessary to treat the proud portion 337 (that is proud of the device side or second surface of the hermetic seal insulator 188) such that the electrical attach material 410 can make proper electrical and physical contact with the leadwire 118. For example, if the leadwire 118 was of niobium or tantalum or even titanium, it would be necessary to treat the proud portion 337 with an electroplating, such as a gold plating, or sputtering operations, including a platinum or gold sputtering operation, such that proper electrical connection between the electrical connection 410, leadwire 118' and the proud portion 337 of leadwire 118 can be accomplished.

Now referring to FIG. 9, by focusing only on the bottom portion 189, which is the hermetic terminal subassembly. One can see that when the gold braze 138 is placed through gravitational and capillary action in the gold braze furnace, it will flow down and form the gold braze hermetic seal joint 138. Referring now to FIG. 8, the hermetic seal subassembly 189 has been inverted. Since the gold braze joints 138 and 140 have been formed at very high temperature, they will not be disturbed nor will they reflow during the subsequent capacitor 124 soldering operation 410, 410'. It is important to realize that in a typical manufacturing operation, the hermetic terminal subassembly 189 is manufactured in an entirely different manufacturing line with a different set of controls, including braze furnaces and the like. It is equally important to note that the feedthrough capacitor assembly 124 is generally performed in an entirely different manufacturing line (usually in Class 10,000 or better clean rooms). It is a monolithic device consisting of alternating layers of ground and active electrodes, which goes through a number of binder bake-out and then sintering operations. Subsequent to that, metallization layers 130 and outside diameter metallization layer 132 are applied, either by electroplating, by applying conductive glass frits (and firing) and the like. In the final operation shown in FIG. 9, the capacitor subassembly 124 is adhered by adhesive backed insulator 206 to the hermetic terminal subassembly 189 and at the same time, device-side leadwires 118' are co-joined.

Referring once again to FIG. 9, one can see that after the solder preform 410, 410' is reflowed, one still needs to make the electrical connection from the capacitor outside diameter perimeter metallization 132 to the ferrule 122 using electrical attachment material 148 as shown in FIG. 8. This attachment 148 could be performed prior to the solder reflow 410, 410' or after. In one embodiment, the electrical attachment material would be a thermally-conductive polyimide, which is cured around 290 to 300° C., but can withstand short-term temperatures up to 500° C. So in this case, the capacitor diameter or perimeter metallization would first be formed and then the solder preform 410, 410' would subsequently be reflowed at around 300° C. Referring back to FIG. 8, one can see that the electrical connection material 148 contacts gold braze surface 140, which provides an oxide-free, very low impedance electrical connection. One is referred to U.S. Pat. No. 6,765,779, the contents of which are incorporated herein by reference, which describes the importance of making an electrical connection to an oxide-free surface instead of to oxidized titanium surfaces.

FIG. 10 illustrates the capacitor 124 co-joined to the hermetic seal subassembly 189 by adhesive washer 206. The device side leads 118' have been placed through their solder preforms 410, 410'. FIG. 10 illustrates the entire assembly 116 just prior to reflow of the solder preform 410, 410'. After the solder preform 410 is reflowed at an elevated temperature, it will result in the structure 116, as illustrated in FIG. 8 (inverted). As can be seen, the solder preform 410, 410' flows all around the two leadwire 118, 118'.

Figure 11:
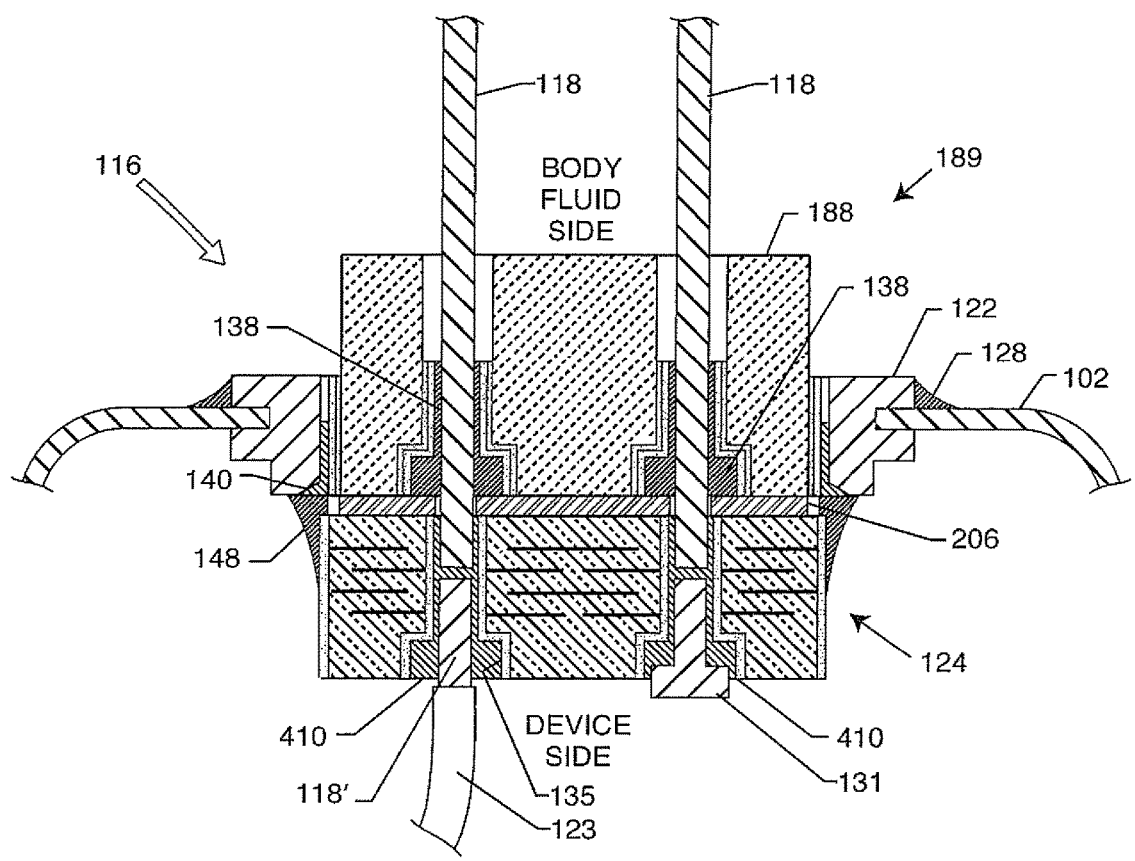
FIG. 11 is very similar to FIG. 8 except on the capacitor device side counter-bores are shown instead of counter-sinks and one of the leadwires may be a wire bond pad structure.

FIG. 11 is very similar to FIG. 8 except on the capacitor device side, counter-bores 135 are shown instead of counter-sinks 127. The right side of the device now has a wire bond pad 131 which may be proud of the feedthrough capacitor 124. This nail head 131 may be proud of the device side surface of the feedthrough capacitor 124 (as shown) or it may be flush with the surface (not shown), or it may be reduced below the surface (not shown), or it could be replaced with the wire attachment structures in FIGS. 41-48.

Figure 12:
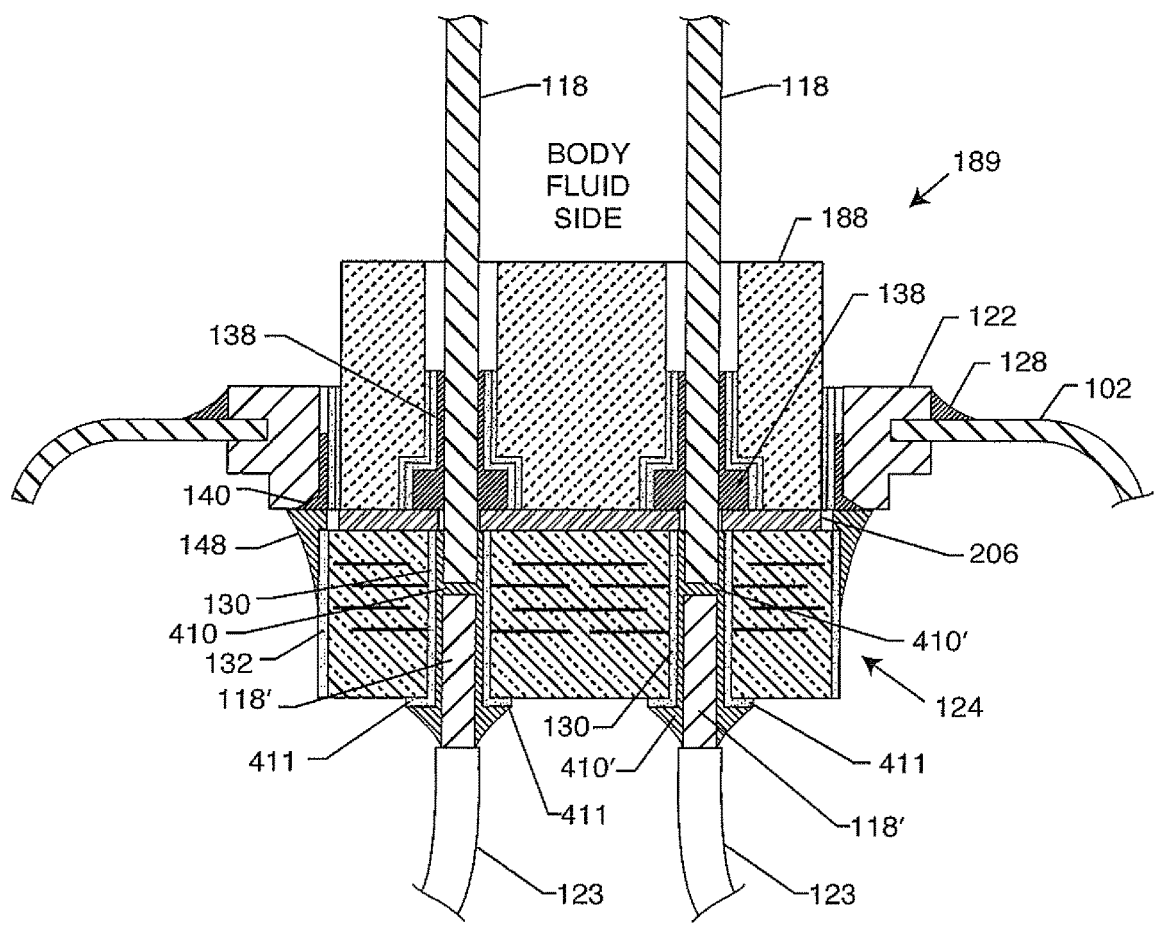
FIG. 12 is very similar to FIG. 8, except that the counter-sinks have been eliminated on both the right and the left side of the device side of the feedthrough capacitor.

FIG. 12 is very similar to FIG. 8, except that the counter-sinks 127 have been eliminated on both the right and the left side of the device side of the feedthrough capacitor 124. This will make it more difficult to place a solder preform 410, 410' and have it reflow properly. However, it will be understood by one skilled in the art that counter-bores, counter-sinks or combination and variations thereof can be used, or alternatively, as shown in FIG. 12 no such structures are used to help locate and place the solder preform 410, 410'.

Referring back to FIG. 12, one can see that the feedthrough capacitor inside diameter (or via hole) metallization 130 has been extended 411 onto the device side surface (extended onto the device side) of the feedthrough capacitor 124 such that it forms a circular portion, which is also known in the industry as a white-wall tire shape. As previously described, this metallization 130, 411 can be mechanically and electrically adhered to the capacitor electrode plates by firing a silver or palladium-silver glass frit, electroplating or the like. In all cases, the metallization 130, 411 firmly adheres to the body of the feedthrough capacitor 124. The presence of the white-wall tire metallization 411 allows for the solder 410 to form a fillet 410' between the lead conductor 118' and metallization band 411. This forms a solid fillet, which is known in the industry to have very high strength. In other words, the white-wall tire metallization 411 and corresponding solder (or thermal-setting conductive adhesive) filet adds greatly to the pull strength of the lead 118', 123.

Figure 13:
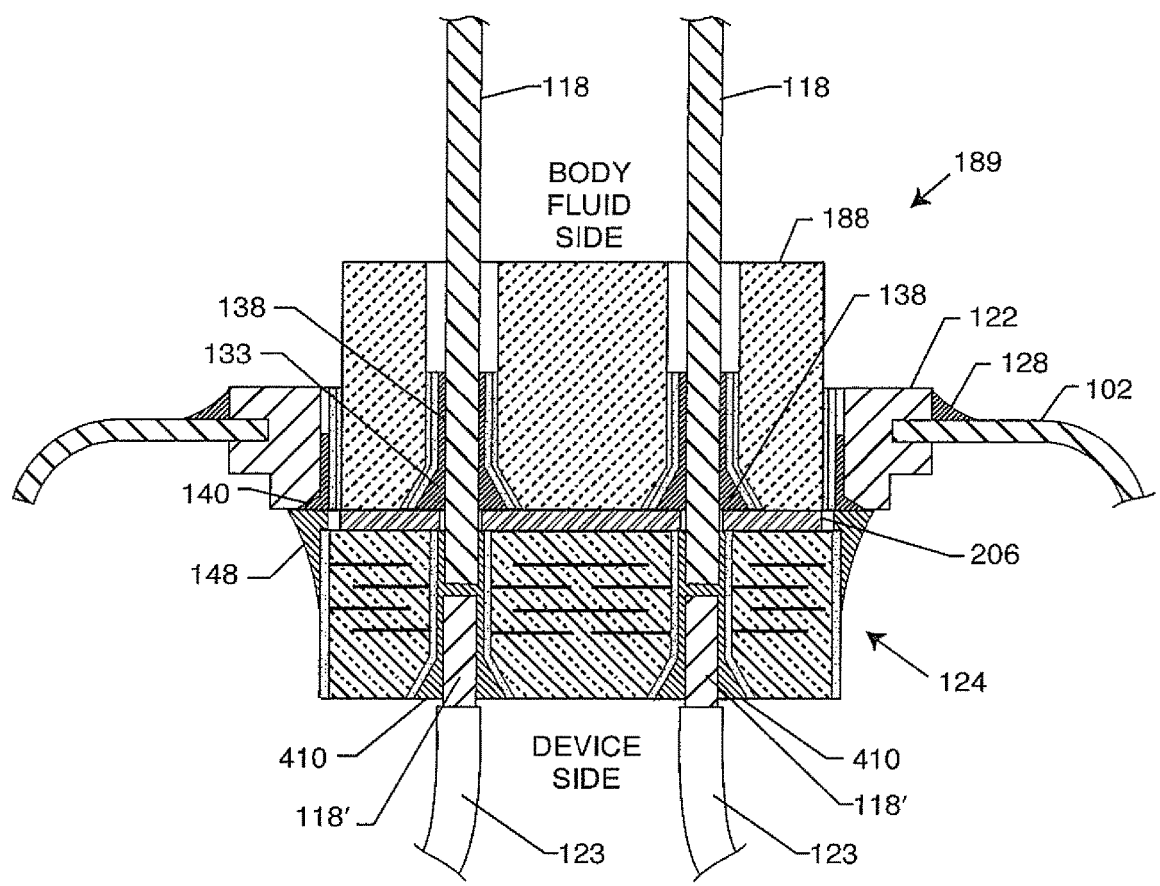
FIG. 13 is very similar to FIG. 8, except that in this case, the counter-bores on the device side of the hermetic insulator have been replaced by counter-sinks.

FIG. 13 is very similar to FIG. 8, except that in this case, the counter-bores on the device side of the hermetic insulator 188 have been replaced by counter-sinks 133.

Figure 14:
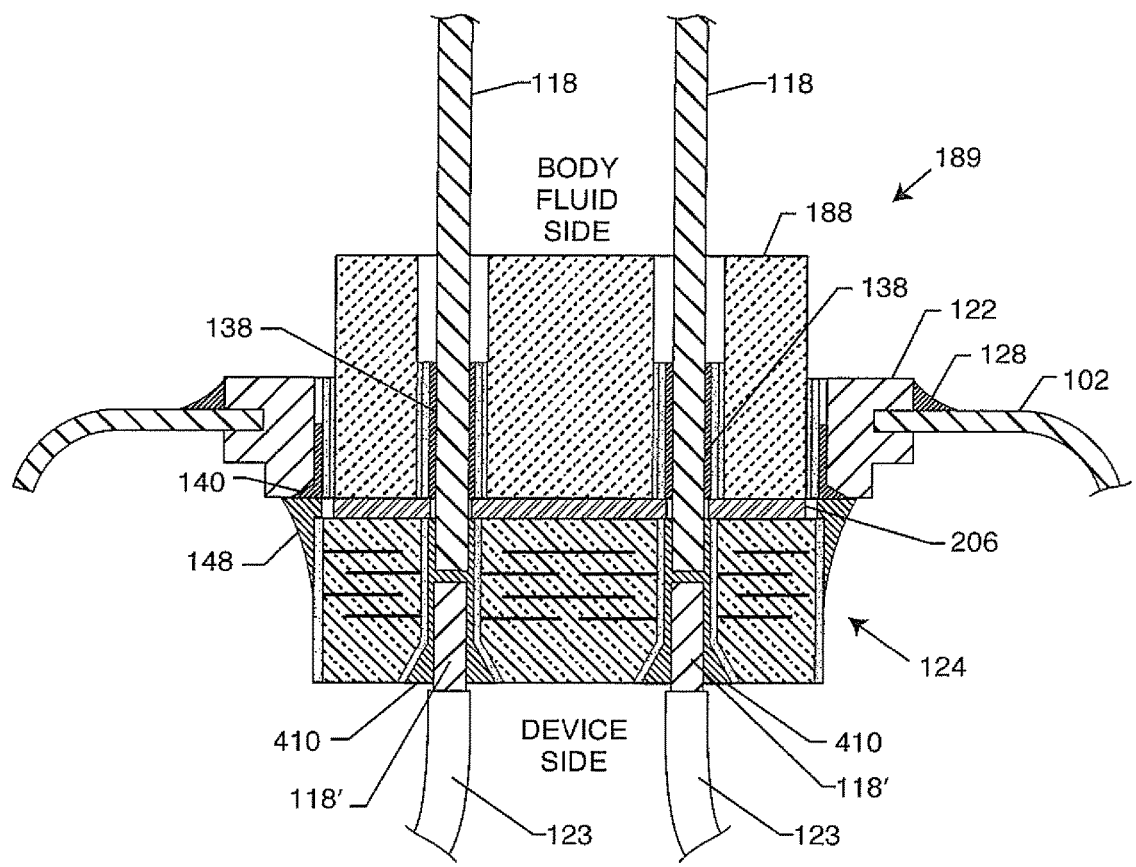
FIG. 14 is very similar to FIG. 8, except that the counter-bores in the alumina ceramic insulator have been removed.

FIG. 14 is very similar to FIG. 8, except that the counter-bores 129 in the alumina ceramic insulator 188 have been removed. This will make it more difficult to place gold brazed preforms 138 (not shown before brazing). Again, it will be understood by one skilled in the art that counter-bores, counter-sinks or combination and variations thereof can be used, or alternatively, as shown in FIG. 14 no such structures are used in the insulator 188 to help locate and place the gold brazed preforms 138 (not shown before brazing).

Figure 15:
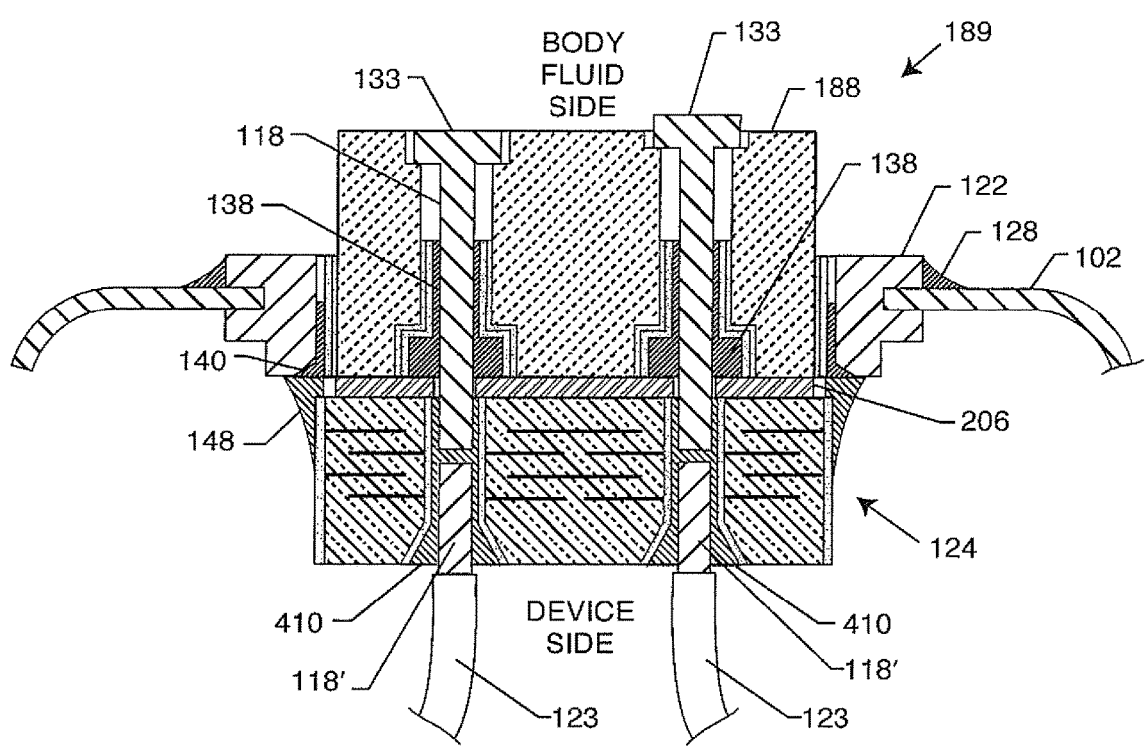
FIG. 15 is very similar to FIG. 8, except that the body fluid side leadwires have been replaced by biostable and biocompatible wire bond pads.

FIG. 15 is very similar to FIG. 8, except that the body fluid side leadwires 118 have been replaced by biostable and biocompatible wire bond pads 133. In a preferred embodiment, these pads are drawn from a single piece of wire 118, which extends down into the gold braze 138.

Figure 16:
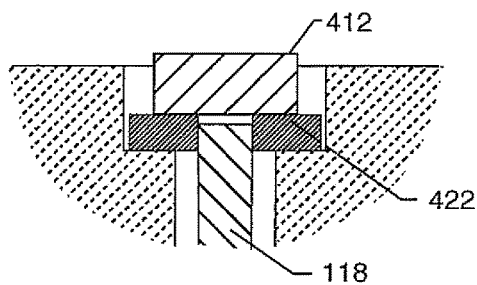
FIG. 16 illustrates an alternate method of manufacturing a nail-headed lead as previously described in FIG. 15.

FIG. 16 illustrates an alternate method of manufacturing a nail-headed lead 118 as previously described in FIG. 15. Instead of continuously drawing the nail head 133 as a continuous piece of the leadwire 118, FIG. 16 illustrates that the nail head 412 may be machined as a separate structure and then gold brazed 422 to the lead 118. Gold braze 422 would typically be a co-brazing operation at the same time gold brazes 138 and 140 are formed.

Figure 17:
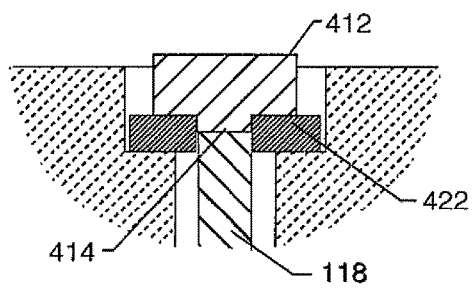
FIG. 17 illustrates that the nail head may be modified to have an elongated piece that engages the gold braze preform.

FIG. 17 illustrates that the nail head 410 may be modified to have an elongated piece that engages the gold braze preform. This aids in centering and aligning the nail head 412 with the lead 118.

Figure 18:
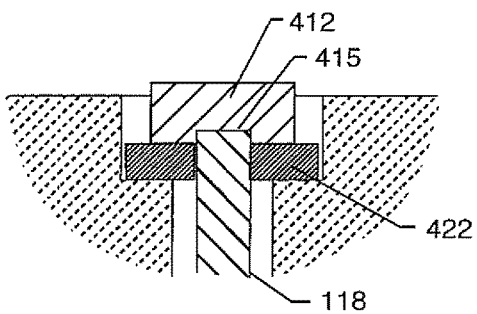
FIG. 18 illustrates that a counter-bore may be included within the machine nail head into which the lead protrudes.

In FIG. 18, one can see that a counter-bore may be included within the machine nail head 412 into which the lead 118 protrudes. Again, this helps with alignment during the gold braze flowing operation 422.

Figure 19:
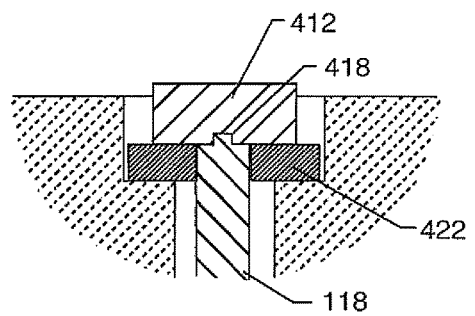
FIG. 19 is very similar to FIG. 18, except that in this case, the counter-bore and nail head is smaller and that a protrusion or extension is formed on the end of lead to engage counter-bore.

FIG. 19 is very similar to FIG. 18, except that in this case, the counter-bore and nail head 412 is smaller and that a protrusion or extension is formed on the end of lead 118 to engage counter-bore 418. Again, this is to help with maintaining alignment during the gold braze reflow operation 422.

Figure 20:
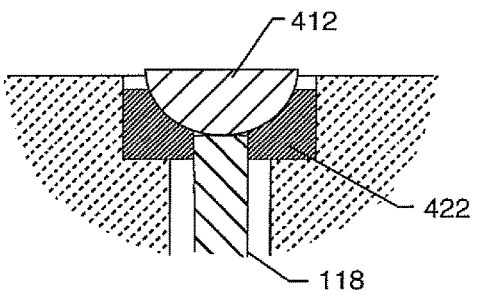
FIG. 20 illustrates that the nail head may have a semi-circular (or other) shape.
Figure 21:
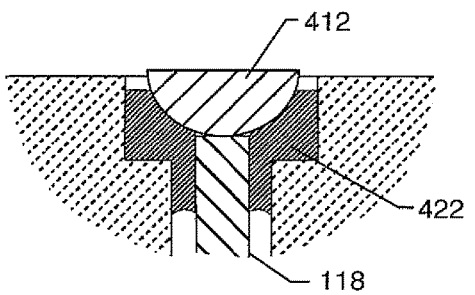
FIG. 21 illustrates that the contact area can be further increased by using a larger gold preform in comparison to FIG. 20.

FIG. 20 illustrates that the nail head 412 may have a semi-circular (or other) shape. The advantage of the semi-circular shape is that this increases the wetting and shear area to the gold braze 422 and also increases the gold braze contact area to the lead 118. This contact area can be further increased by using a larger gold preform 422, as illustrated in FIG. 21. Referring back to FIGS. 16 through 21, it will be appreciated that a weighting fixture (not shown) may be applied to the top of any of the nail heads or even an alignment fixture so that they are properly held in place during the gold braze reflow 422.

Figure 22:
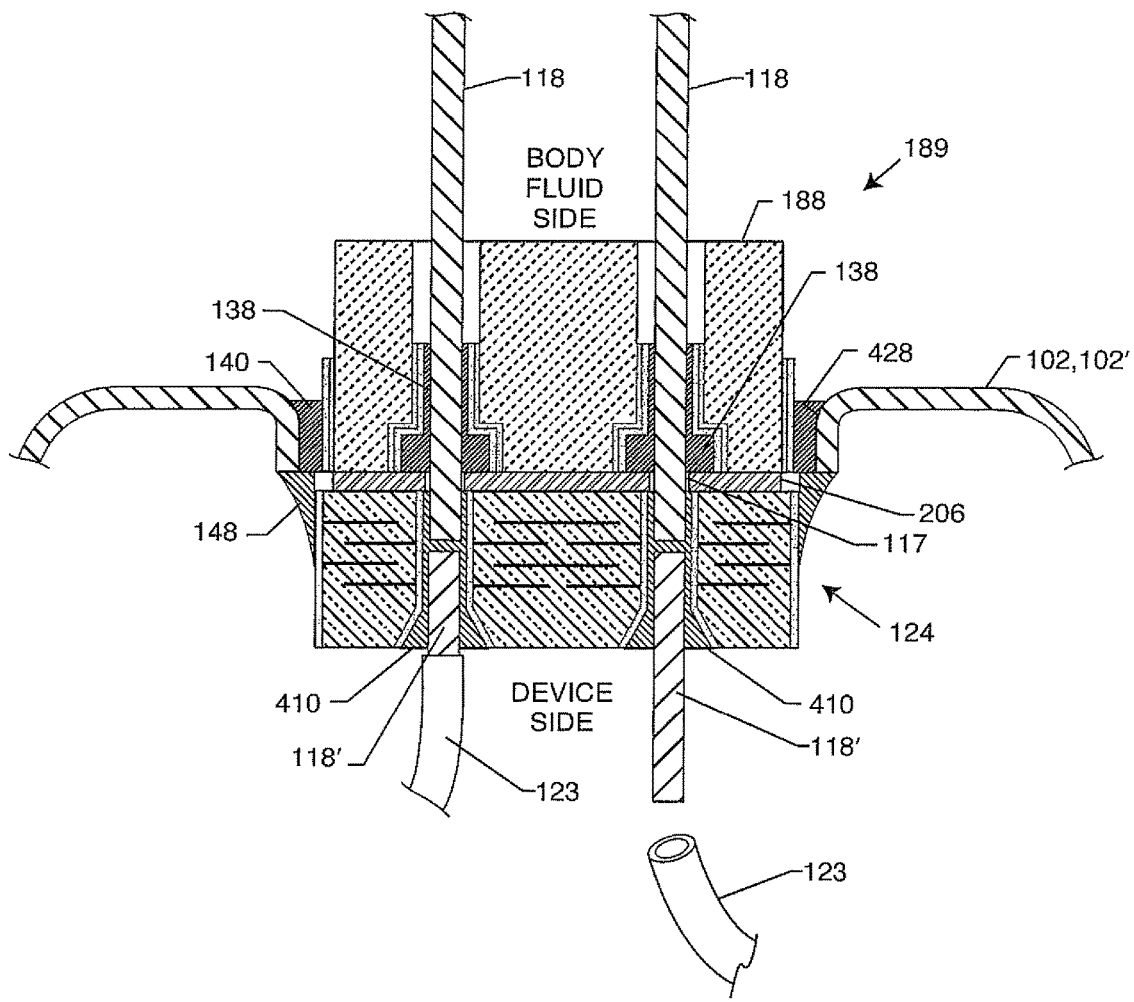
FIG. 22 is very similar to FIG. 8, except that now the ferrule structure has been completely eliminated.

FIG. 22 is very similar to FIG. 8, except that the ferrule structure 122 has been completely eliminated. By eliminating the ferrule, one eliminates a significant amount of cost. Typically, these titanium ferrules are machined out of a solid piece of titanium, which entails a substantial amount of machining time, labor and scrap. Referring to FIG. 22, one can see that the AIMD housing 102 has been bent down to form an aperture 428 into which the hermetic seal insulator 188 is aligned. The insulator 188 is then gold brazed 140 directly to the AIMD housing 102. This is actually co-brazed along with gold braze 138 as previously described. It will be appreciated that instead of gold brazing directly to the entire AIMD housing 102, the gold braze 140 may be done to a lid or a shield assembly, which is subsequently laser welded into the AIMD housing 102 (not shown). Referring once again to FIG. 22, one can see that on the left side, a low cost insulated leadwire 118' has been co-soldered 410 on the inside diameter of the feedthrough capacitor to leadwire 118. On the right hand side of FIG. 22, towards the device side, one can see an alternative low cost leadwire 118' wherein, the insulation 123 can be added later. It will be appreciated that the length of leadwire 118' can be of any suitable length to reach a circuit board or even provide for a stress-relieving or strain-relieving loop. The insulation 123 on the right side of FIG. 22 can be an insulation sleeve, an insulation tubing or even a heat-shrink tubing, which is added later. A preferred material would be an insulative tubing consisting of KAPTON.

Figure 23:
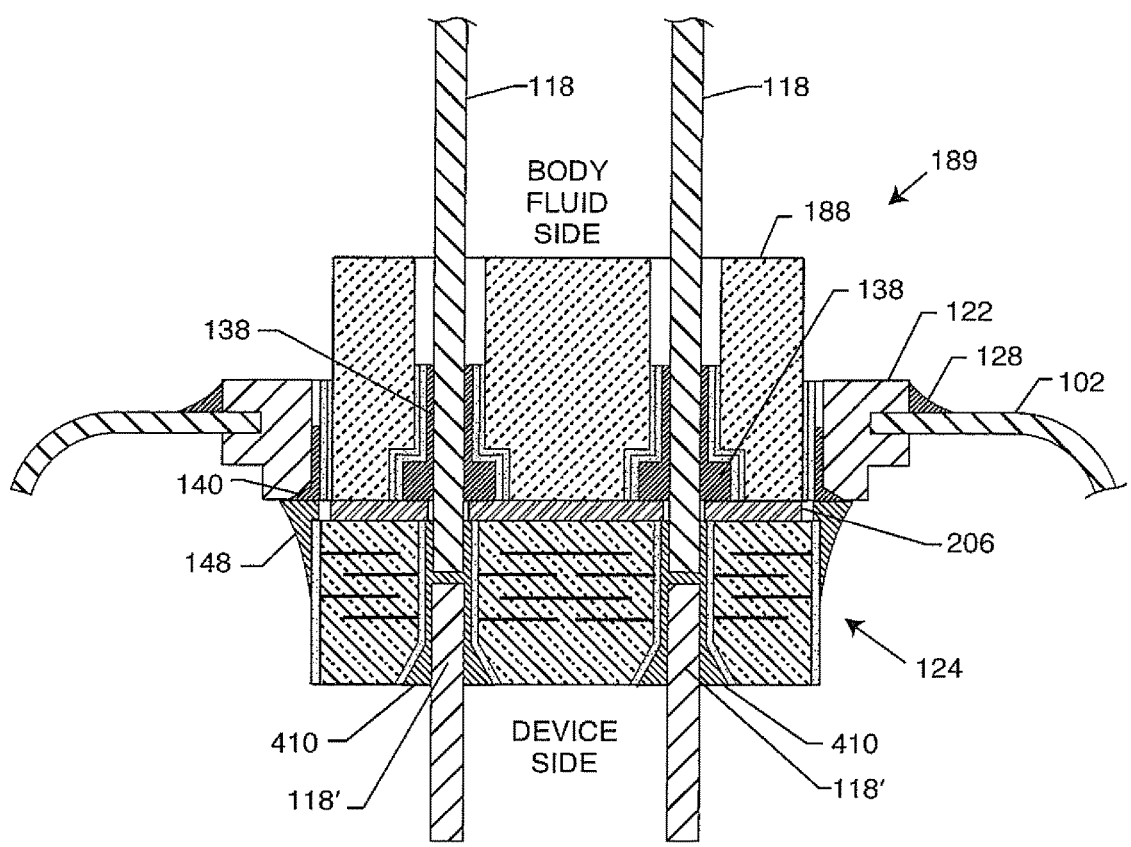
FIG. 23 is very similar to FIG. 8, except that the low cost leadwires, instead of being stranded, are solid wire stubs.

FIG. 23 is the same as FIG. 8, except that the low cost leadwires 118', instead of being stranded, are solid wire stubs. The lengths of these leadwire stubs 118' vary in length below the feedthrough capacitor 124 in accordance with the application. For example, if the customer was going to install a very thin flex cable to make the connection between leadwires 118' and a circuit board 126 (not shown), then the leadwires 118' need not stick out very far. However, if a circuit board was being placed adjacent the feedthrough capacitor 124 with via holes (not shown), then it might be necessary to make the leadwire stubs 118' a little longer.

Figure 24:
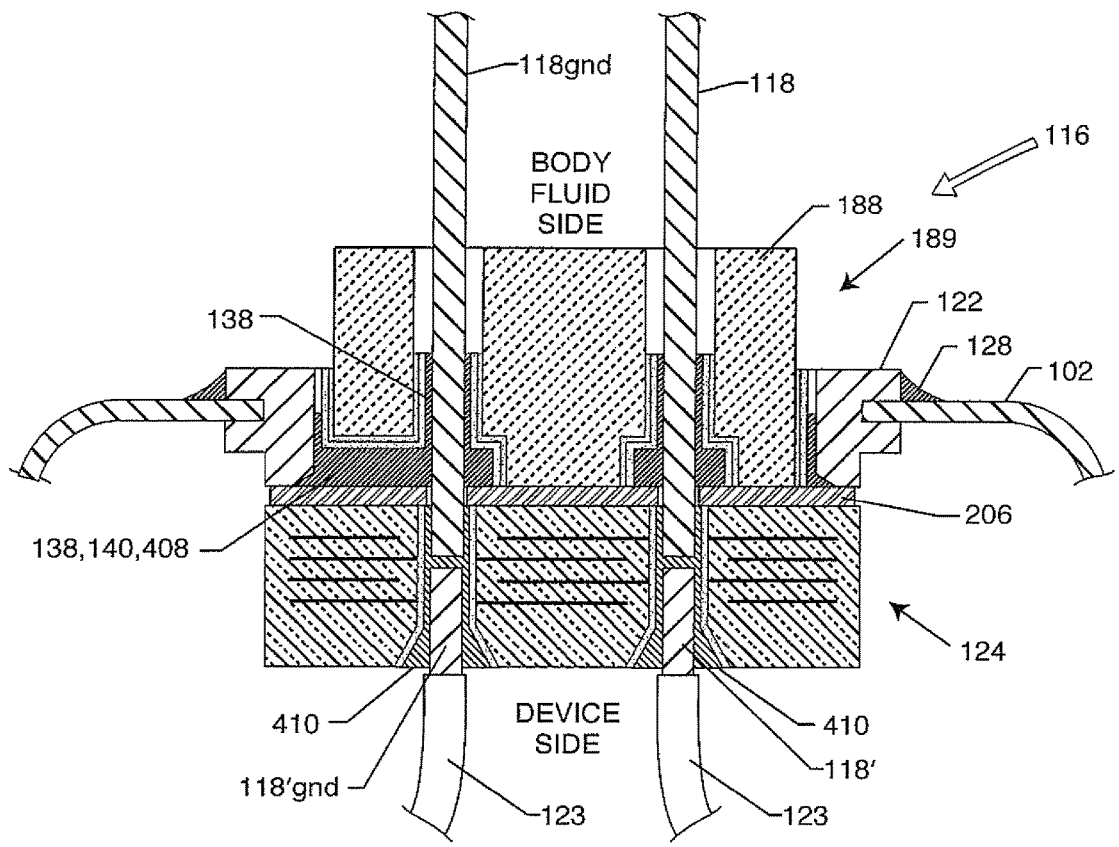
FIG. 24 is similar to FIG. 8, but now shows a gold braze moat electrically coupling the internal ground pin and the ferrule.

FIG. 24 seems similar to FIG. 8, but it also incorporates all the important advantages previously described for internally grounded capacitors shown in FIGS. 5, 6, 7 and 7A. Internally grounded feedthrough capacitors are described in U.S. Pat. No. 5,905,627, the contents of which are incorporated herein by reference. Referring back to FIG. 6, one can see that an internal ground pin 118gnd was provided by co-brazing it into a peninsula 139 of ferrule 122. Instead of machining a peninsula 139 out of the titanium ferrule, a gold braze moat 138, 140, 408 is provided. One will appreciate that when viewed isometrically, this gold braze moat could have the very same appearance as a peninsula 139 as previously described in FIG. 6. One will appreciate that this peninsula could have rounded or square edges or the like. (In other words, it need not look identical to that previously illustrated in FIG. 6). Also, there could be a number of these peninsulas, particularly for a long, rectangular part in order to provide a low impedance connection to the feedthrough capacitor internal ground electrode plates. It will also be appreciated that these peninsulas could alternate along the left and right sides of a long rectangular internally grounded feedthrough capacitor. Again, this is in order to make sure that the impedance of the internal ground electrode plate are kept low, such that a high level of filter performance known as insertion loss can be achieved for each active pin. Referring back to FIG. 24, one will see that leadwire 118gnd has been extended into the body fluid side. As previously noted, typically it is not necessary to provide a grounded lead on the body fluid side. However, for certain AIMD abandoned lead port applications, for magnetic resonance imaging, a ground lead provided to the header block could be a very convenient way of dissipating energy from an abandoned lead or a defective lead. For a more thorough explanation, one is referred to U.S. Patent Publication 2014/024,3944, entitled HEADER BLOCK FOR AN AIMD WITH AN ABANDONED LEAD CONNECTOR CAVITY, the contents of which are incorporated herein by reference. The feedthrough capacitor 124 of FIG. 24 is internally grounded, as previously described in FIGS. 5, 6 and 7. It also has all of the intended advantages previously described in FIGS. 5, 6 and 7. In comparison to FIG. 8, one can see that the capacitor outside diameter metallization 132 has been completely eliminated. The capacitor outside diameter or perimeter electrical connection 148 to the ferrule has also been completely eliminated. As previously described, not only does this reduce many expensive manufacturing operations and eliminate expensive materials, but it also allows the capacitor body 124 to mechanically float from the ferrule 122. This is important during subsequent customer laser welding 128 of the filtered feedthrough subassembly 189 into the AIMD housing 102 as illustrated in FIG. 8. The capacitor 124 will be much less sensitive to the heat pulse (thermal shock) created by this laser welding 128 since it is thermally isolated and also mechanically isolated. In other words, there are mismatches in the thermal coefficient of expansion of the ferrule 122 and the ceramic dielectric 124 itself. The insulative washer 206 is preferably a thin washer, which is somewhat flexible; thereby, mechanically isolating the capacitor even further. This thermal isolation means that a lower temperature solder 410, 410' could be used since this material will not get as hot during laser welding 128 when the capacitor is internally grounded. On the device side, as shown in FIG. 24, one can see a low cost ground leadwire 118'gnd, which is routed to a circuit board (not shown). This ground wire 118'gnd is optional, but does provide a very convenient way of providing an AIMD housing ground 102 for the circuit board electronics. This is important where the AIMD housing 102 can is to be used as an electrode, perhaps an implantable defibrillator application.

Referring once again to FIG. 24, in comparing it to the prior art, as illustrated in FIGS. 3 and 4, one can see that there are many advantages when compared to the prior art of FIGS. 3 and 4. Some of these advantages include: 1) elimination of the expensive platinum or palladium leadwires that extend from the device to the body fluid side, shown as 118 and 118' in FIG. 3 with replacement of the device side leadwires with very low cost leadwires, such as tin-copper or insulated tin-copper; 2) Replacement of the relatively expensive electrical connection material 146 shown in FIG. 4, which in the prior art generally is a thermal-setting conductive polyimide, which makes a connection between the feedthrough capacitor inside diameter metallization 130 and the through leadwire 118. As shown in FIGS. 3 and 4, replacement of material 146 is a very laborious process involving hand operations by injecting a thermal-setting conductive adhesive with a hand syringe, centrifuging that into place, pre-curing it, micro-blasting away excess material, inspecting and then repeating that process as much as four to five times. In FIG. 24, this has all been replaced by one simple solder preform process 410, which makes all the required joints simultaneously. By replacing the rather lengthy leadwires with the short leadwire 118, one has also designed the device of FIG. 24 for robotic assembly (automation). A robot can place the adhesive washer 206 over the leadwire 118 and a robot can also place the feedthrough capacitor 124. The solder preforms 410 could either be threaded by robot or by hand or then inserted into the feedthrough capacitor via holes as shown. Then either a conveyor belt or a batch process is used to reflow the solder preform without the need for repetitive processes. It has been found through experimentation that the manufacturing yield of the product, as illustrated in FIG. 24, is in the high 99% range. This is an increase in manufacturing yield of greater than 5% compared to the prior art technology illustrated in FIGS. 3 and 4. Another important advantage that is not really apparent from FIG. 24 is that it is completely and easily reworkable. The most expensive subcomponent in FIG. 24 is the hermetic seal subassembly 189. It has gold brazes, which are expensive; sputtering, which is expensive: and alumina insulator, which is expensive. In addition, the ferrule itself 122 tends to be very expensive. It is common practice after the subassembly 116 is formed to do extensive thermal, mechanical and electrical testing before this subassembly 116 is shipped to a customer for installation into an AIMD housing 102. This includes elevated temperature voltage application otherwise known as burn-in and the like. There is usually some infant mortality in the capacitor population 124, meaning that there is a yield associated with this high reliability electrical and mechanical pre-screening. If the capacitor 124 does fail electrically or fails one of its insulation resistance tests, it is easily removable by simply heating it up. In other words, all one has to do is reflow the solder preform 410 and then remove the capacitor from the insulative washer 206 and simply install a new feedthrough capacitor and reuse the hermetic seal subassembly. This is an enormous advantage of the present invention.

Figure 24A:
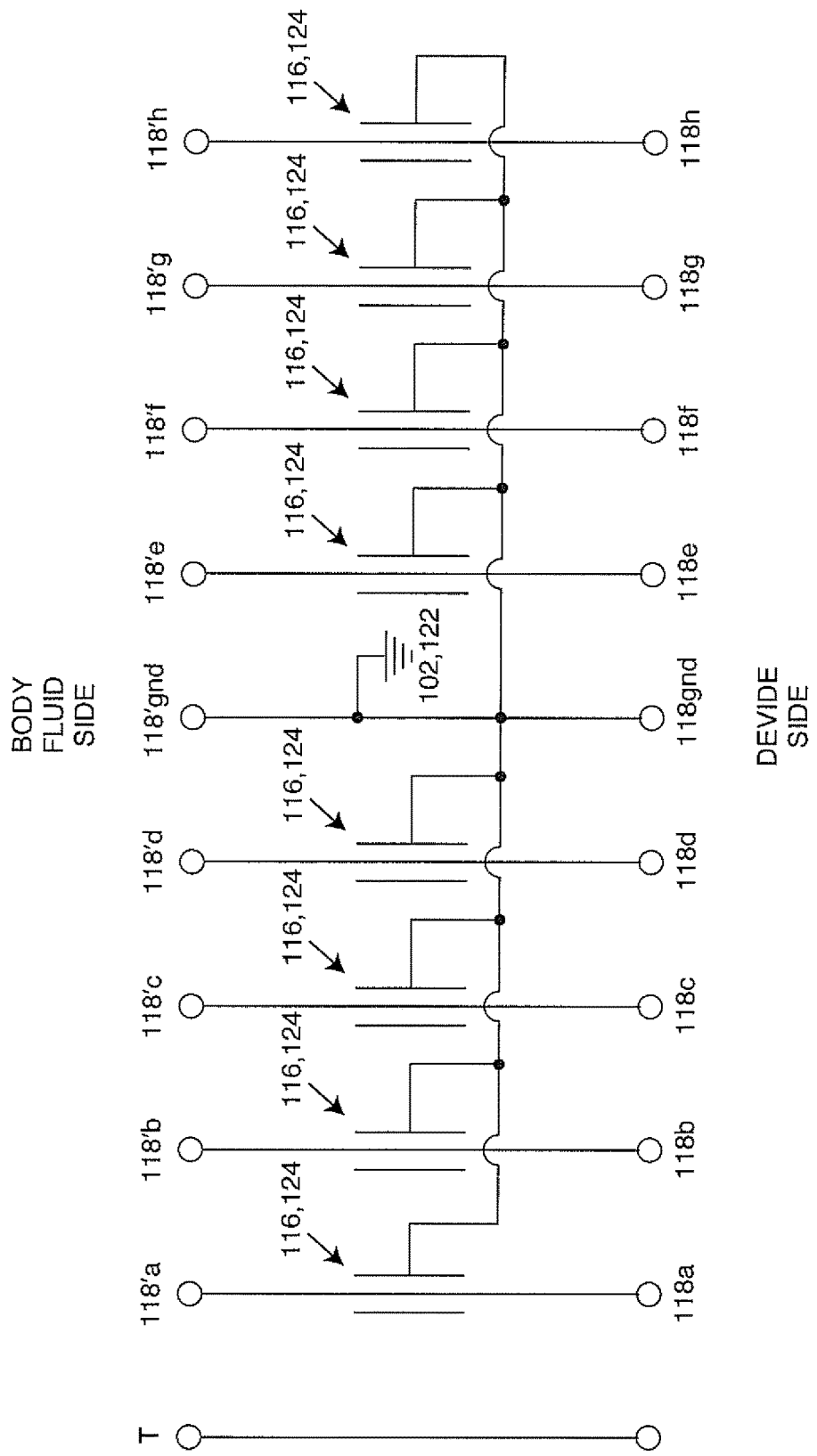
FIG. 24A is one possible schematic diagram of the filtered feedthrough assembly of FIG. 24.

Referring once again to FIG. 3 and the length of device side leadwires 118', one can appreciate why it has never been possible to automate the placement onto the hermetic seal subassembly 189, the feedthrough capacitor insulation washer 206 and the feedthrough capacitor 124 itself. It is because the device side leadwires are so long that they are not rigid and it is literally impossible to keep the tolerance such that they will point perfectly straight. On the other hand, referring to FIG. 24, one can see that the relatively short device side leadwire 118 are also pointing straight and rigid. Accordingly, one can appreciate that the assembly of FIG. 24 is readily built by robots and is completely designed for automation. It is only the last step, which involves placement of low cost leadwires 118' that a human hand may be required FIG. 24A is one possible schematic diagram of the filtered feedthrough assembly 116 of FIG. 24. Referring to FIG. 24A, one can see that the ground pin 118gnd extends from the body fluid side all the way to the device side. One will also appreciate that any number of active leadwires 118' are possible from monopolar to bipolar to tripolar . . . all the way to "n" number of active leads. One will also appreciate that the telemetry pin T is optional or may even embody a multiplicity of RF telemetry pins T.

Figure 24B:
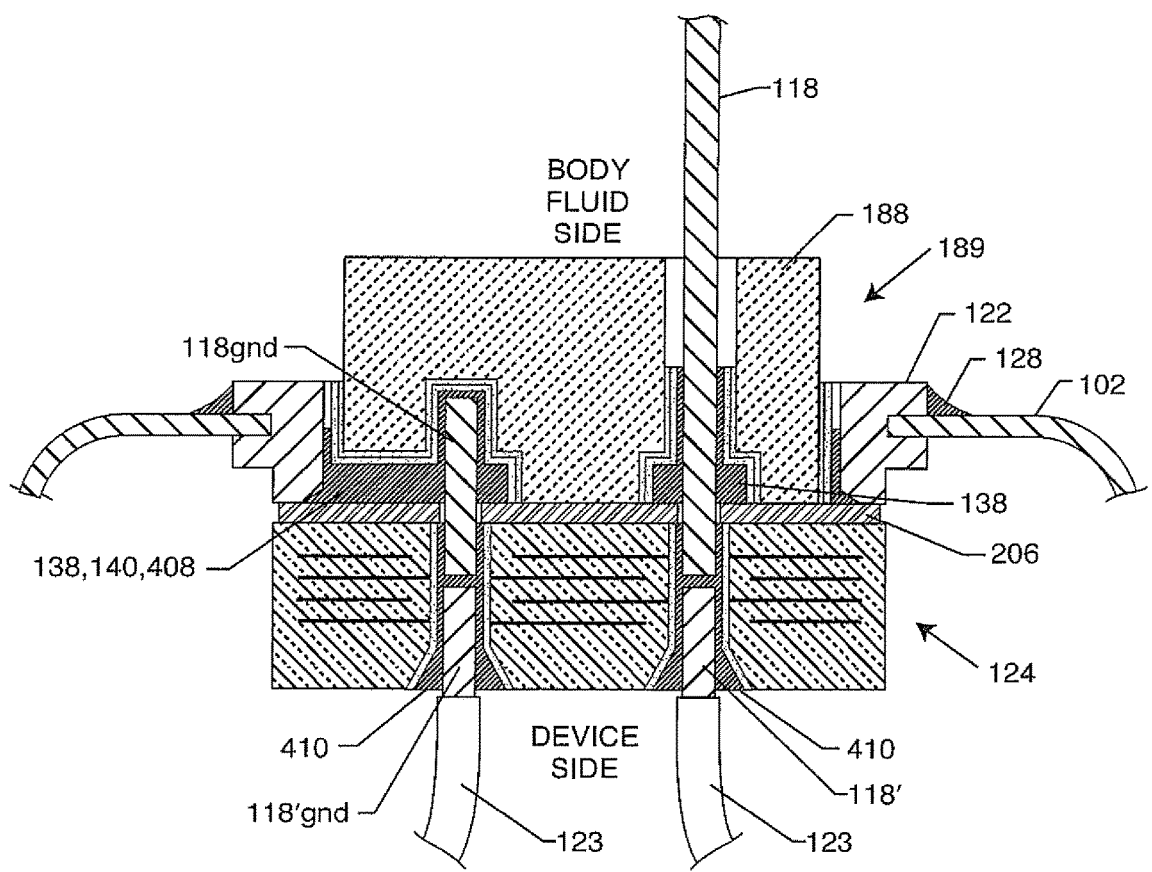
FIG. 24B is very similar to FIG. 24, except the body fluid side ground lead has been eliminated from extending past the insulator.

FIG. 24B is almost the same as FIG. 24, except the body fluid side ground lead 118gnd has been eliminated. In most AIMD applications, it is not necessary to provide an implanted lead conductor that has the same potential as the AIMD housing 102. Referring once again to FIG. 24B, one can see that the gold braze preform 138, 140, 408 has covered the top 138 on the body fluid side of the short leadwire 118gnd. Referring once again to FIG. 24B, one can see that the schematic previously described in FIG. 7A could apply. Referring to FIG. 7A, one notes that the device side ground pin 118gnd does not extend to the body fluid side. Again, any number of active pins are possible and the telemetry pin is optional.

Figure 25:
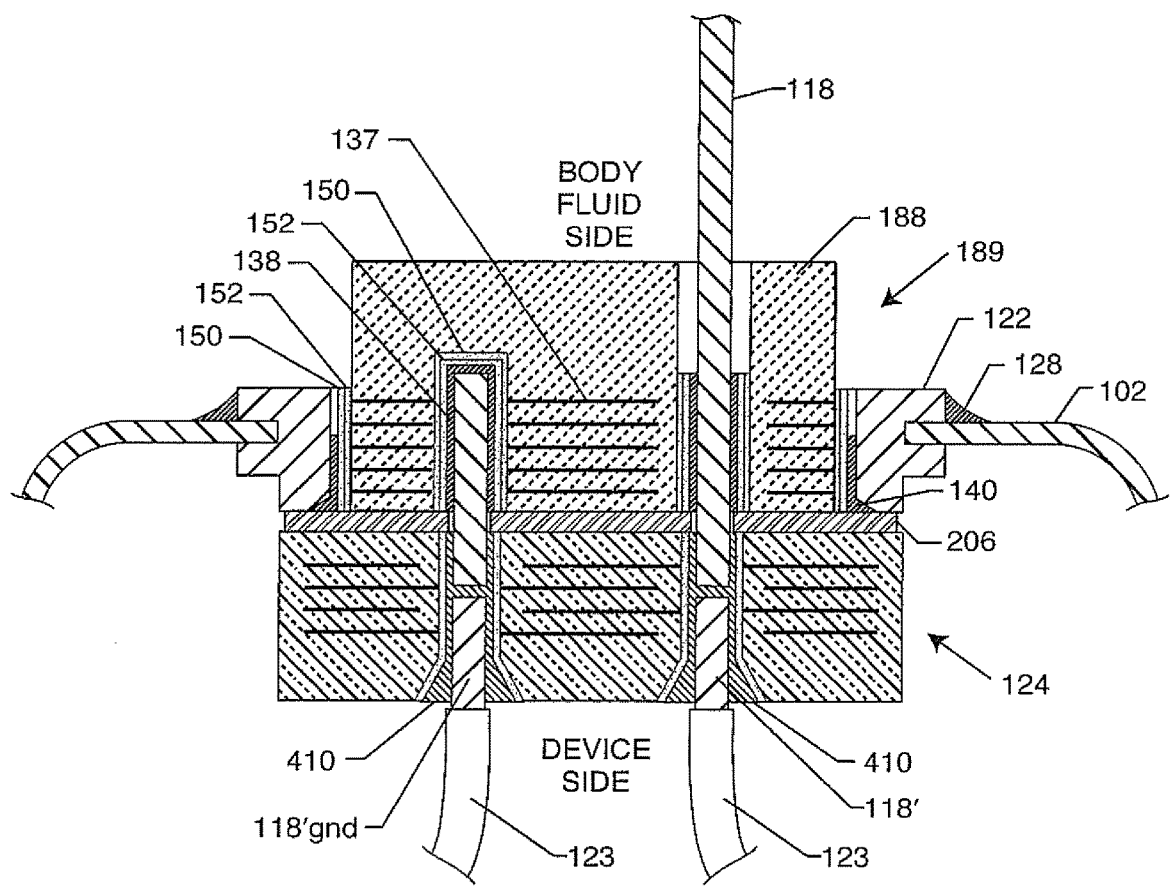
FIG. 25 illustrates an internally grounded feedthrough capacitor as previously described in FIG. 24, except that the gold braze moat has been replaced by internal ground plates that are embedded within a multilayer and co-fired insulator.

FIG. 25 illustrates an internally grounded feedthrough capacitor 124 as previously described in FIG. 24, except that the gold braze moat 138, 140, 408 has been eliminated and instead replaced by internal ground plates 137 that are embedded within a multilayer and co-fired alumina ceramic insulator 188. Sputtering of the adhesion 152 and wetting layers 150 electrically connects these embedded ground plates 137 in parallel. Subsequent gold brazing operation 138 electrically connects the ferrule 122 by way of this sputtering 150, 152 to the ground plates 137. Embedded ground plates within a hermetic insulator are described by U.S. Pat. No. 7,035,076, the contents of which are incorporated herein by reference. Accordingly, the internally grounded structure illustrated in FIG. 25 has all of the advantages previously described for FIG. 24.

Figure 26:
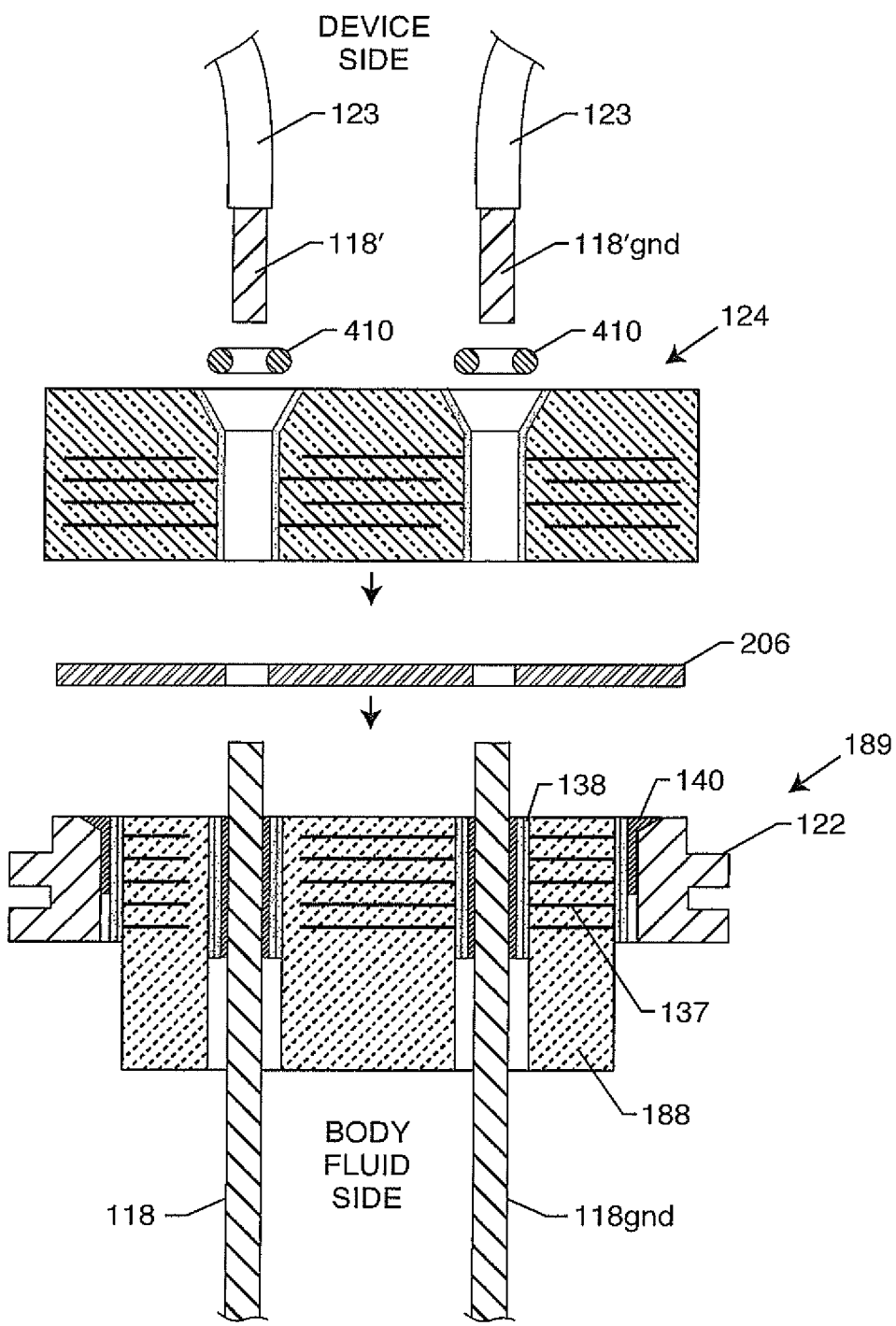
FIG. 26 illustrates the assembly steps for the structure of FIG. 25 in a manner very similar to that previously described in FIG. 9.

FIG. 26 illustrates the assembly steps for the structure of FIG. 25 in a manner very similar to that previously described in FIG. 9. A major advantage is the elimination of the capacitor outside diameter or perimeter metallization and electrical attachment to the ferrule (reference FIG. 8 electrical attachment material 148). Accordingly, FIG. 26 is completely designed for automation.

FIG. 26 is the assembly of FIG. 25 showing it exploded into its various subcomponents. Shown is the internally grounded hermetic insulator subassembly 189 and the internally grounded feedthrough capacitor 124 ready to be disposed on top of the adhesive washer 206 and on top of the hermetic seal insulator 188. As previously described, this assembly can be automated and can be reflowed in a conveyor belt, furnace process or in a bulk process, such as a DAP sealer.

Figure 27:
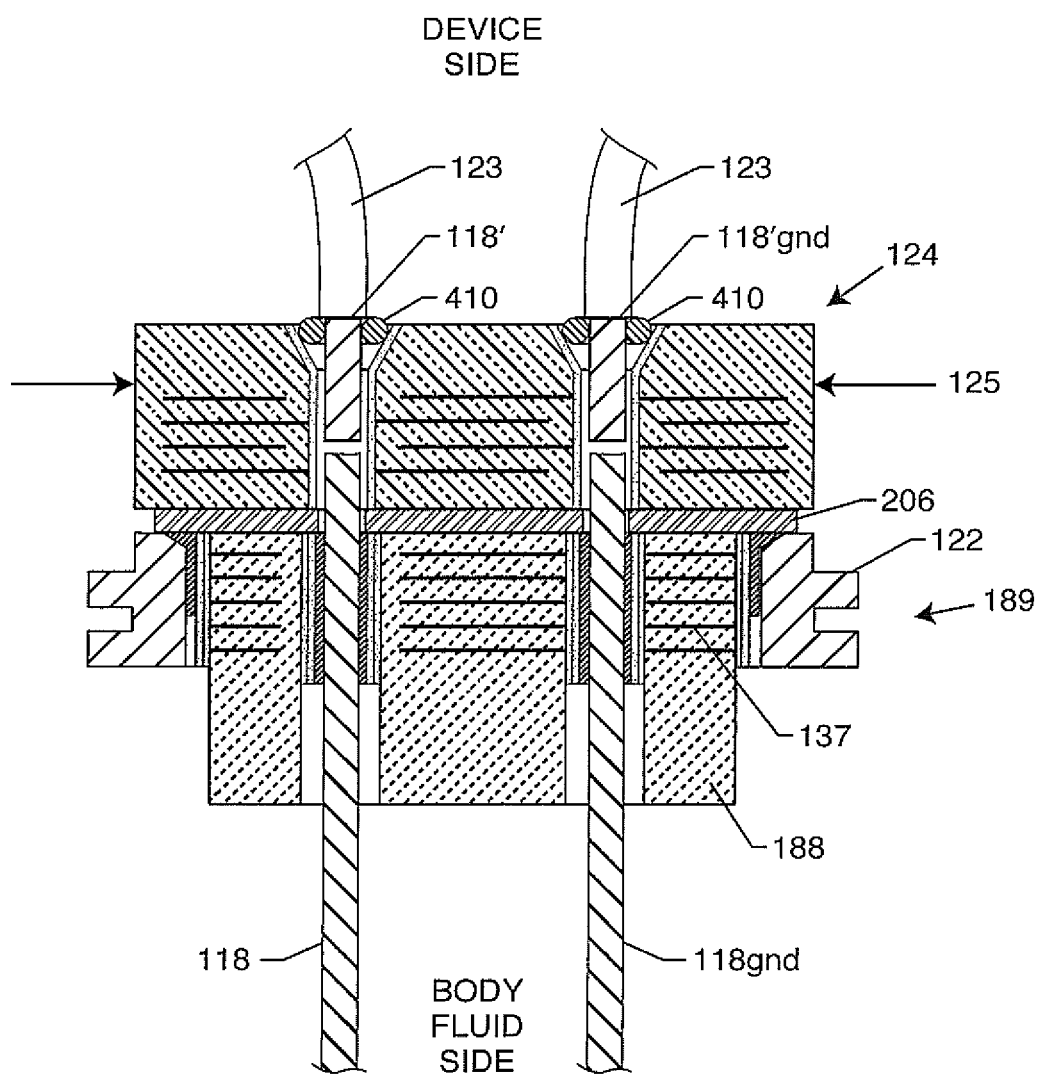
FIG. 27 illustrates the exploded components of FIG. 26 after the capacitor has been adhesively bonded to the hermetic seal insulator and ferrule.

FIG. 27 illustrates the exploded components of FIG. 26 after the capacitor 124 has been adhesively bonded 206 to the hermetic seal insulator 189 and ferrule 122. Solder preform 410 is in place and ready to be reflowed. Attention should be drawn to another very important advantage of the present invention. This can be seen in FIG. 27 as the diameter or the dimension of a rectangle 125. By elimination of any electrical connection between the capacitor outside diameter or perimeter to the ferrule 122, the capacitor 124 can actually be made larger in diameter or in a rectangular dimension. This adds enormously to the capacitor's effective capacitance area (ECA). It should be noted that this ECA is a square law. For example, if one were to double the outside diameter or double the length and width, one would multiply the effective capacitance area by a factor of four. So even a 10% addition, or 20% addition to the capacitor diameter, greatly increases its volumetric efficiency.

Figure 28:
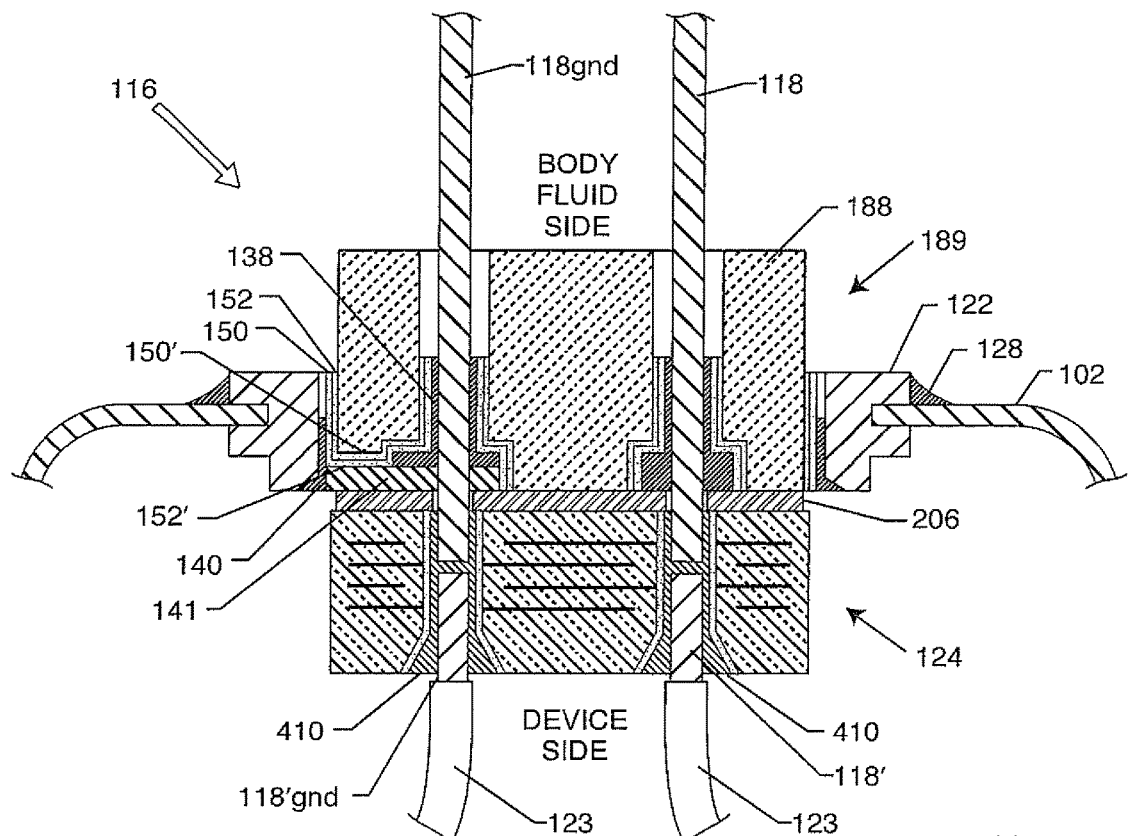
FIG. 28 is another internally grounded capacitor similar to those previously described in FIG. 24 and FIG. 25 where now the gold braze moat of FIG. 24 has been largely replaced with a metallic piece.
Figure 29:
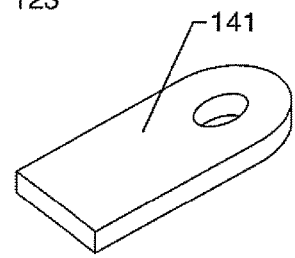
FIG. 29 is a perspective view of the metallic piece from FIG. 28.

FIG. 28 is another internally grounded capacitor 124 similar to those previously described in FIG. 24 and FIG. 25. The advantage of FIG. 24 is that the relatively expensive gold braze moat 138, 140, 408 of FIG. 24 has been largely replaced with a metallic piece (conductive clip) 141 illustrated isometrically in FIG. 29. This metallic piece 141 would typically be of titanium so that it will readily accept gold brazes 138 and 140. The advantage of using a titanium metallic piece 141 is that less gold is required and of course, gold is very expensive. FIG. 29 is a perspective view of the metallic piece from FIG. 28. It will be noted in FIG. 28 that in the area where the metal piece 141 is located, sputter layers 150 and 152 cover this peninsula area of the hermetic insulator 188. This means that in actual production that the gold braze layer 138 would merge with the gold braze layer 140 as a very thin line of gold above the metal piece 141. This is desirable since it enhances the mechanical, structural and hermetic stability of the entire package. It will be understood that this thin layer of gold will typically be present, but is not shown for simplicity. It is also likely or even probable that the thin layer of gold will partially or totally cover both the top and bottom of the metal piece 141

Figure 30:
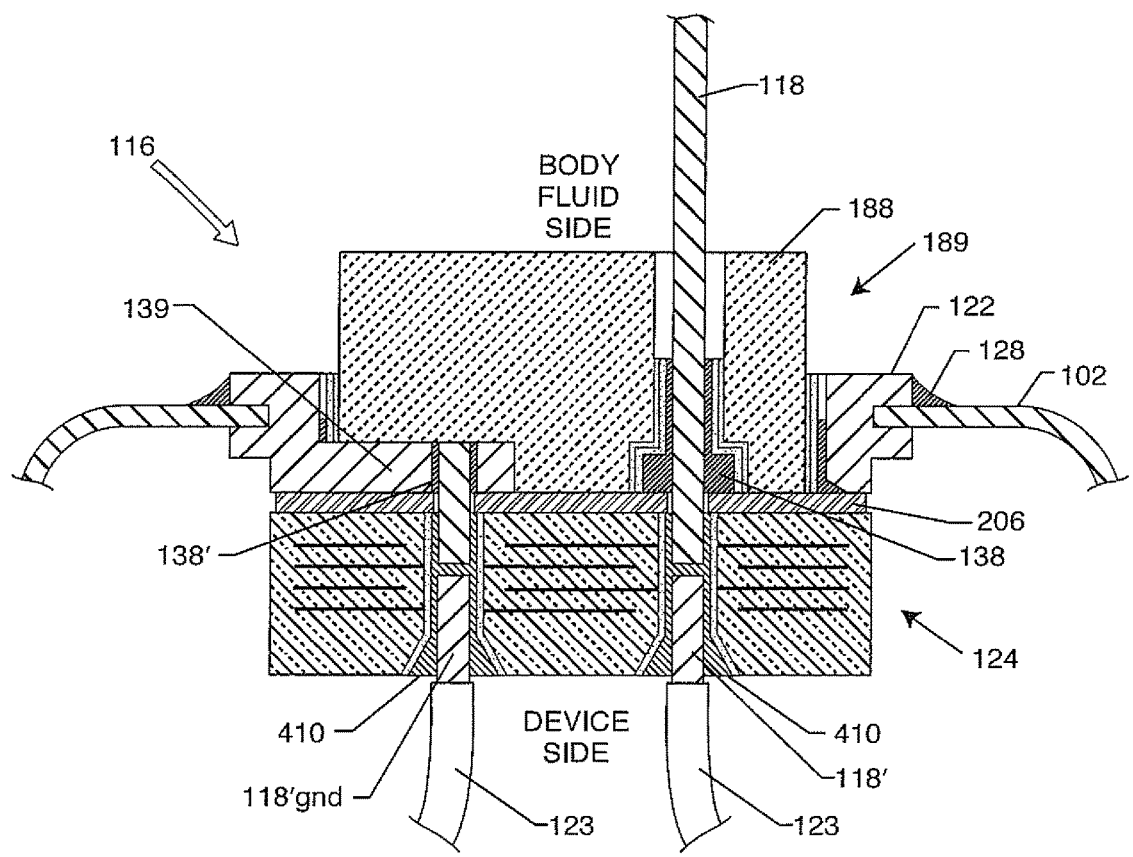
FIG. 30 is another internally grounded capacitor version similar to FIGS. 25 and 28 where now the ferrule has been extended into a peninsula and electrically coupled to the ground lead.

FIG. 30 is another internally grounded capacitor version. In this case, the ferrule 122 has been extended into a peninsula 139 as shown. The ferrule 122 would be machined such that, the peninsula 139 is formed. This is best understood by referring back to prior art FIG. 6 where one can see peninsula 139. The peninsula 139 could be very similar in shape. As previously noted, there could even be multiple peninsulas and multiple ground leads.

FIG. 31 illustrates a prior art monolithic ceramic capacitor 194. These are otherwise known as MLCCs. Monolithic ceramic capacitors are very well known in the prior art and are produced daily in the hundreds of millions. MLCCs are common components in every electronic device, including computers, modern smart phones and the like. It should be noted here that not all rectangular 2-terminal capacitors, as illustrated in FIG. 31, must be ceramic. As used herein, MLCC or monolithic ceramic capacitors shall also include all kinds of stacked tantalum, stacked film and other dielectric type capacitors that form 2-terminal rectangular shapes. It will also be appreciated that any of the 2-terminal capacitors in the art, including ceramic, film and tantalum could also have other shapes other than rectangular, including cylindrical and the like.

FIG. 32 illustrates a cross-section of an MLCC capacitor. As can be seen, the prior art MLCC is a two-terminal device having a metallization on the left 130 and a metallization on the right 132. It has overlapping electrodes as illustrated in FIGS. 33 and 34. It has an effective capacitance area ECA created by the overlap of the left hand electrodes 134 with the right hand electrodes 136.

Figure 35:
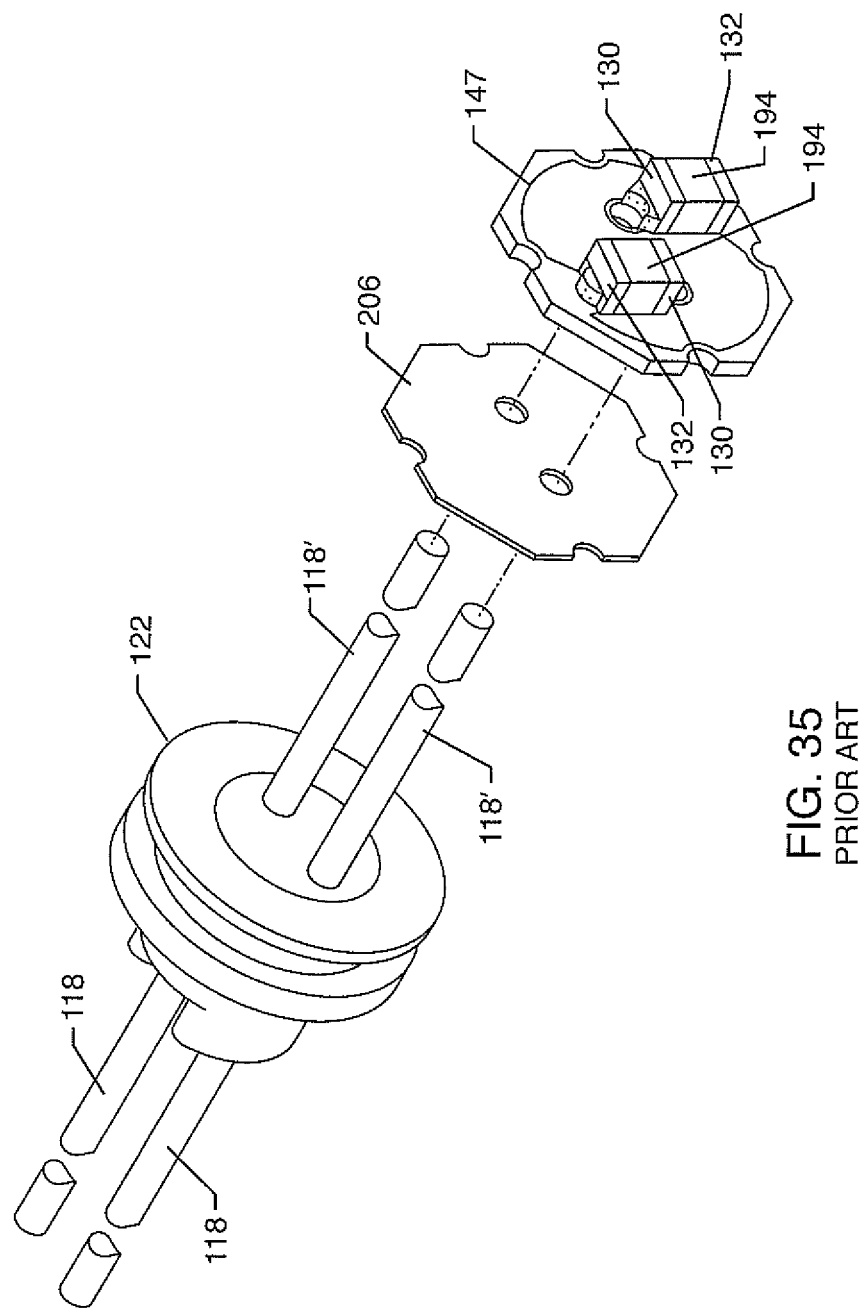
FIG. 35 illustrates a bipolar prior art applications of MLCC capacitors to active implantable medical device applications.
Figure 35A:
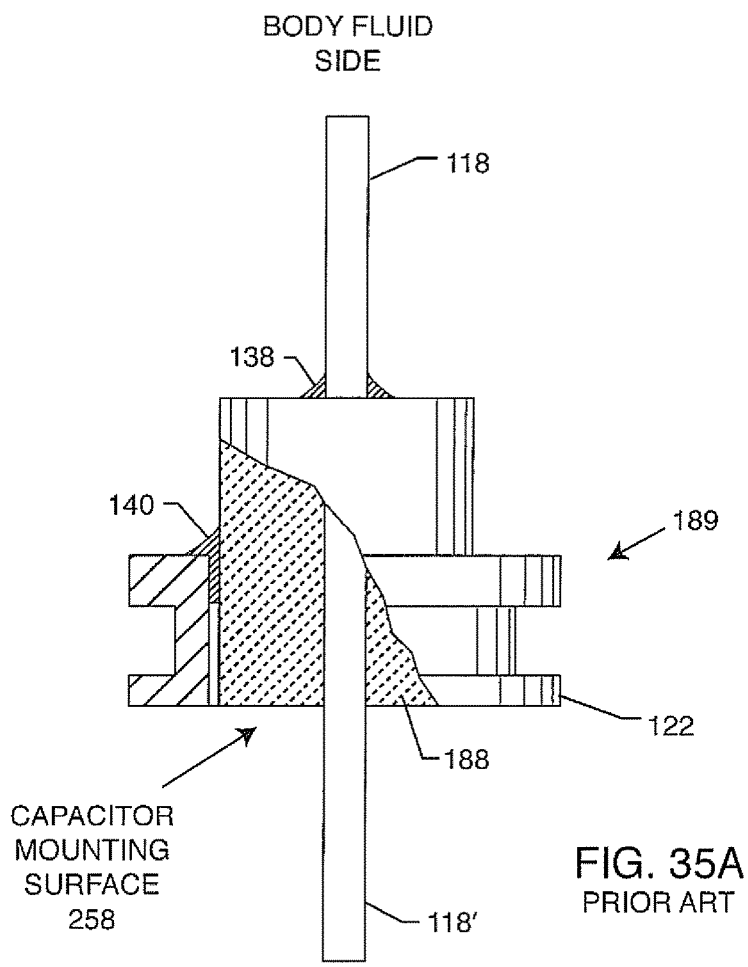
FIG. 35A illustrates a unipolar prior art applications of MLCC capacitors to active implantable medical device applications.
Figure 35B:
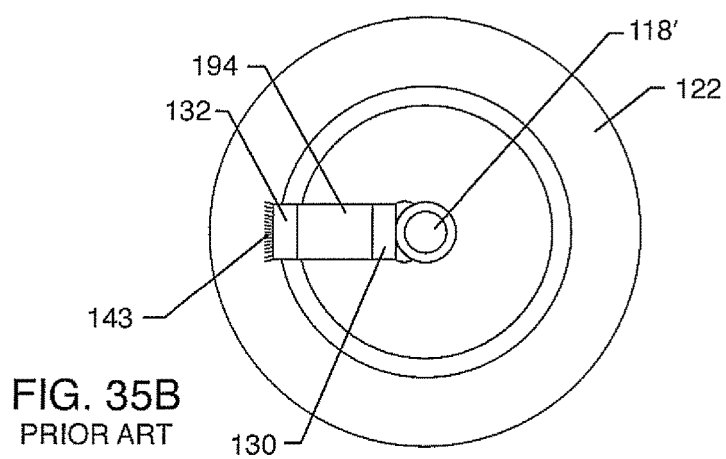
FIG. 35B illustrates a top view of the structure of FIG. 35A.

FIGS. 35, 35A and 35B illustrate prior art applications of MLCC capacitors 194 to active implantable medical device applications. These patents include: U.S. Pat. Nos. 5,650,759; 5,896,267; 5,959,829 and 5,973,906, the contents of which are incorporated herein by reference.

Figure 36:
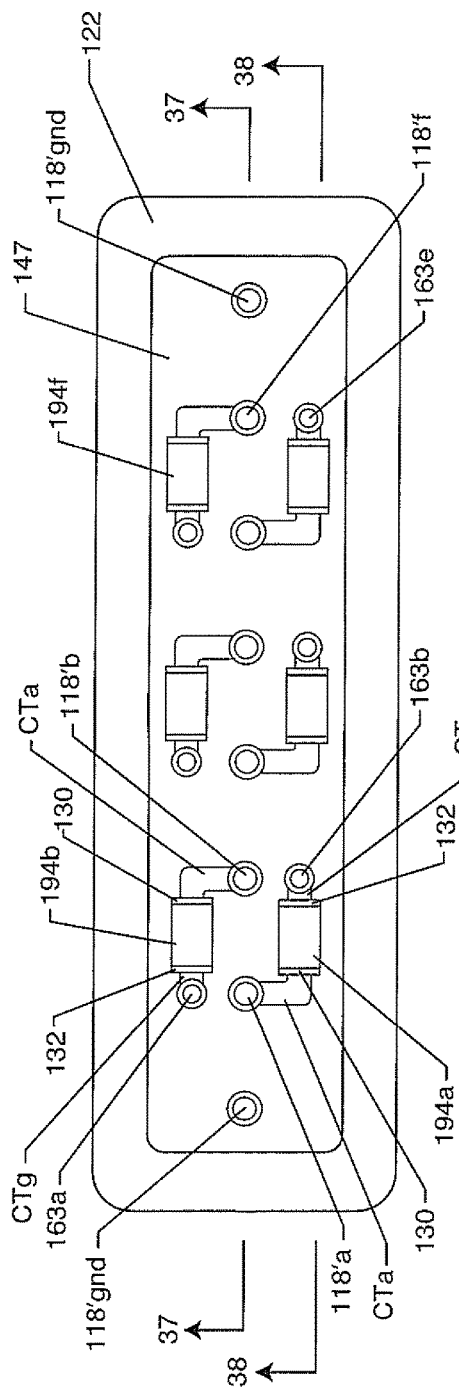
FIG. 36 is a top view of a hexapolar filtered feedthrough of the present invention.

FIG. 36 describes a hexapolar (6) hermetically sealed filtered terminal in accordance with the present invention. Shown are 6 MLCC capacitors 194a through 194f that are mounted onto circuit board 147. The circuit board is best shown in FIG. 37, which is taken from section 37-37 from FIG. 36.

Referring once again to FIG. 37, one can see the pins 118a, 118b and 118c have been pre-welded or pre-brazed or pre-attached by therma-sonic, ultrasonic or other bonding processes to the device side leads 118'a, 118'b and 118'c. Referring once again to FIG. 37, one can see that leads 118d, 118e and 118f have not been pre-attached to the device side leads and in fact, there is a small gap between them. After the circuit board 147 is disposed adjacent the ferrule or insulator, the electrical connection 410 is used to connect to device side leadwires 118' into the via hole and also make contact to circuit traces CTa, as previously illustrated in FIG. 36. The circuit trace CTa electrically connects the leadwires 118, 118' to the active metallization 130 of the respective MLCC chip capacitors 194. Referring once again to FIG. 37, for leadwires 118a, 118b and 118c, the electrical connection material 410 is not shown contacting the gold braze 138 of the hermetic seal insulator 188. However, a close examination of the electrical connection material 410 for leadwires 118d, 118e and 118f shows that the electrical connection material 410, which can be a solder, a thermal-setting conductive adhesive or the like, contacts both the device side leadwires 118'd, 118'e and 118'f as well as body fluid side leadwires 118d, 118e and 118f. Importantly, this electrical connection material 410 for leads 118d, 118e and 118f also directly contacts the gold braze 138, which provides a very low impedance and oxide-free electrical connection. This is particularly important in the case where the body fluid side leadwires 118d, 118e or 118f would be of a heavily oxidized material, such as niobium or tantalum or the like.

Figure 37:
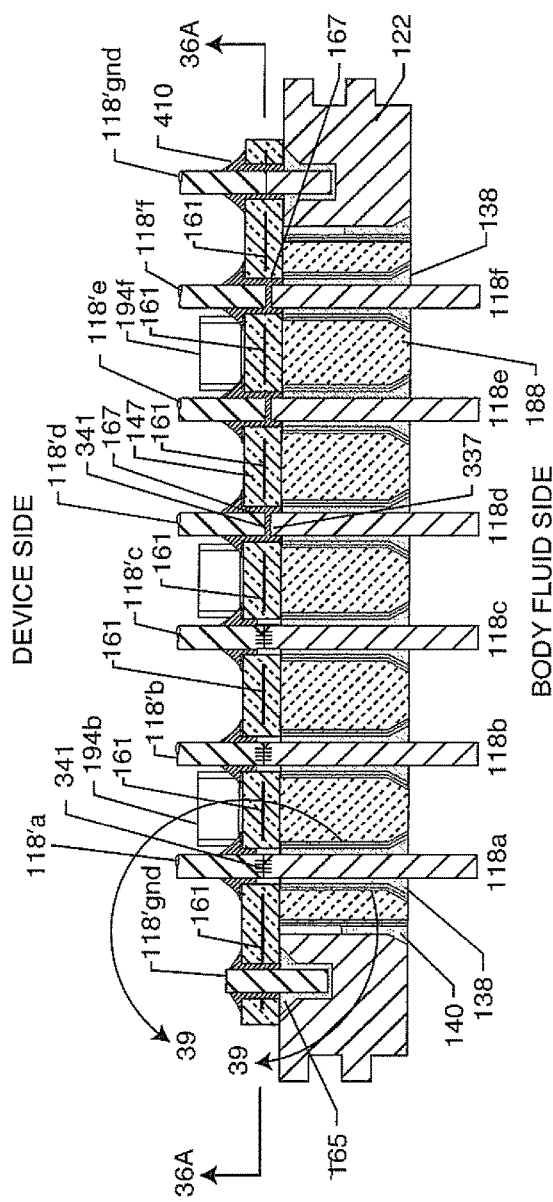
FIG. 37 is a sectional view taken along lines 37-37 from FIG. 36.
Figure 38:
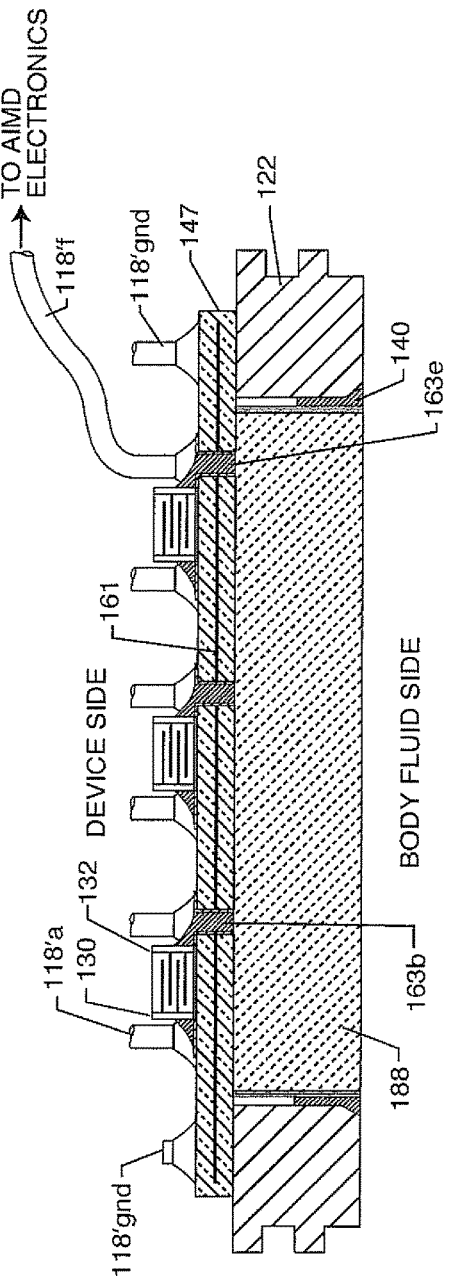
FIG. 38 is a sectional view taken along lines 38-38 from FIG. 36.

FIG. 38 is a second sectional view taken from section 38-38 from FIG. 36. As best shown in FIG. 37, there are two ground pins (or ground leadwires) 118'gnd that are directly co-brazed 165 into the ferrule 122 as shown. One of these ground pins 118'gnd is on the far left of circuit board 147 and the other is on the far right of the circuit board 147. Embedded within circuit board 147 is a ground circuit trace 161 (also called a ground electrode plate, ground electrode plane, or ground plane). The active hexapolar leadwires on the device side are labeled 118'a through 118'f. Each one of these are associated with an MLCC capacitor which acts as an EMI low pass filter 194 or diverter. Referring to MLCC capacitor 194a in FIG. 36, one can see that on its ground metallization side 132, it is connected to ground via hole 163b. On the active termination side 130 of MLCC capacitor 194a, you can see a circuit trace (CTa) and an electrical connection to via hole about leadwire pin 118'a. Referring to FIG. 37, one can see the active device side pin 118'a running through the via hole of the circuit board 147 and being co-gold brazed with the hermetic insulator 188 to the body fluid side leadwire 118a. This is in accordance with the present invention. Referring once again to FIG. 36, MLCC capacitor 194a on its ground metallization side 132, it is connected through a short circuit trace (CTg) or directly through soldering or thermal-setting conductive adhesives to ground via holes 163b. Referring to FIG. 38, one can see in cross-section, the grounded via hole 163b, which is electrically connected to the embedded ground plane or ground circuit trace 161 within the circuit board 147. It will be appreciated by those in the art that the ground circuit trace 161 could take on many different shapes or dimensions or even be multilayer. For simplicity, a single layer is shown. It will also be appreciated that the embedded circuit trace 161 could also be placed on either the top or the bottom surface or both of the circuit board 147. Referring once again to FIG. 37, one could also see that the MLCC capacitors 194 are generally surface mounted on top of the circuit board 147. It will be appreciated that these MLCC capacitors 194 could be partially embedded into the circuit board or totally embedded within the circuit board in accordance with prior art techniques.

Figure 36A:
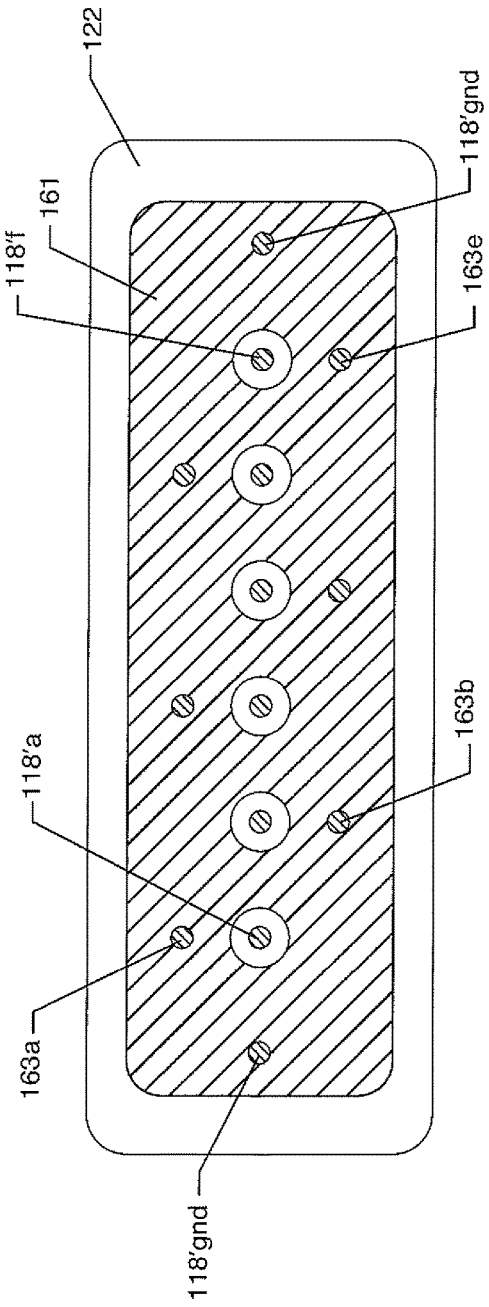
FIG. 36A is a sectional view taken along lines 36A-36A from FIG. 37.

FIG. 36A is taken generally from section 36A-36A from FIG. 37. This shows the top view of the ground plane 161. One can see that on the far left at 118'gnd and on the right, that this ground plane is grounded to the ferrule by pins 118'gnd. In general, its connection to the ferrule 122 is by co-brazing 165. In accordance with the present invention, it would be desirable that these pins on the device side be of non-oxidizable material, such as palladium or platinum. Other materials or alloys, such as platinum-iridium or palladium-iridium, can also be used. On the device side, these leadwires 118' are generally long so that they can be routed to a distant circuit board 126 having AIMD electronic circuits. Referring once again to FIG. 36, one can see the second MLCC capacitor labeled 194b. It is connected at its active termination 130 to via hole 118'b, which is also illustrated in FIG. 37. Referring once again to MLCC capacitor 194b, its ground termination 132 is connected to ground via hole 163a. Ground via hole 163a is illustrated in its sectional view in FIG. 36A wherein, it is electrically connected to ground plane 161. In turn, ground plane 161 is electrically connected to the left and the right grounded pin 118'gnd. Accordingly, the ground circuit trace or ground plane 161 is at the same electrical potential as the ferrule 122. As previously described, ferrule 122 is designed to be laser welded into an AIMD housing 102. The AIMD housing becomes an overall equipotential surface. Accordingly, AIMD electronics are protected from electromagnetic interference from this overall electromagnetic shield. This protects AIMD electronics from what is known as direct radiated electromagnetic interference. Another way electromagnetic interference can enter into the AIMD housing and disrupt the proper operation of sensitive AIMD circuits is through conductive interference. Conductive interference occurs when AIMD leadwires pick up radiated electromagnetic interference and act as antennas and then conduct that interference through the hermetic seal insulator assembly 189 into the interior of the AIMD housing. This is what the MLCC capacitors 194 are designed to divert at the point of ingress of the electromagnetic interference. Capacitors 194 divert this undesirable electromagnetic interference energy away from the active leadwires 118 to the ferrule 122 and in turn, to the overall equipotential surface of the AIMD housing where the energy is dissipated as a miniscule amount of temperature rise inside of a body fluid pocket (not shown). Referring back to FIG. 36, one can see that the MLCC capacitors 194*a*, 194*b* all the way to 194*f*, alternate their active connections back and forth along with their ground connection, which also alternate as shown in FIG. 36A. It will be appreciated that the hexpolar (6) filter hermetic terminal of FIGS. 36 through 39 can be of any number of terminals, including "n" active terminals, which would embody "n" MLCC capacitors. It will also be appreciated that non-filtered telemetry pins T (not shown) could be added.

Referring once again to FIG. 37, one can see that there is a ground pin 118'*gnd* on both the right and left hand sides of circuit board 147. First of all, there can be any number of these ground pins as is required to provide a low impedance path across ground plane 161. In this case, two were chosen so that each of the active pins 118'*a* through 118'*f* has a low impedance ground connection thereby providing optimal filtering attenuation (insertion loss).

These ground pins 118'*gnd* are also known as metal additions in accordance with U.S. Patent Publication 2014/0168917, the contents of which are incorporated herein fully by reference. For example, one is referred to FIG. 36 of the '917 U.S. Patent Publication as showing metal addition 220.

Figure 39:
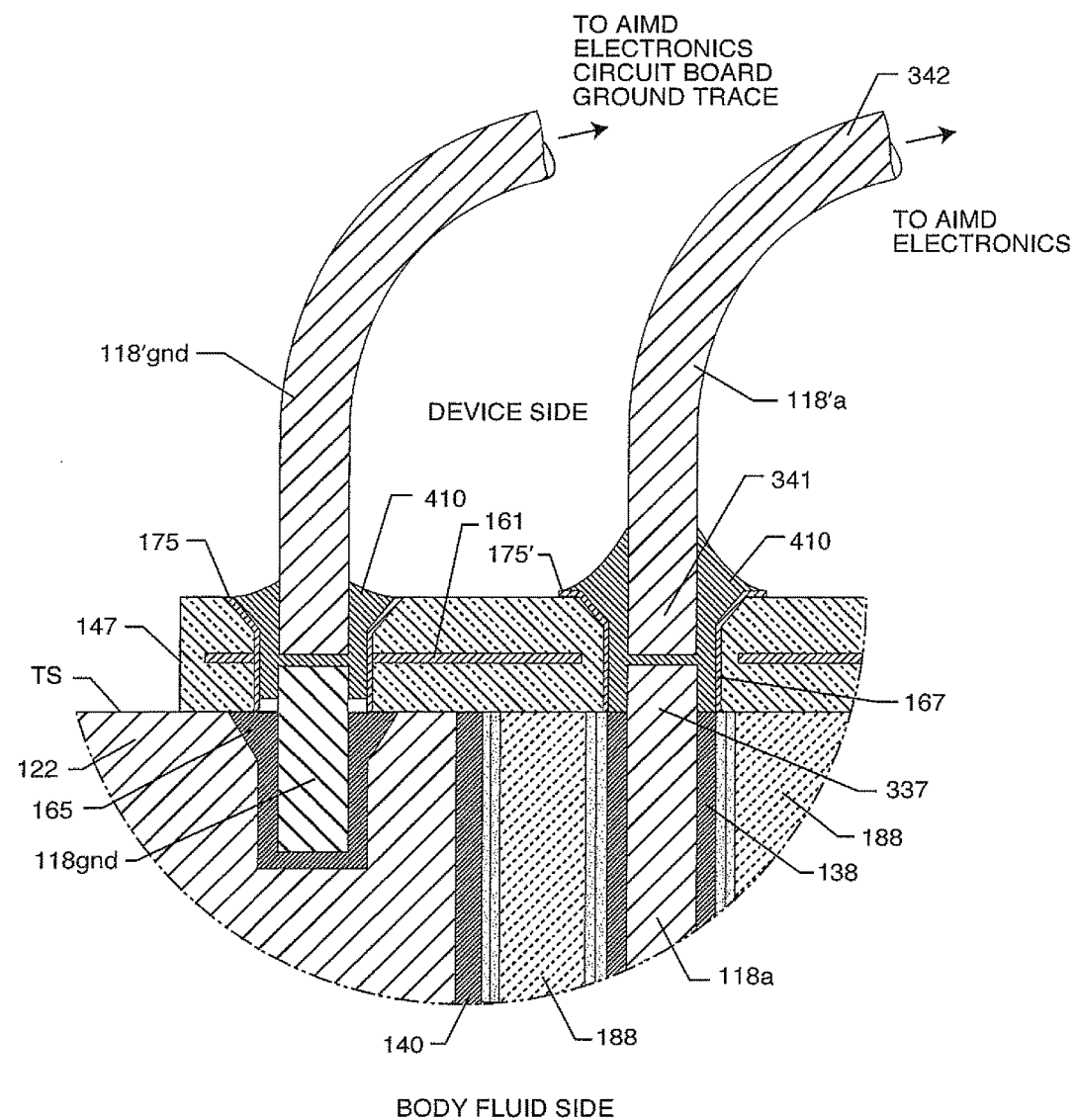
FIG. 39 is an enlarged view taken along lines 39-39 from FIG. 37 but is now showing a new embodiment.

FIG. 39 is a sectional view generally taken from section 39-39 from FIG. 36. This shows an important low cost alternative to running the leadwires 118' all the way to AIMD electronic circuits. It needs to be remembered that as illustrated in FIGS. 36 through 38, that these leadwires 118' are generally of platinum, palladium or various alloys involving iridium. Referring back to FIG. 39, one can see that the device side leadwire 118' can generally be a very low cost leadwire comprising either solid or stranded copper, tin copper or the like. As shown, electrical connection material 410 joins the low cost leadwire 118' to the body fluid side leadwire pin 118*a*. As can be seen, the device side leadwire 118'*a* is generally butted up close to or adjacent 342 the end 337 of the body fluid side leadwire pin 118*a*. On the left hand side of FIG. 39, one can see the ground pin 118*gnd*, which is gold brazed 138 to the ferrule 122. In this case, since the electrical connection material 410 does not contact the gold braze 138, the ground pin 118*gnd* would have to be of a non-oxidized, preferably, solderable material, such as platinum or palladium. In the case where a low cost body fluid side leadwire pin 118'*a* is used, such as niobium, tantalum, or titanium, then, it would be necessary that the electrical connection material 410 flow down and contact the gold braze 138, such that a low resistance and low impedance connection is achieved between body fluid side leadwire 118*a* and low cost device side leadwire 118'*a*. In this case, it is not necessary that electrical connection material 410 make a direct electrical connection to the pin 118*a* (which would be heavily oxidized). During the gold braze operation, in general a gold braze preform 138 would be used. In general, the gold brazing operation of the hermetic seal subassembly 189 is performed in a vacuum furnace at a high temperature. This gold brazing operation removes any oxide present on pin 118*a* and the gold braze preform then makes a very low impedance and low resistance metallurgical connection to the base metal of pin 118*a*. The top surface of this gold braze 138 is therefore of nearly pure gold, which results in an oxide-free surface to which electrical attachment material 410 can make a very low resistance and low impedance electrical connection. This is an important feature of the present invention in that, the body fluid leadwire or pin 118*a* can be of very low cost materials as contrasted with platinum or palladium. Referring once again to FIG. 39, one can see a feature of FIG. 37 that was not readily viewable. This is the via hole metallization 175. As shown in FIG. 37, this metallization can be on the inside diameter of a straight via hole or one that is counter-sunk as shown, or counter-bored (not shown). It will also be appreciated that in circuit board technology that metallization layer 175 could be of an eyelet type construction. Importantly, the via hole metallization 175, 175' allows the electrical connection materials 410, such as a solder to wet both to the lead 118' and to the via hole metallization 175 thereby, increasing the shear area and thereby, increasing pull strength.

Referring once again to FIG. 39, one will note that the ground pin 118*gnd* gold braze 165 is flush with the top surface TS of the ferrule 122. One will also note that the gold braze 138 around the body fluid side pin 118*a* is also shown flush, this time, flush at the top side of insulator 188. This is an idealized drawing in that, during an actual gold braze furnace operation, the gold preform turns to a liquid during its reflow and has capillary properties.

Figure 39A:
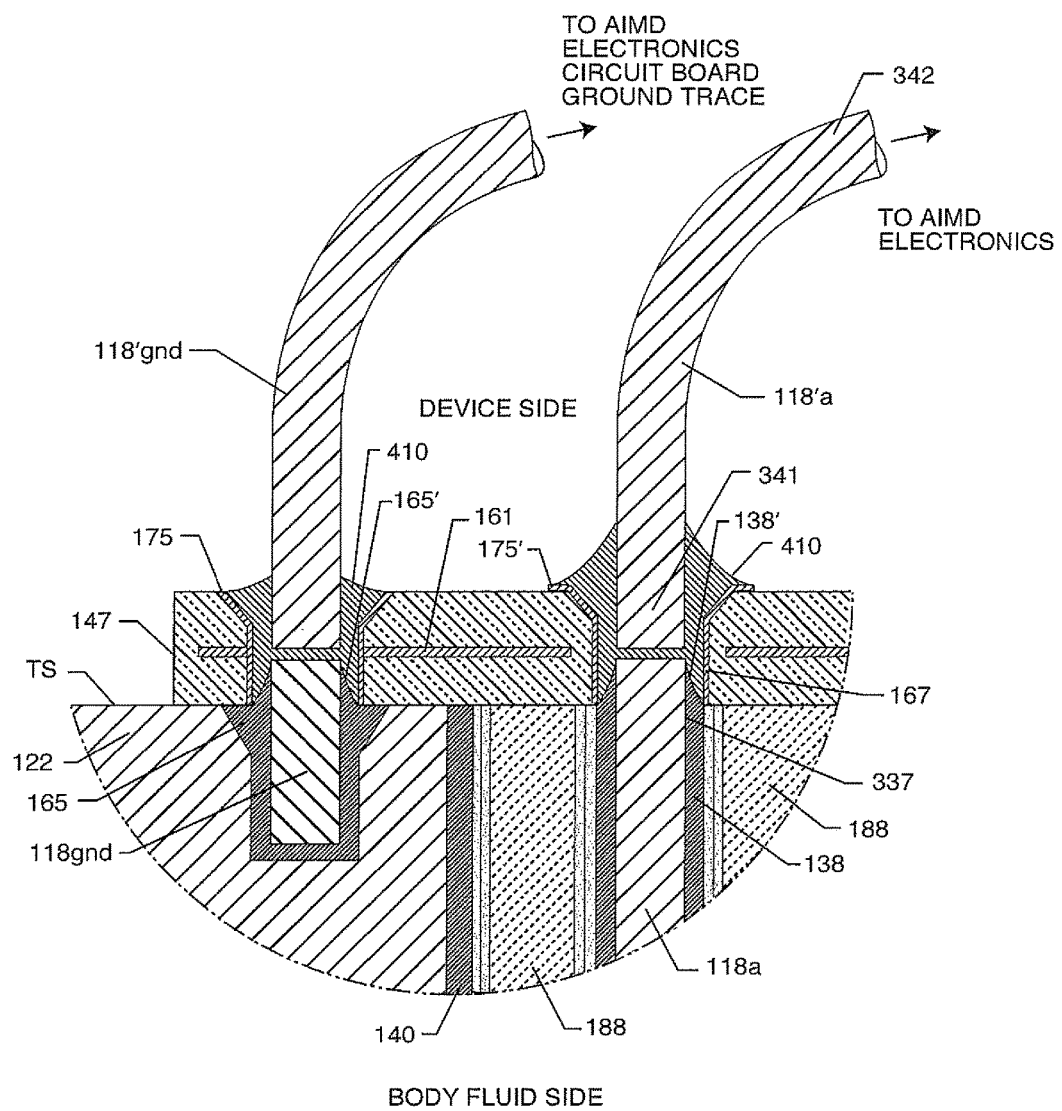
FIG. 39A is similar to FIG. 39 now showing a meniscus of the gold braze attaching to the lead.
Figure 40:
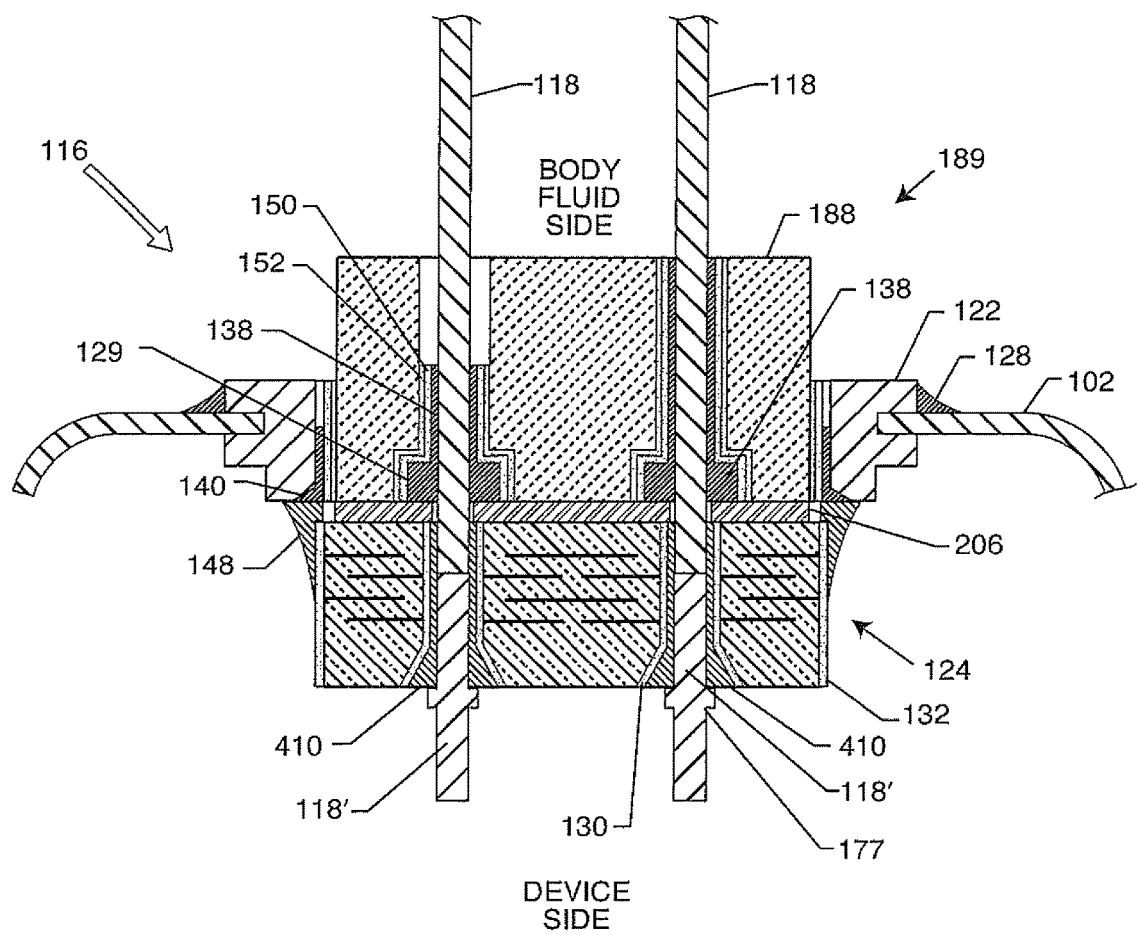
FIG. 40 is very similar to FIG. 8, except that the device side pins have been formed into wire wrapped terminals.
Figure 45A:
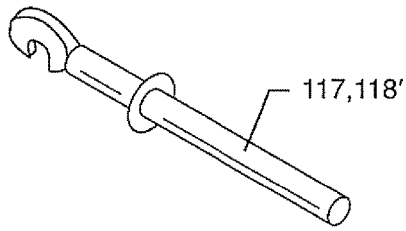
FIG. 45A is a perspective view of new embodiment of pin used in the present invention.
Figure 45B:
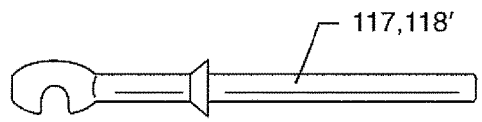
FIG. 45B is the side view of the structure of FIG. 45A.
Figure 46A:
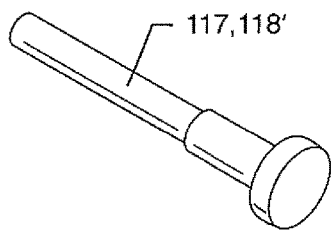
FIG. 46A is a perspective view of new embodiment of pin used in the present invention.
Figure 46B:
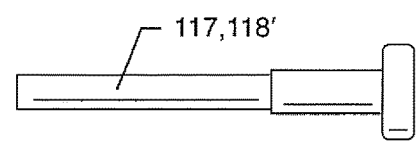
FIG. 46B is the side view of the structure of FIG. 46A.
Figure 47A:
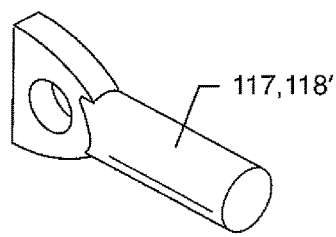
FIG. 47A is a perspective view of new embodiment of pin used in the present invention.
Figure 47B:
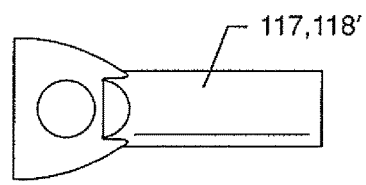
FIG. 47B is the side view of the structure of FIG. 47A.

Referring now to FIG. 39A, one can see that there is a gold brazed meniscus 165' and 138' that are formed as the gold wets and runs up the respective leads 118*gnd* and 118*a*. The run up of this gold braze meniscus can be controlled by gold braze furnace conditions, tolerances, the amount of gold in the gold braze preform and the like. However, in general, it is almost always that at least some meniscus forms. Referring once again to FIG. 39A, it is highly desirable that the meniscus 165' and 138' form so that the subsequent electrical connection material 410, which can be a solder or a thermal-setting conductive adhesive 410, flows down and around the gold braze meniscus portion 165', 138'. This increases the contact surface area to the gold, which is a non-oxidized surface and also puts the electrical connection material 410 largely in sheer with the gold braze meniscus 165', 138'.

It will be appreciated throughout this invention that gold brazes are generally shown flush or flat with the top side of either the ferrule or the insulator, but in general, it will be appreciated that for any of the drawings herein, a gold braze meniscus, such as illustrated in FIG. 39A, as elements 165' and 138' would be more typical.

FIGS. 41A through 48B show a variety of wire-wrapped terminals in both isometric and side views (for example, FIG. 41A is an isometric view and FIG. 41B is a side view of alternative wire-wrapped pins that could replace the pin 131 previously illustrated in FIG. 11). Included in drawings of FIG. 41*a* through 48B are wire-wrapped pins, pin connectors, crimped pins and the like. In general, referring back to FIGS. 41A through 48B, it will be appreciated that the round or cylindrical portion is the portion that is designed to be inserted into the feedthrough capacitor of FIG. 11. It will also be appreciated that any of the device side leadwires described in FIGS. 36 through 39 may be replaced by any of the wire-wrapped pin configurations illustrated in FIGS.

Figure 48A:
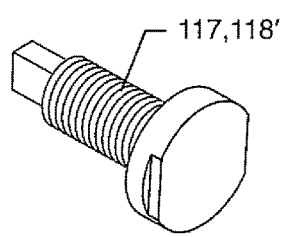
FIG. 48A is a perspective view of new embodiment of pin used in the present invention.
Figure 48B:
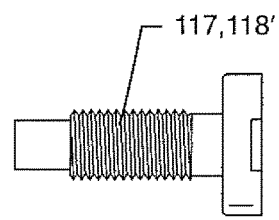
FIG. 48B is the side view of the structure of FIG. 48A.

41A through 48B. Referring once again to FIGS. 41A through 48B, it will be appreciated that all of these are adapted for attachment of a low cost leadwire that would be routed to AIMD electronics (not shown). In general, the pins and connectors illustrated in FIGS. 41A through 48B, would generally be of low cost materials, such as drawn copper and the like, and would generally be plated perhaps with nickel and gold plated or even tin plated. FIGS. 48A and 48B illustrate wire bond pads. In this case, the material might be of Cobar, which is suitable for thermal-sonic or ultrasonic wire bonding. It will be appreciated that the wire bond pads of FIGS. 48A and 48B are shown as cylindrical, but they could be square, rectangular or any other shape.

Figure 49:
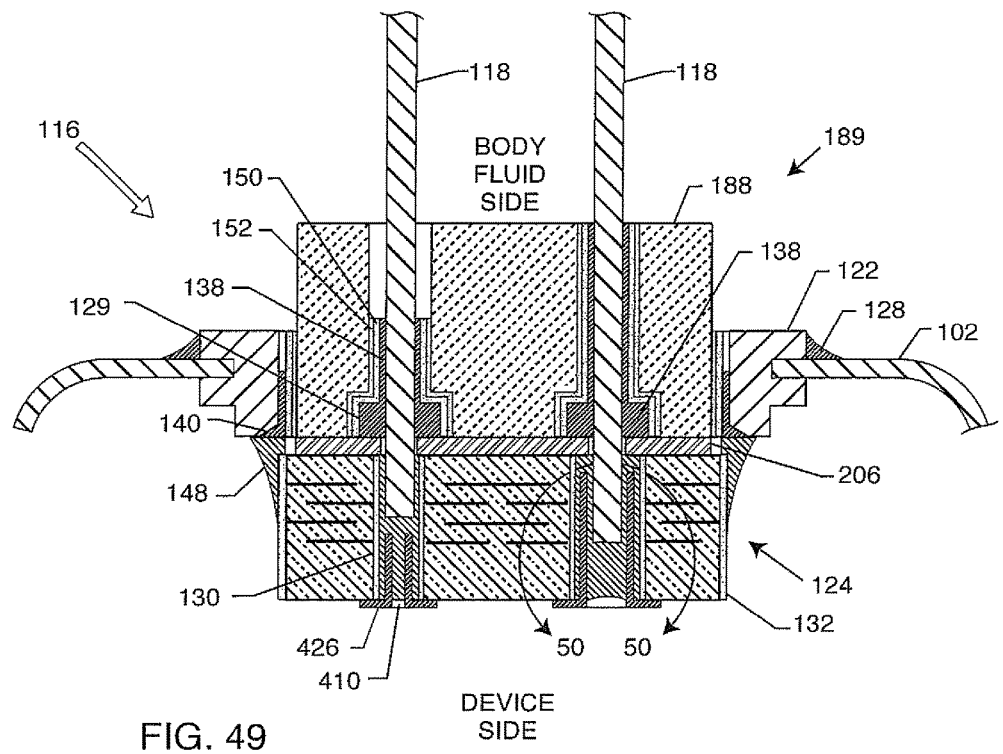
FIG. 49 is very similar to FIG. 12, except that an eyelet is used in place of leadwire and its insulation.

FIG. 49 is very similar to FIG. 12, except that an eyelet 426 is used in place of leadwire 118' and its insulation 123. This eyelet 426 can abut pin 118 as shown on the left side. In both cases, the solder 410 will flow down around both the inside and outside diameters of the eyelet and also around the outside diameter and end of pin 118 thereby, making a very mechanically strong shear connection. As shown on the right hand side of FIG. 49, the eyelet 426 can overlap pin 118, which would provide even more strength due to the solder that is in shear between the inside diameter of the eyelet and the outside diameter of pin 118. The eyelet is designed to facilitate convenient wire bonding by a customer. Wire bonding is well known in the art and could involve a round or a flat ribbon wire that would be electrically and mechanically connected to the device side of the eyelet 426 and then connect to a circuit board or internal AIMD electronics (not shown).

Figure 50:
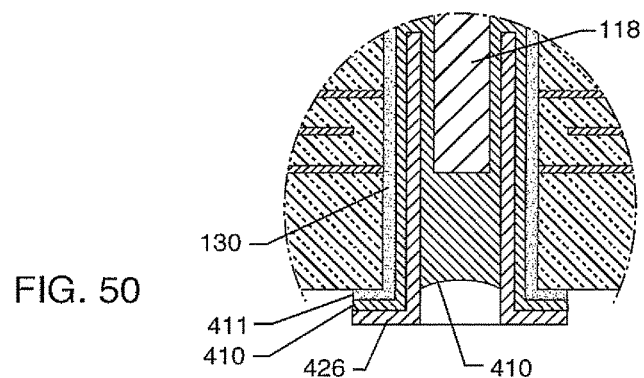
FIG. 50 is taken generally from section 50-50 of FIG. 49 and illustrates that the capacitor inside diameter or via hole metallization may extend onto the device side of the feedthrough capacitor forming a white-wall tire configuration, as previously described in FIG. 12.

FIG. 50 is taken generally from section 50-50 of FIG. 49 and illustrates that the capacitor inside diameter or via hole metallization 130 may extend onto the device side of the feedthrough capacitor forming a white-wall tire configuration 411, as previously described in FIG. 12. This would allow solder 410 (or a thermal-setting conductive adhesive) to not only flow down around the inside diameter (or via hole) of the feedthrough capacitor, but it would also flow all around the eyelet and also form a solder joint between the bottom surface of the top of the eyelet 426 and the white-wall tire metallization 411. As mentioned in FIG. 12, this would greatly increase the mechanical strength of a connection between the eyelet 426 and the feedthrough capacitor 124. Importantly, this also provides an even lower electrical resistivity between the eyelet and the capacitor metallization, and corresponding active electrode plates 134. It will be appreciated that the white-wall tire structure 411, as illustrated in FIG. 50, could be applied to any of the feedthrough capacitors previously described herein.

It will be understood to those skilled in the art that brazing materials that can be used to practice the present invention will include materials with a wide range of melting points to facilitate multi-stage brazing. This technique is used when brazing assemblies comprise several joints that cannot be brazed in a single operation. For such assemblies a high-melting alloy is used to make the first joint, and alloys with successively lower melting points are used for subsequent joints.

The primary braze material used for implantable feedthrough assemblies is pure gold (99.99%). In multi-stage brazing, a biocompatible gold alloy braze material may alternately be used to form a braze joint which hermetically seals the feedthrough into the case. One particular gold alloy braze is one which contains more than 50% gold by weight. Two non-limiting examples for lower temperature, multi-stage biocompatible brazing (<850° C.) include: 82Au-18In (530° C.) and 88Au-12Ge (356° C.). The ductility, oxidation resistance, and wettability of gold and gold alloys of compositions more than 50% gold by weight make these brazes a good choice for creating and sustaining a hermetic seal.

In cases where the risk of direct body fluid contact is negligible, other braze alloys can be used. Among the alloys that could be considered are, by weight percent: copper/silver (28/72)—MP 780° C., indium/copper/silver (10/27/63)—MP 685-730° C., gold/nickel (82/18)—MP 950° C., nickel/gold/copper (3/35/62)—MP 1000-1030° C., gold/nickel/titanium compositions including those disclosed in U.S. Pat. No. 4,938,922, the contents of which are incorporated herein by reference, Johnson Matthey silver-copper eutectic and pure metal brazes, Pallabraze alloys and Orobraze alloys.

The best control of braze volumes is achieved by using die cut braze performs. This assures a consistent braze volume for all seals in a lot. However, a braze ring can also be made by cutting loops of wire off of a coil wrapped around a mandrel. The rings created this way usually need to be gently flattened and squeezed to close any cutting gap. A ceramic body can be joined to the flange or the terminal pin or filled via in a number of ways, including brazing, active metal brazing, ceramic/glass/metal joining, transient liquid phase bonding, or other suitable techniques.

Active metal braze materials may also be considered. These materials have the primary braze material combined by forging or cladding to a small amount of another metal, usually titanium. It is known that the addition of titanium to several braze alloy compositions results in increased reactivity and considerable improvement in wetting behavior with a ceramic material. The ceramic is wet by the formation of an intermetallic interfacial reaction product which can then form a joint with the braze alloy. In active metal brazing, the metal facilitates the bonding mechanism to an unmetalized ceramic surface, thus creating the hermetic seal. Flow characteristics for these alloys are limited since the addition of the metal may make them non-eutectic. They also tend to form joints that are more brittle than traditional sputtered seals. This disadvantage becomes less important as the feedthrough size becomes smaller. Active metal brazing would be appropriate where the size of the feedthrough insulator is too small to allow for traditional metallization.

Braze preforms manufactured from nano-gold particles offer yet another option for multi-stage brazing. Particle sizes less than about 5 nm allow melting temperatures of 700° C. or less depending on uniformity of size and size distribution. It will be known to one skilled in the art that the smaller the particle size, the lower the melting temperature. It would also be known to one skilled in the art that melting temperatures can be customized based on optimal particle size selection, mixing and preform manufacturing.

If fine gold wire is the desired start material to form braze rings, then melt temperature control is based on wire grain size. The smaller the grain size, the lower the melt temperature.

The chart shown in FIG. 51 details various solder compositions that may be used by one skilled in the art when manufacturing the present invention. This list is not meant to be a full and complete list, but rather shows some of the solder compositions that could be used with the present invention.

Although several embodiments have been described in detail for purposes of illustration, various modifications may be made to each without departing from the scope and spirit of the invention. Additionally, it is to be understood that any of the features taught herein could be applied to any of the embodiments taught herein. Accordingly, the invention is not to be limited, except as by the appended claims.

What is claimed is:

1. A hermetically sealed feedthrough subassembly attachable to an active implantable medical device (AIMD), the feedthrough subassembly comprising:
   a) an insulator substrate assembly, comprising:
      i) an insulator body defined as having a body fluid side opposite a device side, the body fluid side and device side separated and connected by at least one outer perimeter surface;
      ii) at least one via hole disposed through the insulator body and extending from the body fluid side to the device side;
      iii) an internal metallization formed at least partially on an inside of the at least one via hole;
      iv) a first conductive leadwire extending from a first end to a second end, wherein the first conductive leadwire is at least partially disposed within the at least one via hole and wherein the first conductive leadwire first end is disposed outwardly beyond the device side of the insulator body;
      v) a first braze residing at least partially between the first conductive leadwire and the internal metallization, the first braze forming a first hermetic seal separating the body fluid side from the device side; and
      vi) an external metallization disposed at least partially on the at least one outer perimeter surface of the insulator body; and
   b) a ferrule, comprising:
      i) a conductive ferrule body defined as having a ferrule first side opposite a ferrule second side and defining a ferrule opening between and through the ferrule first and second sides, wherein the insulator body is at least partially disposed within the ferrule opening; and
      ii) a second braze residing at least partially between the external metallization of the insulator body and the conductive ferrule body, the second braze forming a second hermetic seal hermetically sealing the ferrule opening;
   c) a feedthrough filter capacitor disposed on the device side, the feedthrough filter capacitor comprising:
      i) at least one active electrode plate disposed parallel and spaced from at least one ground electrode plate, wherein the active and ground electrode plates are disposed within a capacitor dielectric substrate;
      ii) a first passageway disposed through the capacitor dielectric substrate and disposed perpendicular to the active and ground electrode plates; and
      iii) a capacitor internal metallization disposed within the first passageway and being electrically connected to the at least one active electrode plate and in non-conductive relation with the at least one ground electrode plate;
      iv) wherein the first conductive leadwire first end is disposed within the first passageway;
   d) a second conductive leadwire disposed on the device side and having a second conductive leadwire first end at least partially disposed within the first passageway of the feedthrough filter capacitor and having a second conductive leadwire second end disposed outwardly beyond the feedthrough filter capacitor, the second conductive leadwire second end being configured to be connectable to electronics internal to the AIMD, wherein the second conductive leadwire first end is at, near or adjacent to the first conductive leadwire first end; and
   e) a first electrically conductive material forming at least a three-way electrical connection electrically connecting the second conductive leadwire first end, the first conductive leadwire first end and the capacitor internal metallization together.

2. The feedthrough subassembly of claim 1, wherein the first electrically conductive material is selected from the group consisting of a solder, a solder BGA, a solder paste, a conductive epoxy, and a conductive polyimide.

3. The feedthrough subassembly of claim 1, wherein the first conductive leadwire is not of the same material as the second conductive leadwire.

4. The feedthrough subassembly of claim 1, wherein the first conductive leadwire comprises platinum, palladium, niobium, tantalum or alloys thereof.

5. The feedthrough subassembly of claim 1, wherein the first braze and second braze each comprise a gold braze.

6. The feedthrough subassembly of claim 5, wherein the first electrically conductive material directly contacts and is electrically connected to the first gold braze.

7. The feedthrough subassembly of claim 1, wherein the first braze is disposed at or near the device side and does not extend to, at or near the body fluid side.

8. The feedthrough subassembly of claim 1, wherein the first braze is disposed at or near the device side and does extend to, at or near the body fluid side.

9. The feedthrough subassembly of claim 1, wherein the first and second hermetic seals have a leak rate no greater than $1\times10^{-7}$ std cc He/sec.

10. The feedthrough subassembly of claim 1, wherein the external metallization disposed at least partially on the at least one outer perimeter surface of the insulator body comprises an adhesion metallization and a wetting metallization, wherein the adhesion metallization is disposed at least partially on the at least one outer perimeter surface of the insulator body and wherein the wetting metallization is disposed on the adhesion metallization.

11. The feedthrough subassembly of claim 1, wherein the adhesion metallization or the wetting metallization comprise at least one of niobium or titanium.

12. The feedthrough subassembly of claim 1, wherein an insulative washer is disposed between the insulator substrate assembly and the feedthrough filter capacitor.

13. The feedthrough subassembly of claim 1, wherein the ferrule is configured to be joined to an opening in an AIMD housing by a laser weld or braze.

14. The feedthrough subassembly of claim 1, wherein the ferrule is formed from and as a continuous part of an AIMD housing.

15. The feedthrough subassembly of claim 1, including a capacitor external metallization disposed on an outside perimeter surface of the capacitor dielectric substrate and being electrically connected to the at least one ground electrode plate and in non-conductive relation with the at least one active electrode plate.

16. The feedthrough subassembly of claim 15, including a second electrically conductive material electrically connecting the capacitor external metallization to the ferrule and/or to the second braze.

17. The feedthrough subassembly of claim 1, including at least one internal ground plate disposed within the insulator body and being electrically connected to the at least one ground electrode plate of the feedthrough filter capacitor and being electrically connected to the ferrule.

18. The feedthrough subassembly of claim 1, including a third conductive ground leadwire at least partially disposed within the insulator body and having a third conductive ground leadwire first end disposed outwardly beyond the device side of the insulator body, wherein the third conductive ground leadwire is electrically connected to the at least one ground electrode plate of the feedthrough filter capacitor.

19. The feedthrough subassembly of claim 18, including a braze channel electrically connected between and to the third conductive leadwire and the ferrule.

20. The feedthrough subassembly of claim 19, wherein the feedthrough filter capacitor does not have an external metallization disposed on an outside perimeter surface of the capacitor dielectric substrate.

21. The feedthrough subassembly of claim 19, including a conductive clip electrically connected between and to the third conductive leadwire and the ferrule.

22. The feedthrough subassembly of claim 19, wherein the conductive ferrule body includes a conductive peninsula extending at least partially into the ferrule opening, and wherein the third conductive leadwire is electrically connected to the conductive peninsula with a third braze.

23. A hermetically sealed feedthrough subassembly attachable to an active implantable medical device (AIMD), the feedthrough subassembly comprising:
a) an insulator body defined as having a body fluid side opposite a device side, the body fluid side and device side separated and connected by at least one outer perimeter surface, wherein at least one via hole disposed through the insulator body extends from the body fluid side to the device side;
b) an internal metallization formed at least partially on an inside of the at least one via hole;
c) a first conductive leadwire extending from a first end to a second end, wherein the first conductive leadwire is at least partially disposed within the at least one via hole and wherein the first conductive leadwire first end is disposed outwardly beyond the device side of the insulator body;
d) a first gold braze residing at least partially between the first conductive leadwire and the internal metallization, the first gold braze forming a first hermetic seal separating the body fluid side from the device side;
e) an external metallization disposed at least partially on the at least one outer perimeter surface of the insulator body; and
f) a conductive ferrule body defined as having a ferrule first side opposite a ferrule second side and defining a ferrule opening between and through the ferrule first and second sides, wherein the conductive ferrule body is configured to be joined to an opening in an AIMD housing by a laser weld or braze;
g) a second gold braze residing at least partially between the external metallization of the insulator body and the conductive ferrule body, the second gold braze forming a second hermetic seal hermetically sealing the ferrule opening to the conductive ferrule body;
h) a feedthrough filter capacitor disposed on the device side, the feedthrough filter capacitor comprising:
  i) at least one active electrode plate disposed parallel and spaced from at least one ground electrode plate, wherein the active and ground electrode plates are disposed within a capacitor dielectric substrate;
  ii) a first passageway disposed through the capacitor dielectric substrate and disposed perpendicular to the first and second plates; and
  iii) a capacitor internal metallization disposed within the first passageway and being electrically connected to the at least one active electrode plate and in non-conductive relation with the at least one ground electrode plate;
  iv) wherein the first conductive leadwire first end is disposed within the first passageway;
i) a second conductive leadwire disposed on the device side and having a second conductive leadwire first end at least partially disposed within the first passageway of the feedthrough filter capacitor and having a second conductive leadwire second end disposed outwardly beyond the feedthrough filter capacitor, the second conductive leadwire second end being configured to be connectable to electronics internal to the AIMD, wherein the second conductive leadwire first end is at, near or adjacent to the first conductive leadwire first end, and wherein the first conductive leadwire is not of the same material as the second conductive leadwire; and
j) a first electrically conductive material forming at least a three-way electrical connection electrically connecting the second conductive leadwire first end, the first conductive leadwire first end and the capacitor internal metallization together.

* * * * *